United States Patent
Tentori et al.

(10) Patent No.: US 12,129,516 B2
(45) Date of Patent: Oct. 29, 2024

(54) QUANTITATIVE AND AUTOMATED PERMEABILIZATION PERFORMANCE EVALUATION FOR SPATIAL TRANSCRIPTOMICS

(71) Applicant: 10x Genomics, Inc., Pleasanton, CA (US)

(72) Inventors: Augusto Manuel Tentori, Pleasanton, CA (US); Rajiv Bharadwaj, Pleasanton, CA (US); Hanyoup Kim, Pleasanton, CA (US); Siyuan Xing, Pleasanton, CA (US)

(73) Assignee: 10x Genomics, Inc., Pleasanton, CA (US)

(*) Notice: Subject to any disclaimer, the term of this patent is extended or adjusted under 35 U.S.C. 154(b) by 341 days.

(21) Appl. No.: 17/796,463

(22) PCT Filed: Feb. 5, 2021

(86) PCT No.: PCT/US2021/016833
§ 371 (c)(1),
(2) Date: Jul. 29, 2022

(87) PCT Pub. No.: WO2021/158925
PCT Pub. Date: Aug. 12, 2021

(65) Prior Publication Data
US 2023/0047782 A1    Feb. 16, 2023

Related U.S. Application Data

(60) Provisional application No. 62/989,062, filed on Mar. 13, 2020, provisional application No. 62/971,711, filed on Feb. 7, 2020.

(51) Int. Cl.
*C12Q 1/6837* (2018.01)
*G02B 21/36* (2006.01)

(52) U.S. Cl.
CPC ........ *C12Q 1/6837* (2013.01); *G02B 21/367* (2013.01); *G06T 2207/10056* (2013.01)

(58) Field of Classification Search
CPC .. C12Q 1/6837; C12Q 1/6834; C12Q 1/6841; C12Q 2533/101; C12Q 2533/107;
(Continued)

(56) References Cited

U.S. PATENT DOCUMENTS

| 4,683,195 A | 7/1987 | Mullis |
| 4,683,202 A | 7/1987 | Mullis |

(Continued)

FOREIGN PATENT DOCUMENTS

| AU | 2003200718 | 10/2006 |
| CN | 1273609 | 11/2000 |

(Continued)

OTHER PUBLICATIONS

D. Sel, A. M. Lebar and D. Miklavcic, "Feasibility of Employing Model-Based Optimization of Pulse Amplitude and Electrode Distance for Effective Tumor Electropermeabilization," in IEEE Transactions on Biomedical Engineering, vol. 54, No. 5, pp. 773-781, May 2007 (Year: 2007).*

(Continued)

*Primary Examiner* — Siamak Harandi
*Assistant Examiner* — Emma Rose Goebel
(74) *Attorney, Agent, or Firm* — Fish & Richardson P.C.

(57) ABSTRACT

Quantitative methods for optimizing the permeabilization of cellular tissues for spatial transcriptomics are provided. Also provided is an instrument for quantitatively optimizing the permeabilization of cellular tissues used for spatial transcriptomics.

19 Claims, 25 Drawing Sheets

(58) Field of Classification Search
CPC ........ C12Q 2535/122; C12Q 2565/514; C12Q 2565/519; C12Q 2535/131; C12Q 2521/531; C12Q 2525/173; C12Q 2525/179; C12Q 2563/179; C12Q 2565/537; G02B 21/367; G06T 2207/10056
See application file for complete search history.

(56) References Cited

U.S. PATENT DOCUMENTS

| | | |
|---|---|---|
| 4,800,159 A | 1/1989 | Mullis |
| 4,883,867 A | 11/1989 | Lee |
| 4,965,188 A | 10/1990 | Mullis |
| 4,988,617 A | 1/1991 | Landegren et al. |
| 5,002,882 A | 3/1991 | Lunnen |
| 5,130,238 A | 7/1992 | Malek |
| 5,308,751 A | 5/1994 | Ohkawa |
| 5,321,130 A | 6/1994 | Yue |
| 5,410,030 A | 4/1995 | Yue |
| 5,436,134 A | 7/1995 | Haugland |
| 5,455,166 A | 10/1995 | Walker |
| 5,494,810 A | 2/1996 | Barany et al. |
| 5,503,980 A | 4/1996 | Cantor |
| 5,512,439 A | 4/1996 | Hornes |
| 5,512,462 A | 4/1996 | Cheng |
| 5,582,977 A | 12/1996 | Yue |
| 5,599,675 A | 2/1997 | Brenner |
| 5,641,658 A | 6/1997 | Adams |
| 5,648,245 A | 7/1997 | Fire et al. |
| 5,658,751 A | 8/1997 | Yue |
| 5,695,940 A | 12/1997 | Drmanac et al. |
| 5,750,341 A | 5/1998 | Macevicz |
| 5,763,175 A | 6/1998 | Brenner |
| 5,830,711 A | 11/1998 | Barany et al. |
| 5,837,832 A | 11/1998 | Chee et al. |
| 5,854,033 A | 12/1998 | Lizardi |
| 5,863,753 A | 1/1999 | Haugland |
| 5,871,921 A | 2/1999 | Landegren et al. |
| 5,912,148 A | 6/1999 | Eggerding |
| 5,925,545 A | 7/1999 | Reznikoff et al. |
| 5,928,906 A | 7/1999 | Koester et al. |
| 5,958,775 A | 9/1999 | Wickstrrom |
| 5,962,272 A | 10/1999 | Chenchik et al. |
| 5,965,443 A | 10/1999 | Reznikoff et al. |
| 6,013,440 A | 1/2000 | Lipshutz |
| 6,027,889 A | 2/2000 | Barany et al. |
| 6,054,274 A | 4/2000 | Sampson et al. |
| 6,060,240 A | 5/2000 | Kamb et al. |
| 6,130,073 A | 10/2000 | Eggerding |
| 6,143,496 A | 11/2000 | Brown |
| 6,153,389 A | 11/2000 | Haarer |
| 6,159,736 A | 12/2000 | Reznikoff et al. |
| 6,165,714 A | 12/2000 | Lane et al. |
| 6,210,891 B1 | 4/2001 | Nyren |
| 6,210,894 B1 | 4/2001 | Brennan |
| 6,214,587 B1 | 4/2001 | Dattagupta |
| 6,251,639 B1 | 6/2001 | Kurn |
| 6,258,568 B1 | 7/2001 | Nyren |
| 6,266,459 B1 | 7/2001 | Walt |
| 6,268,148 B1 | 7/2001 | Barany et al. |
| 6,274,320 B1 | 8/2001 | Rothberg |
| 6,291,180 B1 | 9/2001 | Chu |
| 6,291,187 B1 | 9/2001 | Kingsmore et al. |
| 6,300,063 B1 | 10/2001 | Lipshutz et al. |
| 6,309,824 B1 | 10/2001 | Drmanac |
| 6,323,009 B1 | 11/2001 | Lasken et al. |
| 6,344,316 B1 | 2/2002 | Lockhart |
| 6,344,329 B1 | 2/2002 | Lizardi et al. |
| 6,355,431 B1 | 3/2002 | Chee |
| 6,368,801 B1 | 4/2002 | Faruqi |
| 6,401,267 B1 | 6/2002 | Drmanac |
| 6,404,907 B1 | 6/2002 | Gilchrist |
| 6,432,360 B1 | 8/2002 | Church et al. |
| 6,503,713 B1 | 1/2003 | Rana |
| 6,506,561 B1 | 1/2003 | Cheval et al. |
| 6,534,266 B1 | 3/2003 | Singer |
| 6,544,732 B1 | 4/2003 | Chee |
| 6,573,043 B1 | 6/2003 | Cohen et al. |
| 6,579,695 B1 | 6/2003 | Lambalot |
| 6,620,584 B1 | 9/2003 | Chee |
| 6,632,641 B1 | 10/2003 | Brennan |
| 6,737,236 B1 | 5/2004 | Pieken et al. |
| 6,770,441 B2 | 8/2004 | Dickinson |
| 6,773,886 B2 | 8/2004 | Kaufman |
| 6,787,308 B2 | 9/2004 | Balasubramanian |
| 6,797,470 B2 | 9/2004 | Barany et al. |
| 6,800,453 B2 | 10/2004 | Labaer |
| 6,812,005 B2 | 11/2004 | Fan et al. |
| 6,828,100 B1 | 12/2004 | Ronaghi |
| 6,833,246 B2 | 12/2004 | Balasubramanian |
| 6,852,487 B1 | 2/2005 | Barany et al. |
| 6,859,570 B2 | 2/2005 | Walt |
| 6,864,052 B1 | 3/2005 | Drmanac |
| 6,867,028 B2 | 3/2005 | Janulaitis |
| 6,872,816 B1 | 3/2005 | Hall et al. |
| 6,875,572 B2 | 4/2005 | Prudent et al. |
| 6,890,741 B2 | 5/2005 | Fan et al. |
| 6,897,023 B2 | 5/2005 | Fu |
| 6,913,881 B1 | 7/2005 | Aizenstein et al. |
| 6,942,968 B1 | 9/2005 | Dickinson et al. |
| 7,011,944 B2 | 3/2006 | Prudent et al. |
| 7,057,026 B2 | 6/2006 | Barnes |
| 7,083,980 B2 | 8/2006 | Reznikoff et al. |
| 7,115,400 B1 | 10/2006 | Adessi |
| 7,118,883 B2 | 10/2006 | Inoue |
| 7,166,431 B2 | 1/2007 | Chee et al. |
| 7,192,735 B2 | 3/2007 | Lambalot |
| 7,211,414 B2 | 5/2007 | Hardin |
| 7,255,994 B2 | 8/2007 | Lao |
| 7,258,976 B2 | 8/2007 | Mitsuhashi |
| 7,282,328 B2 | 10/2007 | Kong et al. |
| 7,297,518 B2 | 11/2007 | Quake |
| 7,329,492 B2 | 2/2008 | Hardin |
| 7,358,047 B2 | 4/2008 | Hafner et al. |
| 7,361,488 B2 | 4/2008 | Fan et al. |
| 7,378,242 B2 | 5/2008 | Hurt |
| 7,393,665 B2 | 7/2008 | Brenner |
| 7,405,281 B2 | 7/2008 | Xu |
| 7,407,757 B2 | 8/2008 | Brenner |
| 7,473,767 B2 | 1/2009 | Dimitrov |
| 7,499,806 B2 | 3/2009 | Kermani et al. |
| 7,537,897 B2 | 5/2009 | Brenner |
| 7,563,576 B2 | 7/2009 | Chee |
| 7,579,153 B2 | 8/2009 | Brenner |
| 7,582,420 B2 | 9/2009 | Oliphant et al. |
| 7,601,498 B2 | 10/2009 | Mao |
| 7,608,434 B2 | 10/2009 | Reznikoff et al. |
| 7,611,869 B2 | 11/2009 | Fan |
| 7,635,566 B2 | 12/2009 | Brenner |
| 7,666,612 B2 | 2/2010 | Johnsson |
| 7,674,752 B2 | 3/2010 | He |
| 7,709,198 B2 | 5/2010 | Luo et al. |
| 7,776,547 B2 | 8/2010 | Roth |
| 7,776,567 B2 | 8/2010 | Mao |
| 7,803,943 B2 | 9/2010 | Mao |
| 7,888,009 B2 | 2/2011 | Barany et al. |
| 7,892,747 B2 | 2/2011 | Barany et al. |
| 7,910,304 B2 | 3/2011 | Drmanac |
| 7,914,981 B2 | 3/2011 | Barany et al. |
| 7,955,794 B2 | 6/2011 | Shen et al. |
| 7,960,119 B2 | 6/2011 | Chee |
| 7,985,565 B2 | 7/2011 | Mayer et al. |
| 8,003,354 B2 | 8/2011 | Shen et al. |
| 8,076,063 B2 | 12/2011 | Fan |
| 8,092,784 B2 | 1/2012 | Mao |
| 8,148,068 B2 | 4/2012 | Brenner |
| 8,206,917 B2 | 6/2012 | Chee |
| 8,268,554 B2 | 9/2012 | Schallmeiner |
| 8,288,103 B2 | 10/2012 | Oliphant |
| 8,288,122 B2 | 10/2012 | O'Leary et al. |
| 8,383,338 B2 | 2/2013 | Kitzman |
| 8,431,691 B2 | 4/2013 | McKernan et al. |
| 8,460,865 B2 | 6/2013 | Chee |
| 8,481,257 B2 | 7/2013 | Van Eijk |

(56) References Cited

U.S. PATENT DOCUMENTS

| | | |
|---|---|---|
| 8,481,258 B2 | 7/2013 | Church et al. |
| 8,481,292 B2 | 7/2013 | Casbon |
| 8,481,698 B2 | 7/2013 | Lieberman et al. |
| 8,507,204 B2 | 8/2013 | Pierce et al. |
| 8,519,115 B2 | 8/2013 | Webster et al. |
| 8,551,710 B2 | 10/2013 | Bernitz et al. |
| 8,568,979 B2 | 10/2013 | Stuelpnagel et al. |
| 8,586,310 B2 | 11/2013 | Mitra |
| 8,597,891 B2 | 12/2013 | Barany et al. |
| 8,603,743 B2 | 12/2013 | Liu et al. |
| 8,604,182 B2 | 12/2013 | Luo et al. |
| 8,614,073 B2 | 12/2013 | Van Eijk |
| 8,624,016 B2 | 1/2014 | Barany et al. |
| 8,685,889 B2 | 4/2014 | Van Eijk |
| 8,741,564 B2 | 6/2014 | Seligmann |
| 8,741,606 B2 | 6/2014 | Casbon |
| 8,771,950 B2 | 7/2014 | Church et al. |
| 8,785,353 B2 | 7/2014 | Van Eijk |
| 8,790,873 B2 | 7/2014 | Namsaraev et al. |
| 8,809,238 B2 | 8/2014 | Livak et al. |
| 8,815,512 B2 | 8/2014 | Van Eijk |
| 8,835,358 B2 | 9/2014 | Fodor |
| 8,865,410 B2 | 10/2014 | Shendure |
| 8,906,626 B2 | 12/2014 | Oliphant et al. |
| 8,911,945 B2 | 12/2014 | Van Eijk |
| 8,936,912 B2 | 1/2015 | Mitra |
| 8,951,726 B2 | 2/2015 | Luo et al. |
| 8,951,728 B2 | 2/2015 | Rasmussen |
| 8,986,926 B2 | 3/2015 | Ferree et al. |
| 9,005,891 B2 | 4/2015 | Sinicropi et al. |
| 9,005,935 B2 | 4/2015 | Belyaev |
| 9,023,768 B2 | 5/2015 | Van Eijk |
| 9,062,348 B1 | 6/2015 | Van Eijk |
| 9,080,210 B2 | 7/2015 | Van Eijk |
| 9,194,001 B2 | 11/2015 | Brenner |
| 9,201,063 B2 | 12/2015 | Sood et al. |
| 9,273,349 B2 | 3/2016 | Nguyen et al. |
| 9,290,808 B2 | 3/2016 | Fodor |
| 9,290,809 B2 | 3/2016 | Fodor |
| 9,328,383 B2 | 5/2016 | Van Eijk |
| 9,334,536 B2 | 5/2016 | Van Eijk |
| 9,371,563 B2 | 6/2016 | Geiss et al. |
| 9,371,598 B2 | 6/2016 | Chee |
| 9,376,716 B2 | 6/2016 | Van Eijk |
| 9,376,717 B2 | 6/2016 | Gao et al. |
| 9,376,719 B2 | 6/2016 | Eijk |
| 9,416,409 B2 | 8/2016 | Hayden |
| 9,447,459 B2 | 9/2016 | Van Eijk |
| 9,453,256 B2 | 9/2016 | Van Eijk |
| 9,493,820 B2 | 11/2016 | Van Eijk |
| 9,506,061 B2 | 11/2016 | Brown et al. |
| 9,512,422 B2 | 12/2016 | Barnard et al. |
| 9,574,230 B2 | 2/2017 | Van Eijk |
| 9,593,365 B2 | 3/2017 | Frisen et al. |
| 9,598,728 B2 | 3/2017 | Barany et al. |
| 9,624,538 B2 | 4/2017 | Church et al. |
| 9,644,204 B2 | 5/2017 | Hindson et al. |
| 9,657,335 B2 | 5/2017 | Van Eijk |
| 9,670,542 B2 | 6/2017 | Eijk |
| 9,694,361 B2 | 7/2017 | Bharadwaj |
| 9,702,004 B2 | 7/2017 | Van Eijk |
| 9,714,446 B2 | 7/2017 | Webster et al. |
| 9,714,937 B2 | 7/2017 | Dunaway |
| 9,727,810 B2 | 8/2017 | Fodor et al. |
| 9,745,627 B2 | 8/2017 | Van Eijk |
| 9,777,324 B2 | 10/2017 | Van Eijk |
| 9,783,841 B2 | 10/2017 | Nolan et al. |
| 9,790,476 B2 | 10/2017 | Gloeckner et al. |
| 9,816,134 B2 | 11/2017 | Namsaraev |
| 9,834,814 B2 | 12/2017 | Peter et al. |
| 9,850,536 B2 | 12/2017 | Oliphant et al. |
| 9,856,521 B2 | 1/2018 | Stevens et al. |
| 9,868,979 B2 | 1/2018 | Chee et al. |
| 9,879,313 B2 | 1/2018 | Chee et al. |
| 9,896,721 B2 | 2/2018 | Van Eijk |
| 9,898,576 B2 | 2/2018 | Van Eijk |
| 9,898,577 B2 | 2/2018 | Van Eijk |
| 9,902,991 B2 | 2/2018 | Sinicropi et al. |
| 9,909,167 B2 | 3/2018 | Samusik et al. |
| 9,938,566 B2 | 4/2018 | Shepard et al. |
| 9,957,550 B2 | 5/2018 | Yeakley et al. |
| 10,002,316 B2 | 6/2018 | Fodor et al. |
| 10,023,907 B2 | 7/2018 | Van Eijk |
| 10,030,261 B2 | 7/2018 | Frisen et al. |
| 10,035,992 B2 | 7/2018 | Gloeckner et al. |
| 10,041,949 B2 | 8/2018 | Bendall et al. |
| 10,059,989 B2 | 8/2018 | Giresi et al. |
| 10,059,990 B2 | 8/2018 | Boyden et al. |
| 10,095,832 B2 | 10/2018 | Van Eijk |
| 10,144,966 B2 | 12/2018 | Cantor |
| 10,208,982 B2 | 2/2019 | Bannish et al. |
| 10,227,639 B2 | 3/2019 | Levner et al. |
| 10,273,541 B2 | 4/2019 | Hindson et al. |
| 10,308,982 B2 | 6/2019 | Chee |
| 10,357,771 B2 | 7/2019 | Bharadwaj |
| 10,370,698 B2 | 8/2019 | Nolan et al. |
| 10,415,080 B2 | 9/2019 | Dunaway et al. |
| 10,465,235 B2 | 11/2019 | Gullberg et al. |
| 10,472,669 B2 | 11/2019 | Chee |
| 10,480,022 B2 | 11/2019 | Chee |
| 10,480,029 B2 | 11/2019 | Bent et al. |
| 10,494,667 B2 | 12/2019 | Chee |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,544,403 B2 | 1/2020 | Gloeckner et al. |
| 10,550,429 B2 | 2/2020 | Harada et al. |
| 10,590,244 B2 | 3/2020 | Delaney et al. |
| 10,633,648 B2 | 4/2020 | Seelig et al. |
| 10,640,816 B2 | 5/2020 | Beechem et al. |
| 10,640,826 B2 | 5/2020 | Church et al. |
| 10,669,569 B2 | 6/2020 | Gullberg et al. |
| 10,724,078 B2 | 7/2020 | Van Driel et al. |
| 10,725,027 B2 | 7/2020 | Bell |
| 10,774,372 B2 | 9/2020 | Chee et al. |
| 10,774,374 B2 | 9/2020 | Frisen et al. |
| 10,787,701 B2 | 9/2020 | Chee |
| 10,815,519 B2 | 10/2020 | Husain et al. |
| 10,829,803 B2 | 11/2020 | Terbrueggen et al. |
| 10,844,426 B2 | 11/2020 | Daugharthy et al. |
| 10,858,698 B2 | 12/2020 | Church et al. |
| 10,858,702 B2 | 12/2020 | Lucero et al. |
| 10,913,975 B2 | 2/2021 | So et al. |
| 10,914,730 B2 | 2/2021 | Chee et al. |
| 10,927,403 B2 | 2/2021 | Chee et al. |
| 10,961,566 B2 | 3/2021 | Chee |
| 11,001,879 B1 | 5/2021 | Chee |
| 11,008,607 B2 | 5/2021 | Chee |
| 11,046,996 B1 | 6/2021 | Chee et al. |
| 11,067,567 B2 | 7/2021 | Chee |
| 11,104,936 B2 | 8/2021 | Zhang et al. |
| 11,118,216 B2 | 9/2021 | Koshinsky et al. |
| 11,156,603 B2 | 10/2021 | Chee |
| 11,162,132 B2 | 11/2021 | Frisen et al. |
| 11,208,684 B2 | 12/2021 | Chee |
| 11,286,515 B2 | 3/2022 | Chee et al. |
| 11,293,917 B2 | 4/2022 | Chee |
| 11,299,774 B2 | 4/2022 | Frisen et al. |
| 11,313,856 B2 | 4/2022 | Chee |
| 11,332,790 B2 | 5/2022 | Chell et al. |
| 11,352,659 B2 | 6/2022 | Frisen et al. |
| 11,352,667 B2 | 6/2022 | Hauling et al. |
| 11,359,228 B2 | 6/2022 | Chee et al. |
| 11,365,442 B2 | 6/2022 | Chee |
| 11,371,086 B2 | 6/2022 | Chee |
| 11,384,386 B2 | 7/2022 | Chee |
| 11,390,912 B2 | 7/2022 | Frisen et al. |
| 11,401,545 B2 | 8/2022 | Chee |
| 11,407,992 B2 | 8/2022 | Dadhwal |
| 11,408,029 B2 | 8/2022 | Katiraee et al. |
| 11,434,524 B2 | 9/2022 | Ramachandran Iyer et al. |
| 11,459,607 B1 | 10/2022 | Terry et al. |
| 11,479,809 B2 | 10/2022 | Frisen et al. |

(56) References Cited

U.S. PATENT DOCUMENTS

| | | |
|---|---|---|
| 11,479,810 B1 | 10/2022 | Chee |
| 11,492,612 B1 | 11/2022 | Dadhwal |
| 11,501,440 B2 | 11/2022 | Weisenfeld et al. |
| 11,505,828 B2 | 11/2022 | Chell et al. |
| 11,512,308 B2 | 11/2022 | Gallant et al. |
| 11,519,022 B2 | 12/2022 | Chee |
| 11,519,033 B2 | 12/2022 | Schnall-Levin et al. |
| 11,530,438 B2 | 12/2022 | Persson et al. |
| 11,535,887 B2 | 12/2022 | Gallant et al. |
| 11,542,543 B2 | 1/2023 | Chee |
| 11,549,138 B2 | 1/2023 | Chee |
| 11,560,587 B2 | 1/2023 | Chee |
| 11,560,592 B2 | 1/2023 | Chew et al. |
| 11,560,593 B2 | 1/2023 | Chell et al. |
| 11,592,447 B2 | 2/2023 | Uytingco et al. |
| 11,608,498 B2 | 3/2023 | Gallant et al. |
| 11,608,520 B2 | 3/2023 | Galonska et al. |
| 11,613,773 B2 | 3/2023 | Frisen et al. |
| 11,618,897 B2 | 4/2023 | Kim et al. |
| 11,618,918 B2 | 4/2023 | Chee et al. |
| 11,624,063 B2 | 4/2023 | Dadhwal |
| 11,624,086 B2 | 4/2023 | Uytingco et al. |
| 11,634,756 B2 | 4/2023 | Chee |
| 11,649,485 B2 | 5/2023 | Yin et al. |
| 11,661,626 B2 | 5/2023 | Katiraee et al. |
| 11,680,260 B2 | 6/2023 | Kim et al. |
| 11,692,218 B2 | 7/2023 | Engblom et al. |
| 11,702,693 B2 | 7/2023 | Bharadwaj |
| 11,702,698 B2 | 7/2023 | Stoeckius |
| 11,713,480 B2 | 8/2023 | Lee |
| 11,732,292 B2 | 8/2023 | Chee |
| 11,732,299 B2 | 8/2023 | Ramachandran Iyer |
| 11,732,300 B2 | 8/2023 | Bava |
| 11,733,238 B2 | 8/2023 | Chee |
| 11,739,372 B2 | 8/2023 | Frisen et al. |
| 11,739,381 B2 | 8/2023 | Chew et al. |
| 11,753,673 B2 | 9/2023 | Chew et al. |
| 11,753,674 B2 | 9/2023 | Chee et al. |
| 11,753,675 B2 | 9/2023 | Ramachandran Iyer |
| 11,761,030 B2 | 9/2023 | Chee |
| 11,761,038 B1 | 9/2023 | Stoeckius |
| 11,767,550 B2 | 9/2023 | Chee |
| 11,768,175 B1 | 9/2023 | Kim et al. |
| 11,773,433 B2 | 10/2023 | Gallant et al. |
| 11,781,130 B2 | 10/2023 | Dadhwal |
| 11,788,122 B2 | 10/2023 | Frisen et al. |
| 11,795,498 B2 | 10/2023 | Frisen et al. |
| 11,795,507 B2 | 10/2023 | Chell et al. |
| 11,808,769 B2 | 11/2023 | Uytingco et al. |
| 11,821,024 B2 | 11/2023 | Chee et al. |
| 11,821,035 B1 | 11/2023 | Bent et al. |
| 11,827,935 B1 | 11/2023 | Ramachandran Iyer et al. |
| 11,835,462 B2 | 12/2023 | Bava |
| 11,840,687 B2 | 12/2023 | Gallant et al. |
| 11,840,724 B2 | 12/2023 | Chew et al. |
| 11,845,979 B2 | 12/2023 | Engblom et al. |
| 11,859,178 B2 | 1/2024 | Gallant et al. |
| 11,866,767 B2 | 1/2024 | Uytingco et al. |
| 11,866,770 B2 | 1/2024 | Chee |
| 11,873,482 B2 | 1/2024 | Kim et al. |
| 11,891,654 B2 | 2/2024 | Alvarado Martinez et al. |
| 11,898,205 B2 | 2/2024 | Bava |
| 11,926,822 B1 | 3/2024 | Gohil et al. |
| 11,926,863 B1 | 3/2024 | Boutet |
| 11,926,867 B2 | 3/2024 | Yin et al. |
| 11,933,957 B1 | 3/2024 | Tentori et al. |
| 11,952,627 B2 | 4/2024 | Stoeckius |
| 11,959,076 B2 | 4/2024 | Kim et al. |
| 11,959,130 B2 | 4/2024 | Galonska et al. |
| 11,965,213 B2 | 4/2024 | Williams |
| 11,970,739 B2 | 4/2024 | Chew et al. |
| 11,981,958 B1 | 5/2024 | Galonska |
| 11,981,960 B1 | 5/2024 | Lin et al. |
| 11,981,965 B2 | 5/2024 | Chell et al. |
| RE50,065 E | 7/2024 | Frisen et al. |
| 12,024,741 B2 | 7/2024 | Tentori et al. |
| 12,031,177 B1 | 7/2024 | Tentori et al. |
| 12,060,604 B2 | 8/2024 | Katiraee et al. |
| 2001/0055764 A1 | 12/2001 | Empendocles et al. |
| 2002/0040275 A1 | 4/2002 | Cravatt |
| 2002/0051986 A1 | 5/2002 | Baez et al. |
| 2002/0055100 A1 | 5/2002 | Kawashima |
| 2002/0058250 A1 | 5/2002 | Firth |
| 2002/0086441 A1 | 7/2002 | Baranov et al. |
| 2002/0164611 A1 | 11/2002 | Bamdad |
| 2003/0017451 A1 | 1/2003 | Wang et al. |
| 2003/0022207 A1 | 1/2003 | Balasubramanian |
| 2003/0064398 A1 | 4/2003 | Barnes |
| 2003/0092624 A1 | 5/2003 | Wang et al. |
| 2003/0138879 A1 | 7/2003 | Lambalot |
| 2003/0148335 A1 | 8/2003 | Shen et al. |
| 2003/0162216 A1 | 8/2003 | Gold |
| 2003/0165948 A1 | 9/2003 | Alsmadi et al. |
| 2003/0211489 A1 | 11/2003 | Shen et al. |
| 2003/0224419 A1 | 12/2003 | Corcoran |
| 2003/0232348 A1 | 12/2003 | Jones et al. |
| 2003/0232382 A1 | 12/2003 | Brennan |
| 2003/0235854 A1 | 12/2003 | Chan et al. |
| 2004/0033499 A1 | 2/2004 | Ilsley et al. |
| 2004/0067492 A1 | 4/2004 | Peng et al. |
| 2004/0082059 A1 | 4/2004 | Webb et al. |
| 2004/0096853 A1 | 5/2004 | Mayer |
| 2004/0106110 A1 | 6/2004 | Balasubramanian |
| 2004/0235103 A1 | 11/2004 | Reznikoff et al. |
| 2004/0248325 A1 | 12/2004 | Bukusoglu et al. |
| 2004/0259105 A1 | 12/2004 | Fan et al. |
| 2005/0003431 A1 | 1/2005 | Wucherpfennig |
| 2005/0014203 A1 | 1/2005 | Darfler et al. |
| 2005/0037393 A1 | 2/2005 | Gunderson et al. |
| 2005/0048580 A1 | 3/2005 | Labaer |
| 2005/0064460 A1 | 3/2005 | Holliger et al. |
| 2005/0095627 A1 | 5/2005 | Kolman et al. |
| 2005/0100900 A1 | 5/2005 | Kawashima et al. |
| 2005/0130173 A1 | 6/2005 | Leamon et al. |
| 2005/0136414 A1 | 6/2005 | Gunderson et al. |
| 2005/0164292 A1 | 7/2005 | Farooqui |
| 2005/0170373 A1 | 8/2005 | Monforte |
| 2005/0191656 A1 | 9/2005 | Drmanac et al. |
| 2005/0191698 A1 | 9/2005 | Chee et al. |
| 2005/0202433 A1 | 9/2005 | Van Beuningen |
| 2005/0227271 A1 | 10/2005 | Kwon |
| 2005/0239119 A1 | 10/2005 | Tsukada et al. |
| 2005/0260653 A1 | 11/2005 | LaBaer |
| 2005/0266417 A1 | 12/2005 | Barany et al. |
| 2006/0041385 A1 | 2/2006 | Bauer et al. |
| 2006/0046313 A1 | 3/2006 | Roth |
| 2006/0084078 A1 | 4/2006 | Zhao |
| 2006/0105352 A1 | 5/2006 | Qiao et al. |
| 2006/0154286 A1 | 7/2006 | Kong et al. |
| 2006/0188901 A1 | 8/2006 | Barnes et al. |
| 2006/0199183 A1 | 9/2006 | Valat et al. |
| 2006/0211001 A1 | 9/2006 | Yu et al. |
| 2006/0216775 A1 | 9/2006 | Burkart et al. |
| 2006/0240439 A1 | 10/2006 | Smith et al. |
| 2006/0263789 A1 | 11/2006 | Kincaid |
| 2006/0275782 A1 | 12/2006 | Gunderson et al. |
| 2006/0281109 A1 | 12/2006 | Barr Ost et al. |
| 2007/0020640 A1 | 1/2007 | McCloskey et al. |
| 2007/0020669 A1 | 1/2007 | Ericsson |
| 2007/0026430 A1 | 2/2007 | Andersen et al. |
| 2007/0054288 A1 | 3/2007 | Su et al. |
| 2007/0087360 A1 | 4/2007 | Boyd |
| 2007/0099208 A1 | 5/2007 | Drmanac et al. |
| 2007/0128624 A1 | 6/2007 | Gormley et al. |
| 2007/0128656 A1 | 6/2007 | Agrawal |
| 2007/0134723 A1 | 6/2007 | Kozlov et al. |
| 2007/0161020 A1 | 7/2007 | Luo et al. |
| 2007/0166705 A1 | 7/2007 | Milton et al. |
| 2007/0172873 A1 | 7/2007 | Brenner et al. |
| 2007/0207482 A1 | 9/2007 | Church et al. |
| 2007/0254305 A1 | 11/2007 | Paik et al. |
| 2007/0269805 A1 | 11/2007 | Hogers |
| 2008/0003586 A1 | 1/2008 | Hyde et al. |
| 2008/0009420 A1 | 1/2008 | Schroth et al. |

(56) References Cited

U.S. PATENT DOCUMENTS

| | | |
|---|---|---|
| 2008/0108082 A1 | 5/2008 | Rank et al. |
| 2008/0108804 A1 | 5/2008 | Hayashizaki et al. |
| 2008/0132429 A1 | 6/2008 | Perov et al. |
| 2008/0160580 A1 | 7/2008 | Adessi et al. |
| 2008/0220434 A1 | 9/2008 | Thomas |
| 2008/0261204 A1 | 10/2008 | Lexow |
| 2008/0286795 A1 | 11/2008 | Kawashima et al. |
| 2008/0293046 A1 | 11/2008 | Allawi et al. |
| 2009/0005252 A1 | 1/2009 | Drmanac et al. |
| 2009/0006002 A1 | 1/2009 | Honisch et al. |
| 2009/0018024 A1 | 1/2009 | Church et al. |
| 2009/0026082 A1 | 1/2009 | Rothberg et al. |
| 2009/0036323 A1 | 2/2009 | van Eijk et al. |
| 2009/0082212 A1 | 3/2009 | Williams |
| 2009/0099041 A1 | 4/2009 | Church et al. |
| 2009/0105959 A1 | 4/2009 | Braverman et al. |
| 2009/0117573 A1 | 5/2009 | Fu et al. |
| 2009/0127589 A1 | 5/2009 | Rothberg et al. |
| 2009/0155781 A1 | 6/2009 | Drmanac et al. |
| 2009/0170713 A1 | 7/2009 | van Eijk et al. |
| 2009/0202998 A1 | 8/2009 | Schlumpberger et al. |
| 2009/0233802 A1 | 9/2009 | Bignell et al. |
| 2009/0253581 A1 | 10/2009 | van Eijk et al. |
| 2009/0270273 A1 | 10/2009 | Burns et al. |
| 2009/0283407 A1 | 11/2009 | Van Eijk |
| 2009/0291854 A1 | 11/2009 | Weisinger-Mayr et al. |
| 2009/0312193 A1 | 12/2009 | Kim et al. |
| 2010/0035249 A1 | 2/2010 | Hayashizaki et al. |
| 2010/0069263 A1 | 3/2010 | Shendure et al. |
| 2010/0105052 A1 | 4/2010 | Drmanac et al. |
| 2010/0120097 A1 | 5/2010 | Matz et al. |
| 2010/0120098 A1 | 5/2010 | Grunenwald et al. |
| 2010/0129874 A1 | 5/2010 | Mitra et al. |
| 2010/0145037 A1 | 6/2010 | Brive et al. |
| 2010/0173384 A1 | 7/2010 | Johnsson et al. |
| 2010/0184618 A1 | 7/2010 | Namsaraev et al. |
| 2010/0210475 A1 | 8/2010 | Lee et al. |
| 2010/0227329 A1 | 9/2010 | Cuppens |
| 2010/0273219 A1 | 10/2010 | May et al. |
| 2011/0028685 A1 | 2/2011 | Purkayastha et al. |
| 2011/0033854 A1 | 2/2011 | Drmanac et al. |
| 2011/0045462 A1 | 2/2011 | Fu et al. |
| 2011/0059436 A1 | 3/2011 | Hardin et al. |
| 2011/0111409 A1 | 5/2011 | Sinicropi et al. |
| 2011/0152111 A1 | 6/2011 | Fan et al. |
| 2011/0245101 A1 | 10/2011 | Chee et al. |
| 2011/0245111 A1 | 10/2011 | Chee |
| 2011/0287435 A1 | 11/2011 | Grunenwald et al. |
| 2012/0021930 A1 | 1/2012 | Schoen et al. |
| 2012/0046175 A1 | 2/2012 | Rodesch et al. |
| 2012/0046178 A1 | 2/2012 | Van Den Boom et al. |
| 2012/0065081 A1 | 3/2012 | Chee |
| 2012/0135871 A1 | 5/2012 | van Eijk et al. |
| 2012/0202698 A1 | 8/2012 | van Eijk et al. |
| 2012/0202704 A1 | 8/2012 | Fan et al. |
| 2012/0220479 A1 | 8/2012 | Ericsson et al. |
| 2012/0245053 A1 | 9/2012 | Shirai et al. |
| 2012/0252702 A1 | 10/2012 | Muratani et al. |
| 2012/0258871 A1 | 10/2012 | Kozlov et al. |
| 2012/0289414 A1 | 11/2012 | Mitra et al. |
| 2012/0301925 A1 | 11/2012 | Belyaev |
| 2013/0005594 A1 | 1/2013 | Terbrueggen et al. |
| 2013/0005600 A1 | 1/2013 | Olek |
| 2013/0023433 A1 | 1/2013 | Luo et al. |
| 2013/0035239 A1 | 2/2013 | Kong et al. |
| 2013/0040842 A1 | 2/2013 | Lim et al. |
| 2013/0065768 A1 | 3/2013 | Zheng et al. |
| 2013/0079232 A1 | 3/2013 | Kain et al. |
| 2013/0171621 A1 | 7/2013 | Luo et al. |
| 2013/0244884 A1 | 9/2013 | Jacobson et al. |
| 2013/0261019 A1 | 10/2013 | Lin et al. |
| 2013/0302801 A1 | 11/2013 | Asbury et al. |
| 2013/0338042 A1 | 12/2013 | Shen et al. |
| 2014/0066318 A1 | 3/2014 | Frisen et al. |
| 2014/0121118 A1 | 5/2014 | Warner |
| 2014/0227705 A1 | 8/2014 | Vogelstein et al. |
| 2014/0270435 A1 | 9/2014 | Dunn |
| 2014/0274731 A1 | 9/2014 | Raymond et al. |
| 2014/0323330 A1 | 10/2014 | Glezer et al. |
| 2014/0342921 A1 | 11/2014 | Weiner |
| 2014/0378350 A1 | 12/2014 | Hindson et al. |
| 2015/0000854 A1 | 1/2015 | Gann-Fetter et al. |
| 2015/0292988 A1 | 10/2015 | Bharadwaj et al. |
| 2015/0344942 A1* | 12/2015 | Frisen .................. C12Q 1/6841 506/30 |
| 2016/0003812 A1 | 1/2016 | Porreca et al. |
| 2016/0019337 A1 | 1/2016 | Roberts et al. |
| 2016/0024576 A1 | 1/2016 | Chee |
| 2016/0041159 A1 | 2/2016 | Labaer et al. |
| 2016/0060687 A1 | 3/2016 | Zhu et al. |
| 2016/0108458 A1 | 4/2016 | Frei et al. |
| 2016/0122817 A1 | 5/2016 | Jarosz et al. |
| 2016/0138091 A1 | 5/2016 | Chee et al. |
| 2016/0145677 A1 | 5/2016 | Chee et al. |
| 2016/0194692 A1 | 7/2016 | Gore et al. |
| 2016/0201125 A1 | 7/2016 | Samuels et al. |
| 2016/0253584 A1 | 9/2016 | Fodor et al. |
| 2016/0289740 A1 | 10/2016 | Fu et al. |
| 2016/0298180 A1 | 10/2016 | Chee |
| 2016/0305856 A1 | 10/2016 | Boyden et al. |
| 2016/0333403 A1 | 11/2016 | Chee |
| 2016/0376642 A1 | 12/2016 | Landegren et al. |
| 2017/0009278 A1 | 1/2017 | Söderberg et al. |
| 2017/0016053 A1 | 1/2017 | Beechem et al. |
| 2017/0029875 A1 | 2/2017 | Zhang et al. |
| 2017/0058339 A1 | 3/2017 | Chee |
| 2017/0058340 A1 | 3/2017 | Chee |
| 2017/0058345 A1 | 3/2017 | Chee |
| 2017/0067096 A1 | 3/2017 | Wassie et al. |
| 2017/0088881 A1 | 3/2017 | Chee |
| 2017/0089811 A1 | 3/2017 | Tillberg et al. |
| 2017/0159109 A1 | 6/2017 | Zheng et al. |
| 2017/0166962 A1 | 6/2017 | van Eijk et al. |
| 2017/0220733 A1 | 8/2017 | Zhuang et al. |
| 2017/0233722 A1 | 8/2017 | Seelig et al. |
| 2017/0241911 A1 | 8/2017 | Rockel et al. |
| 2017/0283860 A1 | 10/2017 | Kool et al. |
| 2017/0335297 A1 | 11/2017 | Ha et al. |
| 2017/0335410 A1 | 11/2017 | Driscoll et al. |
| 2017/0342405 A1 | 11/2017 | Fu et al. |
| 2017/0349940 A1 | 12/2017 | Morin et al. |
| 2018/0051322 A1 | 2/2018 | Church et al. |
| 2018/0057873 A1 | 3/2018 | Zhou et al. |
| 2018/0080019 A1 | 3/2018 | Blainey et al. |
| 2018/0094316 A1 | 4/2018 | Oliphant et al. |
| 2018/0112261 A1 | 4/2018 | Van Driel et al. |
| 2018/0127817 A1 | 5/2018 | Borchert et al. |
| 2018/0163265 A1 | 6/2018 | Zhang et al. |
| 2018/0179591 A1 | 6/2018 | van Eijk |
| 2018/0201925 A1 | 7/2018 | Steemers et al. |
| 2018/0201980 A1 | 7/2018 | Chee et al. |
| 2018/0208967 A1 | 7/2018 | Larman et al. |
| 2018/0216161 A1 | 8/2018 | Chen et al. |
| 2018/0216162 A1 | 8/2018 | Belhocine et al. |
| 2018/0237864 A1 | 8/2018 | Imler et al. |
| 2018/0245142 A1 | 8/2018 | So et al. |
| 2018/0247017 A1 | 8/2018 | van Eijk et al. |
| 2018/0291427 A1 | 10/2018 | Edelman |
| 2018/0291439 A1 | 10/2018 | van Eijk et al. |
| 2018/0305681 A1 | 10/2018 | Jovanovich et al. |
| 2018/0312822 A1 | 11/2018 | Lee et al. |
| 2018/0320226 A1 | 11/2018 | Church et al. |
| 2018/0334670 A1 | 11/2018 | Bharadwaj et al. |
| 2019/0055594 A1 | 2/2019 | Samusik et al. |
| 2019/0064173 A1 | 2/2019 | Bharadwaj et al. |
| 2019/0071656 A1 | 3/2019 | Chang et al. |
| 2019/0085383 A1 | 3/2019 | Church et al. |
| 2019/0119735 A1 | 4/2019 | Deisseroth et al. |
| 2019/0135774 A1 | 5/2019 | Orbai |
| 2019/0145982 A1 | 5/2019 | Chee et al. |
| 2019/0161796 A1 | 5/2019 | Hauling et al. |
| 2019/0177777 A1 | 6/2019 | Chee |
| 2019/0177778 A1 | 6/2019 | Chee |
| 2019/0177789 A1 | 6/2019 | Hindson et al. |

(56) References Cited

U.S. PATENT DOCUMENTS

| | | |
|---|---|---|
| 2019/0177800 A1 | 6/2019 | Boutet et al. |
| 2019/0194709 A1 | 6/2019 | Church et al. |
| 2019/0203275 A1 | 7/2019 | Frisen et al. |
| 2019/0218276 A1 | 7/2019 | Regev et al. |
| 2019/0218608 A1 | 7/2019 | Daugharthy et al. |
| 2019/0233878 A1 | 8/2019 | Delaney et al. |
| 2019/0233880 A1 | 8/2019 | Mir |
| 2019/0249226 A1 | 8/2019 | Bent et al. |
| 2019/0262831 A1 | 8/2019 | West et al. |
| 2019/0264268 A1 | 8/2019 | Frisen et al. |
| 2019/0271028 A1 | 9/2019 | Khafizov et al. |
| 2019/0271030 A1 | 9/2019 | Chee |
| 2019/0271031 A1 | 9/2019 | Chee |
| 2019/0300943 A1 | 10/2019 | Chee et al. |
| 2019/0300944 A1 | 10/2019 | Chee et al. |
| 2019/0300945 A1 | 10/2019 | Chee et al. |
| 2019/0309353 A1 | 10/2019 | Chee |
| 2019/0309354 A1 | 10/2019 | Chee |
| 2019/0309355 A1 | 10/2019 | Chee |
| 2019/0323071 A1 | 10/2019 | Chee |
| 2019/0323088 A1 | 10/2019 | Boutet et al. |
| 2019/0330617 A1 | 10/2019 | Church et al. |
| 2019/0338353 A1 | 11/2019 | Belgrader et al. |
| 2019/0360034 A1 | 11/2019 | Zhou et al. |
| 2019/0360043 A1 | 11/2019 | Pham et al. |
| 2019/0367969 A1 | 12/2019 | Belhocine et al. |
| 2019/0367982 A1 | 12/2019 | Belhocine et al. |
| 2019/0367997 A1 | 12/2019 | Bent et al. |
| 2020/0002763 A1 | 1/2020 | Belgrader et al. |
| 2020/0010891 A1 | 1/2020 | Beechem et al. |
| 2020/0024641 A1 | 1/2020 | Nolan et al. |
| 2020/0047010 A1 | 2/2020 | Lee et al. |
| 2020/0048690 A1 | 2/2020 | Chee |
| 2020/0063191 A1 | 2/2020 | Kennedy-Darling et al. |
| 2020/0063195 A1 | 2/2020 | Chee |
| 2020/0063196 A1 | 2/2020 | Chee |
| 2020/0071751 A1 | 3/2020 | Daugharthy et al. |
| 2020/0080136 A1 | 3/2020 | Zhang et al. |
| 2020/0109443 A1 | 4/2020 | Chee |
| 2020/0123597 A1 | 4/2020 | Daniel |
| 2020/0140920 A1 | 5/2020 | Pierce et al. |
| 2020/0173985 A1 | 6/2020 | Dong et al. |
| 2020/0199565 A1 | 6/2020 | Chen et al. |
| 2020/0199572 A1 | 6/2020 | Kuersten et al. |
| 2020/0224244 A1 | 7/2020 | Nilsson et al. |
| 2020/0239874 A1 | 7/2020 | Mikkelsen |
| 2020/0239946 A1 | 7/2020 | Dewal |
| 2020/0256867 A1 | 8/2020 | Hennek et al. |
| 2020/0277663 A1 | 9/2020 | Iyer |
| 2020/0277664 A1 | 9/2020 | Frenz |
| 2020/0283852 A1 | 9/2020 | Oliphant et al. |
| 2020/0299757 A1 | 9/2020 | Chee et al. |
| 2020/0325531 A1 | 10/2020 | Chee |
| 2020/0362398 A1 | 11/2020 | Kishi et al. |
| 2020/0370095 A1 | 11/2020 | Farmer et al. |
| 2020/0399687 A1 | 12/2020 | Frisen et al. |
| 2020/0407781 A1 | 12/2020 | Schnall-Levin |
| 2021/0010068 A1 | 1/2021 | Chee et al. |
| 2021/0010070 A1 | 1/2021 | Schnall-Levin et al. |
| 2021/0017587 A1 | 1/2021 | Cai et al. |
| 2021/0095331 A1 | 4/2021 | Fan et al. |
| 2021/0115504 A1 | 4/2021 | Cai et al. |
| 2021/0123040 A1 | 4/2021 | Macosko et al. |
| 2021/0130881 A1 | 5/2021 | Cox |
| 2021/0140982 A1 | 5/2021 | Uytingco et al. |
| 2021/0155982 A1 | 5/2021 | Yin et al. |
| 2021/0158522 A1 | 5/2021 | Weisenfeld et al. |
| 2021/0172007 A1 | 6/2021 | Chee et al. |
| 2021/0189475 A1 | 6/2021 | Tentori et al. |
| 2021/0190770 A1 | 6/2021 | Delaney et al. |
| 2021/0198741 A1 | 7/2021 | Williams |
| 2021/0199660 A1 | 7/2021 | Williams et al. |
| 2021/0207202 A1 | 7/2021 | Chee |
| 2021/0214785 A1 | 7/2021 | Stoeckius |
| 2021/0222235 A1 | 7/2021 | Chee |
| 2021/0222241 A1 | 7/2021 | Bharadwaj |
| 2021/0222242 A1 | 7/2021 | Ramachandran Iyer |
| 2021/0222253 A1 | 7/2021 | Uytingco |
| 2021/0223227 A1 | 7/2021 | Stoeckius |
| 2021/0230584 A1 | 7/2021 | Mikkelsen et al. |
| 2021/0230681 A1 | 7/2021 | Patterson et al. |
| 2021/0230692 A1 | 7/2021 | Daugharthy et al. |
| 2021/0237022 A1 | 8/2021 | Bava |
| 2021/0238581 A1 | 8/2021 | Mikkelsen et al. |
| 2021/0238664 A1 | 8/2021 | Bava et al. |
| 2021/0238675 A1 | 8/2021 | Bava |
| 2021/0238680 A1 | 8/2021 | Bava |
| 2021/0247316 A1 | 8/2021 | Bava |
| 2021/0255175 A1 | 8/2021 | Chee et al. |
| 2021/0262018 A1 | 8/2021 | Bava et al. |
| 2021/0262019 A1 | 8/2021 | Alvarado Martinez et al. |
| 2021/0269864 A1 | 9/2021 | Chee |
| 2021/0270822 A1 | 9/2021 | Chee |
| 2021/0285036 A1 | 9/2021 | Yin et al. |
| 2021/0285046 A1 | 9/2021 | Chell et al. |
| 2021/0292748 A1 | 9/2021 | Frisen et al. |
| 2021/0292822 A1 | 9/2021 | Frisen et al. |
| 2021/0317510 A1 | 10/2021 | Chee et al. |
| 2021/0317524 A1 | 10/2021 | Lucero et al. |
| 2021/0324457 A1 | 10/2021 | Ramachandran Iyer et al. |
| 2021/0332424 A1 | 10/2021 | Schnall-Levin |
| 2021/0332425 A1 | 10/2021 | Pfeiffer et al. |
| 2021/0348221 A1 | 11/2021 | Chell et al. |
| 2022/0002791 A1 | 1/2022 | Frisen et al. |
| 2022/0003755 A1 | 1/2022 | Chee |
| 2022/0010367 A1 | 1/2022 | Ramachandran Iyer et al. |
| 2022/0017951 A1 | 1/2022 | Ramachandran Iyer et al. |
| 2022/0025446 A1 | 1/2022 | Shah |
| 2022/0025447 A1 | 1/2022 | Tentori et al. |
| 2022/0033888 A1 | 2/2022 | Schnall-Levin et al. |
| 2022/0049293 A1 | 2/2022 | Frenz et al. |
| 2022/0064630 A1 | 3/2022 | Bent et al. |
| 2022/0081728 A1 | 3/2022 | Williams |
| 2022/0090058 A1 | 3/2022 | Frisen et al. |
| 2022/0090175 A1 | 3/2022 | Uytingco et al. |
| 2022/0098576 A1 | 3/2022 | Dadhwal |
| 2022/0098661 A1 | 3/2022 | Chew et al. |
| 2022/0106632 A1 | 4/2022 | Galonska et al. |
| 2022/0106633 A1 | 4/2022 | Engblom et al. |
| 2022/0112486 A1 | 4/2022 | Ramachandran Iyer et al. |
| 2022/0112545 A1 | 4/2022 | Chee |
| 2022/0119869 A1 | 4/2022 | Ramachandran Iyer et al. |
| 2022/0127659 A1 | 4/2022 | Frisen et al. |
| 2022/0127666 A1 | 4/2022 | Katiraee et al. |
| 2022/0127672 A1 | 4/2022 | Stoeckius |
| 2022/0145361 A1 | 5/2022 | Frenz et al. |
| 2022/0154255 A1 | 5/2022 | Chee et al. |
| 2022/0170083 A1 | 6/2022 | Khaled et al. |
| 2022/0195422 A1 | 6/2022 | Gallant et al. |
| 2022/0195505 A1 | 6/2022 | Frisen et al. |
| 2022/0196644 A1 | 6/2022 | Chee |
| 2022/0213526 A1 | 7/2022 | Frisen et al. |
| 2022/0220544 A1 | 7/2022 | Ach et al. |
| 2022/0241780 A1 | 8/2022 | Tentori et al. |
| 2022/0267844 A1 | 8/2022 | Ramachandran Iyer et al. |
| 2022/0282329 A1 | 9/2022 | Chell et al. |
| 2022/0290217 A1 | 9/2022 | Frenz et al. |
| 2022/0290219 A1 | 9/2022 | Chee |
| 2022/0298560 A1 | 9/2022 | Frisen et al. |
| 2022/0325325 A1 | 10/2022 | Chee et al. |
| 2022/0326251 A1 | 10/2022 | Uytingco et al. |
| 2022/0333171 A1 | 10/2022 | Chee |
| 2022/0333191 A1 | 10/2022 | Mikkelsen et al. |
| 2022/0333192 A1 | 10/2022 | Uytingco |
| 2022/0333195 A1 | 10/2022 | Schnall-Levin et al. |
| 2022/0334031 A1 | 10/2022 | Delaney et al. |
| 2022/0348905 A1 | 11/2022 | Dadhwal |
| 2022/0348992 A1 | 11/2022 | Stoeckius et al. |
| 2022/0356464 A1 | 11/2022 | Kim et al. |
| 2022/0364163 A1 | 11/2022 | Stahl et al. |
| 2022/0389491 A1 | 12/2022 | Chee |
| 2022/0389503 A1 | 12/2022 | Mikkelsen et al. |
| 2022/0389504 A1 | 12/2022 | Chew et al. |
| 2022/0403455 A1 | 12/2022 | Ramachandran Iyer et al. |

(56) References Cited

U.S. PATENT DOCUMENTS

| | | |
|---|---|---|
| 2022/0404245 A1 | 12/2022 | Chell et al. |
| 2023/0002812 A1 | 1/2023 | Stoeckius et al. |
| 2023/0014008 A1 | 1/2023 | Shastry |
| 2023/0017773 A1 | 1/2023 | Kim et al. |
| 2023/0416807 A1 | 1/2023 | Chee |
| 2023/0416808 A1 | 1/2023 | Sukovich et al. |
| 2023/0033960 A1 | 2/2023 | Gallant et al. |
| 2023/0034039 A1 | 2/2023 | Shahjamali |
| 2023/0034216 A1 | 2/2023 | Bava |
| 2023/0040363 A1 | 2/2023 | Chee |
| 2023/0042088 A1 | 2/2023 | Chee |
| 2023/0042817 A1 | 2/2023 | Mignardi |
| 2023/0056549 A1 | 2/2023 | Dadhwal |
| 2023/0064372 A1 | 3/2023 | Chell et al. |
| 2023/0069046 A1 | 3/2023 | Chew et al. |
| 2023/0077364 A1 | 3/2023 | Patterson et al. |
| 2023/0080543 A1 | 3/2023 | Katiraee et al. |
| 2023/0081381 A1 | 3/2023 | Chew et al. |
| 2023/0100497 A1 | 3/2023 | Frisen et al. |
| 2023/0107023 A1 | 4/2023 | Chee |
| 2023/0111225 A1 | 4/2023 | Chew et al. |
| 2023/0113230 A1 | 4/2023 | Kim et al. |
| 2023/0126825 A1 | 4/2023 | Nagendran et al. |
| 2023/0129552 A1 | 4/2023 | Ramachandran Iyer |
| 2023/0135010 A1 | 5/2023 | Tentori et al. |
| 2023/0143569 A1 | 5/2023 | Iyer et al. |
| 2023/0145575 A1 | 5/2023 | Gallant et al. |
| 2023/0147726 A1 | 5/2023 | Hadrup et al. |
| 2023/0151412 A1 | 5/2023 | Chee |
| 2023/0159994 A1 | 5/2023 | Chee |
| 2023/0159995 A1 | 5/2023 | Iyer et al. |
| 2023/0160008 A1 | 5/2023 | Chell et al. |
| 2023/0175045 A1 | 6/2023 | Katsori et al. |
| 2023/0183785 A1 | 6/2023 | Frisen et al. |
| 2023/0194469 A1 | 6/2023 | Tentori et al. |
| 2023/0194470 A1 | 6/2023 | Kim et al. |
| 2023/0203478 A1 | 6/2023 | Kim et al. |
| 2023/0183684 A1 | 7/2023 | Gallant et al. |
| 2023/0212650 A1 | 7/2023 | Chew et al. |
| 2023/0212655 A1 | 7/2023 | Chee |
| 2023/0220368 A1 | 7/2023 | Kim |
| 2023/0220454 A1 | 7/2023 | Bent et al. |
| 2023/0220455 A1 | 7/2023 | Galonska et al. |
| 2023/0227811 A1 | 7/2023 | Dadhwal |
| 2023/0228762 A1 | 7/2023 | Uytingco et al. |
| 2023/0242973 A1 | 8/2023 | Frisen et al. |
| 2023/0242976 A1 | 8/2023 | Tentori et al. |
| 2023/0265488 A1 | 8/2023 | Gohil et al. |
| 2023/0265489 A1 | 8/2023 | Uytingco et al. |
| 2023/0265491 A1 | 8/2023 | Tentori et al. |
| 2023/0267625 A1 | 8/2023 | Tentori et al. |
| 2023/0279474 A1 | 9/2023 | Katiraee |
| 2023/0279477 A1 | 9/2023 | Kvastad et al. |
| 2023/0279481 A1 | 9/2023 | Marrache et al. |
| 2023/0287399 A1 | 9/2023 | Gallant et al. |
| 2023/0287475 A1 | 9/2023 | Chell et al. |
| 2023/0287481 A1 | 9/2023 | Katsori et al. |
| 2023/0295699 A1 | 9/2023 | Sukovich et al. |
| 2023/0295722 A1 | 9/2023 | Bharadwaj |
| 2023/0304072 A1 | 9/2023 | Gohil et al. |
| 2023/0304074 A1 | 9/2023 | Chee et al. |
| 2023/0304078 A1 | 9/2023 | Frisen et al. |
| 2023/0313279 A1 | 10/2023 | Giacomello et al. |
| 2023/0323340 A1 | 10/2023 | Dadhwal |
| 2023/0323434 A1 | 10/2023 | Yin et al. |
| 2023/0323436 A1 | 10/2023 | Chee |
| 2023/0323447 A1 | 10/2023 | Schnall-Levin et al. |
| 2023/0323453 A1 | 10/2023 | Stoeckius |
| 2023/0332138 A1 | 10/2023 | Kim et al. |
| 2023/0332211 A1 | 10/2023 | Chee |
| 2023/0332212 A1 | 10/2023 | Chew et al. |
| 2023/0332227 A1 | 10/2023 | Ramachandran Iyer |
| 2023/0332247 A1 | 10/2023 | Singh et al. |
| 2023/0351619 A1 | 11/2023 | Tentori et al. |
| 2023/0358733 A1 | 11/2023 | Chee |
| 2023/0366008 A1 | 11/2023 | Chew et al. |
| 2023/0383285 A1 | 11/2023 | Kim et al. |
| 2023/0383344 A1 | 11/2023 | Stoeckius |
| 2023/0392204 A1 | 12/2023 | Chell et al. |
| 2023/0393071 A1 | 12/2023 | Bava |
| 2023/0407404 A1 | 12/2023 | Baumgartner et al. |
| 2023/0416850 A1 | 12/2023 | Singh et al. |
| 2024/0002931 A1 | 1/2024 | Bava |
| 2024/0011081 A1 | 1/2024 | Chee |
| 2024/0011090 A1 | 1/2024 | Chew et al. |
| 2024/0018572 A1 | 1/2024 | Mignardi |
| 2024/0018575 A1 | 1/2024 | Gallant et al. |
| 2024/0018589 A1 | 1/2024 | Schnall-Levin et al. |
| 2024/0026445 A1 | 1/2024 | Ramachandran Iyer et al. |
| 2024/0033743 A1 | 2/2024 | Tentori et al. |
| 2024/0035937 A1 | 2/2024 | Cox et al. |
| 2024/0043908 A1 | 2/2024 | Chew et al. |
| 2024/0043925 A1 | 2/2024 | Bent et al. |
| 2024/0052343 A1 | 2/2024 | Gallant et al. |
| 2024/0053351 A1 | 2/2024 | Uytingco et al. |
| 2024/0060115 A1 | 2/2024 | Chee et al. |
| 2024/0067953 A1 | 2/2024 | Mikkelsen et al. |
| 2024/0068016 A1 | 2/2024 | Frisen et al. |
| 2024/0068017 A1 | 2/2024 | Lundeberg et al. |
| 2024/0076723 A1 | 3/2024 | Mignardi |
| 2024/0080346 A1 | 3/2024 | Engblom et al. |
| 2024/0084365 A1 | 3/2024 | Frisen et al. |
| 2024/0084366 A1 | 3/2024 | Chee |
| 2024/0084383 A1 | 3/2024 | Ramachandran Iyer et al. |
| 2024/0093274 A1 | 3/2024 | Frisen et al. |
| 2024/0093290 A1 | 3/2024 | Stahl et al. |
| 2024/0110228 A1 | 4/2024 | Uytingco et al. |
| 2024/0124933 A1 | 4/2024 | Chell et al. |
| 2024/0125772 A1 | 4/2024 | Delaney et al. |
| 2024/0141327 A1 | 5/2024 | Kim et al. |
| 2024/0158838 A1 | 5/2024 | Alvarado Martinez et al. |
| 2024/0175080 A1 | 5/2024 | Galonska et al. |
| 2024/0182968 A1 | 6/2024 | Bava |
| 2024/0191286 A1 | 6/2024 | Boutet et al. |
| 2024/0200121 A1 | 6/2024 | Boutet |
| 2024/0209425 A1 | 6/2024 | Yin et al. |
| 2024/0218427 A1 | 7/2024 | Sukovich et al. |
| 2024/0218432 A1 | 7/2024 | Mielinis |
| 2024/0219701 A1 | 7/2024 | Tentori et al. |
| 2024/0253036 A1 | 8/2024 | Kim et al. |
| 2024/0263218 A1 | 8/2024 | Katiraee et al. |
| 2024/0271190 A1 | 8/2024 | Stoeckius et al. |
| 2024/0271195 A1 | 8/2024 | Mikhaiel et al. |

FOREIGN PATENT DOCUMENTS

| | | |
|---|---|---|
| CN | 1537953 | 10/2004 |
| CN | 1680604 | 10/2005 |
| CN | 1749752 | 3/2006 |
| CN | 1898398 | 1/2007 |
| CN | 101142325 | 3/2008 |
| CN | 101221182 | 7/2008 |
| CN | 101522915 | 9/2009 |
| CN | 107849606 | 3/2018 |
| CN | 108949924 | 12/2018 |
| EP | 1782737 | 5/2007 |
| EP | 1910562 | 4/2008 |
| EP | 1923471 | 5/2008 |
| EP | 1929039 | 6/2008 |
| EP | 2002017 | 12/2008 |
| EP | 2292788 | 3/2011 |
| EP | 2302070 | 3/2011 |
| EP | 2580351 | 4/2013 |
| EP | 2881465 | 6/2015 |
| EP | 3013984 | 5/2016 |
| EP | 3511423 | 7/2019 |
| EP | 3541956 | 9/2019 |
| GB | 2520765 | 6/2015 |
| JP | 2007-014297 | 1/2007 |
| JP | 2007-074967 | 3/2007 |
| JP | 2009-036694 | 2/2009 |
| WO | WO 1989/010977 | 11/1989 |
| WO | WO 1991/006678 | 5/1991 |
| WO | WO 1993/004199 | 3/1993 |

(56) References Cited

FOREIGN PATENT DOCUMENTS

| | | |
|---|---|---|
| WO | WO 1995/023875 | 9/1995 |
| WO | WO 1995/025116 | 9/1995 |
| WO | WO 1995/035505 | 12/1995 |
| WO | WO 1997/031256 | 8/1997 |
| WO | WO 1998/044151 | 10/1998 |
| WO | WO 2000/017390 | 3/2000 |
| WO | WO 2000/063437 | 10/2000 |
| WO | WO 2001/006012 | 1/2001 |
| WO | WO 2001/009363 | 2/2001 |
| WO | WO 2001/012862 | 2/2001 |
| WO | WO 2001/042796 | 6/2001 |
| WO | WO 2001/046402 | 6/2001 |
| WO | WO 2001/059161 | 8/2001 |
| WO | WO 2001/090415 | 11/2001 |
| WO | WO 2001/096608 | 12/2001 |
| WO | WO 2002/040874 | 5/2002 |
| WO | WO 2002/059355 | 8/2002 |
| WO | WO 2002/059364 | 8/2002 |
| WO | WO 2002/077283 | 10/2002 |
| WO | WO 2003/002979 | 1/2003 |
| WO | WO 2003/008538 | 1/2003 |
| WO | WO 2003/010176 | 2/2003 |
| WO | WO 2003/102233 | 12/2003 |
| WO | WO 2004/015080 | 2/2004 |
| WO | WO 2004/067759 | 8/2004 |
| WO | WO 2004/081225 | 9/2004 |
| WO | WO 2005/007814 | 1/2005 |
| WO | WO 2005/010145 | 2/2005 |
| WO | WO 2005/026387 | 3/2005 |
| WO | WO 2005/042759 | 5/2005 |
| WO | WO 2005/113804 | 12/2005 |
| WO | WO 2006/020515 | 2/2006 |
| WO | WO 2006/124771 | 11/2006 |
| WO | WO 2006/137733 | 12/2006 |
| WO | WO 2007/037678 | 4/2007 |
| WO | WO 2007/041689 | 4/2007 |
| WO | WO 2007/060599 | 5/2007 |
| WO | WO 2007/073171 | 6/2007 |
| WO | WO 2007/076726 | 7/2007 |
| WO | WO 2007/139766 | 12/2007 |
| WO | WO 2007/145612 | 12/2007 |
| WO | WO 2008/069906 | 6/2008 |
| WO | WO 2008/093098 | 8/2008 |
| WO | WO 2009/032167 | 3/2009 |
| WO | WO 2009/036525 | 3/2009 |
| WO | WO 2009/137521 | 11/2009 |
| WO | WO 2009/152928 | 12/2009 |
| WO | WO 2010/019826 | 2/2010 |
| WO | WO 2010/027870 | 3/2010 |
| WO | WO 2010/126614 | 11/2010 |
| WO | WO 2010/127186 | 11/2010 |
| WO | WO 2011/008502 | 1/2011 |
| WO | WO 2011/062933 | 5/2011 |
| WO | WO 2011/068088 | 6/2011 |
| WO | WO 2011/127006 | 10/2011 |
| WO | WO 2011/155833 | 12/2011 |
| WO | WO 2012/049316 | 4/2012 |
| WO | WO 2012/061832 | 5/2012 |
| WO | WO 2012/071428 | 5/2012 |
| WO | WO 2012/129242 | 9/2012 |
| WO | WO 2012/140224 | 10/2012 |
| WO | WO 2012/142213 | 10/2012 |
| WO | WO 2012/159089 | 11/2012 |
| WO | WO 2013/123442 | 8/2013 |
| WO | WO 2013/131962 | 9/2013 |
| WO | WO 2013/138510 | 9/2013 |
| WO | WO 2013/142389 | 9/2013 |
| WO | WO 2013/150082 | 10/2013 |
| WO | WO 2013/150083 | 10/2013 |
| WO | WO 2014/044724 | 3/2014 |
| WO | WO 2014/060483 | 4/2014 |
| WO | WO 2014/071361 | 5/2014 |
| WO | WO 2014/130576 | 8/2014 |
| WO | WO 2014/144713 | 9/2014 |
| WO | WO 2014/152397 | 9/2014 |
| WO | WO 2014/210223 | 12/2014 |
| WO | WO 2014/210353 | 12/2014 |
| WO | WO 2015/031691 | 3/2015 |
| WO | WO 2015/069374 | 5/2015 |
| WO | WO 2015/117163 | 8/2015 |
| WO | WO 2015/161173 | 10/2015 |
| WO | WO 2016/044313 | 3/2016 |
| WO | WO 2016/077763 | 5/2016 |
| WO | WO 2016/138496 | 9/2016 |
| WO | WO 2016/138500 | 9/2016 |
| WO | WO 2016/162309 | 10/2016 |
| WO | WO 2016/166128 | 10/2016 |
| WO | WO 2016/168825 | 10/2016 |
| WO | WO 2016/172362 | 10/2016 |
| WO | WO 2017/019456 | 2/2017 |
| WO | WO 2017/019481 | 2/2017 |
| WO | WO 2017/075293 | 5/2017 |
| WO | WO 2017/096158 | 7/2017 |
| WO | WO 2017/143155 | 8/2017 |
| WO | WO 2017/156336 | 9/2017 |
| WO | WO 2017/184984 | 10/2017 |
| WO | WO 2017/192633 | 11/2017 |
| WO | WO 2018/023068 | 2/2018 |
| WO | WO 2018/026873 | 2/2018 |
| WO | WO 2018/045181 | 3/2018 |
| WO | WO 2018/064640 | 4/2018 |
| WO | WO 2018/085599 | 5/2018 |
| WO | WO 2018/089550 | 5/2018 |
| WO | WO 2018/091676 | 5/2018 |
| WO | WO 2018/136397 | 7/2018 |
| WO | WO 2018/136856 | 7/2018 |
| WO | WO 2018/144582 | 8/2018 |
| WO | WO 2018/175779 | 9/2018 |
| WO | WO 2018/209398 | 11/2018 |
| WO | WO 2019/023214 | 1/2019 |
| WO | WO 2019/032760 | 2/2019 |
| WO | WO 2019/068880 | 4/2019 |
| WO | WO 2019/113457 | 6/2019 |
| WO | WO 2019/126313 | 6/2019 |
| WO | WO 2019/140201 | 7/2019 |
| WO | WO 2019/165318 | 8/2019 |
| WO | WO 2019/213254 | 11/2019 |
| WO | WO 2019/213294 | 11/2019 |
| WO | WO 2019/241290 | 12/2019 |
| WO | WO 2020/028194 | 2/2020 |
| WO | WO 2020/047002 | 3/2020 |
| WO | WO 2020/047010 | 3/2020 |
| WO | WO 2020/056381 | 3/2020 |
| WO | WO 2020/076979 | 4/2020 |
| WO | WO 2020/099640 | 5/2020 |
| WO | WO 2020/112604 | 6/2020 |
| WO | WO 2020/117914 | 6/2020 |
| WO | WO 2020/123301 | 6/2020 |
| WO | WO 2020/123305 | 6/2020 |
| WO | WO 2020/123309 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/123320 | 7/2020 |
| WO | WO 2020/160044 | 8/2020 |
| WO | WO 2020/167862 | 8/2020 |
| WO | WO 2020/176788 | 9/2020 |
| WO | WO 2020/176882 | 9/2020 |
| WO | WO 2020/190509 | 9/2020 |
| WO | WO 2020/198071 | 10/2020 |
| WO | WO 2020/206285 | 10/2020 |
| WO | WO 2020/240025 | 12/2020 |
| WO | WO 2020/243579 | 12/2020 |
| WO | WO 2020/254519 | 12/2020 |
| WO | WO 2021/041974 | 3/2021 |
| WO | WO 2021/067246 | 4/2021 |
| WO | WO 2021/067514 | 4/2021 |
| WO | WO 2021/091611 | 5/2021 |
| WO | WO 2021/092433 | 5/2021 |
| WO | WO 2021/097255 | 5/2021 |
| WO | WO 2021/102003 | 5/2021 |
| WO | WO 2021/102005 | 5/2021 |

(56) References Cited

FOREIGN PATENT DOCUMENTS

| | | |
|---|---|---|
| WO | WO 2021/102039 | 5/2021 |
| WO | WO 2021/116715 | 6/2021 |
| WO | WO 2021/119320 | 6/2021 |
| WO | WO 2021/133842 | 7/2021 |
| WO | WO 2021/133845 | 7/2021 |
| WO | WO 2021/133849 | 7/2021 |
| WO | WO 2021/142233 | 7/2021 |
| WO | WO 2021/168261 | 8/2021 |
| WO | WO 2021/168278 | 8/2021 |
| WO | WO 2021/207610 | 10/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/247593 | 12/2021 |
| WO | WO 2021/252499 | 12/2021 |
| WO | WO 2021/252576 | 12/2021 |
| WO | WO 2021/252591 | 12/2021 |
| WO | WO 2021/252747 | 12/2021 |
| WO | WO 2021/263111 | 12/2021 |
| WO | WO 2022/025965 | 2/2022 |
| WO | WO 2022/060798 | 3/2022 |
| WO | WO 2022/060953 | 3/2022 |
| WO | WO 2022/061150 | 3/2022 |
| WO | WO 2022/061152 | 3/2022 |
| WO | WO 2022/087273 | 4/2022 |
| WO | WO 2022/099037 | 5/2022 |
| WO | WO 2022/103712 | 5/2022 |
| WO | WO 2022/109181 | 5/2022 |
| WO | WO 2022/132645 | 6/2022 |
| WO | WO 2022/140028 | 6/2022 |
| WO | WO 2022/147005 | 7/2022 |
| WO | WO 2022/147296 | 7/2022 |
| WO | WO 2022/164615 | 8/2022 |
| WO | WO 2022/178267 | 8/2022 |
| WO | WO 2022/198068 | 9/2022 |
| WO | WO 2022/212269 | 10/2022 |
| WO | WO 2022/221425 | 10/2022 |
| WO | WO 2022/226057 | 10/2022 |
| WO | WO 2022/015913 | 11/2022 |
| WO | WO 2022/236054 | 11/2022 |
| WO | WO 2022/243303 | 11/2022 |
| WO | WO 2022/226372 | 12/2022 |
| WO | WO 2022/256503 | 12/2022 |
| WO | WO 2022/271820 | 12/2022 |
| WO | WO 2023/287765 | 1/2023 |
| WO | WO 2023/018799 | 2/2023 |
| WO | WO 2023/034489 | 3/2023 |
| WO | WO 2023/034739 | 3/2023 |
| WO | WO 2023/044071 | 3/2023 |
| WO | WO 2023/076345 | 5/2023 |
| WO | WO 2023/086880 | 5/2023 |
| WO | WO 2023/102118 | 6/2023 |
| WO | WO 2023/122033 | 6/2023 |
| WO | WO 2023/150098 | 8/2023 |
| WO | WO 2023/150163 | 8/2023 |
| WO | WO 2023/150171 | 8/2023 |
| WO | WO 2023/215552 | 11/2023 |
| WO | WO 2023/225519 | 11/2023 |
| WO | WO 2023/229988 | 11/2023 |
| WO | WO 2023/250077 | 12/2023 |
| WO | WO 2024/015578 | 1/2024 |
| WO | WO 2024/035844 | 2/2024 |
| WO | WO 2024/081212 | 4/2024 |
| WO | WO 2024/086167 | 4/2024 |
| WO | WO 2024/086776 | 4/2024 |
| WO | WO 2024/102809 | 5/2024 |
| WO | WO 2024/137826 | 6/2024 |
| WO | WO 2024/145224 | 7/2024 |
| WO | WO 2024/145441 | 7/2024 |
| WO | WO 2024/145445 | 7/2024 |
| WO | WO 2024/145491 | 7/2024 |

OTHER PUBLICATIONS

Bibikova et al., "Quantitative gene expression profiling in formalin-fixed paraffin-embedded tissues using universal bead arrays," The American Journal of Pathology, Nov. 1, 2004, 165(5): 1799-1807.

Chen et al. "Arrayed profiling of multiple glycans on whole living cell surfaces." Analytical chemistry, Oct. 15, 2013, 85(22):11153-11158.

Choi et al., "Multiplexed detection of mRNA using porosity-tuned hydrogel microparticles," Analytical chemistry, Sep. 28, 2012, 84(21):9370-9378.

Fan et al., "A versatile assay for high-throughput gene expression profiling on universal array matrices," Genome Research, May 1, 2004, 14(5):878-885.

Sun et al., "Statistical Analysis of Spatial Expression Pattern for Spatially Resolved Transcriptomic Studies," Nature Methods, Jan. 27, 2020, 17(2): 193-200.

Svensson et al., "SpatialDE: identification of spatially variable genes," Nature Methods, May 2018, 15:343-346, 15 pages.

[No Author Listed], "Chromium Next GEM Single Cell 3' Reagent Kits v3.1—User Guide," 10x Genomics, Document No. CG000204, Nov. 2019, 58 pages.

[No Author Listed], "Chromium Next GEM Single Cell 3' Reagent Kits v3.1 (Dual Index)—User Guide," 10x Genomics, Mar. 2021, Document No. CG000315, 61 pages.

[No Author Listed], "HuSNP Mapping Assay User's Manual, " Affymetrix Part No. 90094 (Affymetrix, Santa Clara, Calif.), GeneChip, 2000, 104 pages.

[No Author Listed], "Microarray technologies have excellent possibilities in genomics-related researches," Science Tools From Amersham Pharmacia Biotech, 1998, 3(4): 8 pages (with English Translation).

[No Author Listed], "Proseek® Multiplex 96×96 User Manual," Olink Proteomics, Olink Bioscience, Uppsala, Sweden, 2017, 20 pages.

10xGenomics.com, [online], "Visium Spatial Gene Expression Reagent Kits—Tissue Optimization—User Guide," Jul. 2020, retrieved on May 25, 2021, retrieved from URL<https://assets.ctfassets.net/an68im79xiti/5UJrN0CH17rEk0UXwd19It/e54d99fb08a8f1500aba503005a04a56/CG000238_VisiumSpatialTissueOptimizationUserGuide_RevD.pdf>, 42 pages.

10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw5lee9/6a2ac61cf6388a72564eeb96bc294967/CG000238_VisiumSpatialTissueOptimizationUserGuide_Rev_A.pdf>, 46 pages.

10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/5UJrN0CH17rEk0UXwd19It/e54d99fb08a8f1500aba503005a04a56/CG000238_VisiumSpatialTissueOptimizationUserGuide_RevD.pdf>, 43 pages.

10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpd1bFVhalpexR/8baa08d9007157592b65b2cdc7130990/CG000239_VisiumSpatialGeneExpression_UserGuide_RevD.pdf>, 69 pages.

10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/3GGIfH3RWpd1bFVhalpexR/8baa08d9007157592b65b2cdc7130990/CG000239_VisiumSpatialGeneExpression_UserGuide_RevD.pdf>, 70 pages.

Adessi et al., "Solid phase DNA amplification: characterisation of primer attachment and amplification mechanisms," Nucl. Acids Res., 2000, 28(20):E87, 8 pages.

(56) References Cited

OTHER PUBLICATIONS

Adiconis et al., "Comparative analysis of RNA sequencing methods for degraded or low-input samples," Nat Methods, Jul. 2013, 10(7):623-9.
Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.
Affymetrix, "Human Genome U95Av2," Internet Citation, retrieved from the internet: on the World Wide Web affymetrix.com, retrieved on Oct. 2, 2002, 1 page.
Ahlfen et al., "Determinants of RNA quality from FFPE samples," PLoS One, Dec. 2007, 2(12):e1261, 7 pages.
Alam, "Proximity Ligation Assay (PLA)," Curr Protoc Immunol., Nov. 2018, 123(1):e58, 8 pages.
Albretsen et al., "Applications of magnetic beads with covalently attached oligonucleotides in hybridization: Isolation and detection of specific measles virus mRNA from a crude cell lysate," Anal. Biochem., 1990, 189(1):40-50.
Allawi et al., "Thermodynamics and NMR of Internal GâT Mismatches in DNA," Biochemistry, 1996, 36(34):10581-10594.
Amidzadeh et al., "Assessment of different permeabilization methods of minimizing damage to the adherent cells for detection of intracellular RNA by flow cytometry," Avicenna J Med Biotechnol., Jan. 2014, 6(1):38-46.
Andresen et al., "Helicase-dependent amplification: use in OnChip amplification and potential for point-of-care diagnostics," Expert Rev Mol Diagn., Oct. 2009, 9(7):645-650.
Appella, "Non-natural nucleic acids for synthetic biology," Current Opinion in Chemical Biology, Dec. 2009, 13(5-6): 687-696.
Aran et al., "xCell: digitally portraying the tissue cellular heterogeneity landscape," Genome Biol., Nov. 2017, 18(1):220, 14 pages.
Archer et al., "Selective and flexible depletion of problematic sequences from RNA-seq libraries at the cDNA stage," BMC Genomics, May 2014, 15(1):401, 9 pages.
Armani et al., "2D-PCR: a method of mapping DNA in tissue sections," Lab Chip, 2009, 9(24):3526-34.
Arslan et al., "Engineering of a superhelicase through conformational control (Supplementary Materials)," Science, Apr. 17, 2015, 348(6232):344-347, 18 pages.
Arslan et al., "Engineering of a superhelicase through conformational control," Science, Apr. 17, 2015, 348(6232):344-347.
Asp et al., "Spatially Resolved Transcriptomes-Next Generation Tools for Tissue Exploration," Bioessays, Oct. 2020, 42(10):e1900221, 16 pages.
Atkinson et al., "An Updated Protocol for High Throughput Plant Tissue Sectioning," Front Plant Sci, 2017, 8:1721, 8 pages.
Atkinson, "Overview of Translation: Lecture Manuscript," U of Texas, 2000, DD, pp. 6.1-6.8.
Bains et al., "A novel method for nucleic acid sequence determination," Journal of Theoretical Biology, 1988, 135(3), 303-7.
Balakrishnan et al., "Flap endonuclease 1," Annu Rev Biochem., Jun. 2013, 82:119-138.
Baner et al., "Signal amplification of padlock probes by rolling circle replication," Nucleic Acids Res., 1998, 26(22):5073-5078.
Barnes, "PCR amplification of up to 35-kb DNA with high fidelity and high yield from lambda bacteriophage templates, " Proc. Natl. Acad. Sci USA, 1994, 91(6):2216-2220.
Barnett et al., "ATAC-Me Captures Prolonged DNA Methylation of Dynamic Chromatin Accessibility Loci during Cell Fate Transitions," Mol Cell., Mar. 2020, 77(6):1350-1364.e6.
Bartosovic et al., "Single-cell CUT&Tag profiles histone modifications and transcription factors in complex tissues," Nat Biotechnol., Jul. 2021, 39(7):825-835, Abstract.
Baugh et al., "Quantitative analysis of mRNA amplification by in vitro transcription," Nucleic Acids Res., 2001, 29(5):e29, 9 pages.
Beattie et al., "Advances in genosensor research," Clin Chem., May 1995, 41(5):700-6.
Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.
Bell, "A simple way to treat PCR products prior to sequencing using ExoSAP-IT," Biotechniques, 2008, 44(6):834, 1 page.
Bentley et al., "Accurate whole human genome sequencing using reversible terminator chemistry," Nature, 2008, 456(7218):53-59.
Bergenstråhle et al., "Seamless integration of image and molecular analysis for spatial transcriptomics workflows," BMC Genomics, Jul. 2020, 21(1):482, 7 pages.
Berger et al., "Universal bases for hybridization, replication and chain termination," Nucleic Acid Res., Aug. 2000, 28(15):2911-2914.
Birney et al., "Identification and analysis of functional elements in 1% of the human genome by the ENCODE pilot project," Nature, 2007, 447(7146):799-816.
Blair et al., "Microarray temperature optimization using hybridization kinetics," Methods Mol Biol., 2009, 529:171-96.
Blanchard et al., "High-density oligonucleotide arrays," Biosensors & Bioelectronics, 1996, 11(6-7):687-690.
Blanco et al., "A practical approach to FRET-based PNA fluorescence in situ hybridization," Methods, Dec. 2010, 52(4):343-51.
Blokzijl et al., "Profiling protein expression and interactions: proximity ligation as a tool for personalized medicine," J Intern. Med., 2010, 268(3):232-245.
Blow, "Tissue Issues," Nature, 2007, 448(7156):959-962.
Bolotin et al., "MiXCR: software for comprehensive adaptive immunity profiling, " Nat Methods., May 2015, 12(5):380-1.
Borm et al., "High throughput human embryo spatial transcriptome mapping by surface transfer of tissue RNA," Abstracts Selected Talks, Single Cell Genomics mtg, (SCG2019), 2019, 1 pages (Abstract Only).
Boulé et al., "Terminal deoxynucleotidyl transferase indiscriminately incorporates ribonucleotides and deoxyribonucleotides," J Biol Chem., Aug. 2001, 276(33):31388-93.
Brandon et al., "Mitochondrial mutations in cancer," Oncogene, 2006, 25(34):4647-4662.
Brenner et al., "Gene expression analysis by massively parallel signature sequencing (MPSS) on microbead arrays," Nat. Biotech., 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-1670.
Brow, "35—The Cleavase I enzyme for mutation and polymorphism scanning," PCR Applications Protocols for Functional Genomics, 1999, pp. 537-550.
Brown et al., "Retroviral integration: structure of the initial covalent product and its precursor, and a role for the viral IN protein," Proc Natl Acad Sci USA, Apr. 1989, 86(8):2525-9.
Buenrostro et al., "Transposition of native chromatin for multimodal regulatory analysis and personal epigenomics," Nat Methods, Dec. 2013, 10(12):1213-1218.
Bullard et al., "Direct comparison of nick-joining activity of the nucleic acid ligases from bacteriophage T4," Biochem. J. 2006, 398(1):135-144.
Bunt et al., "FRET from single to multiplexed signaling events," Biophys Rev. Apr. 2017, 9(2): 119-129.
Burgess, "A space for transcriptomics," Nature Reviews Genetics, 2016, 17(8):436-7.
Burgess, "Finding structure in gene expression," Nature Reviews Genetics, 2018, 19(5):249, 1 page.
Burgess, "Spatial transcriptomics coming of age," Nat Rev Genet., Jun. 2019, 20(6):317, 1 page.
Burton et al., "Coverslip Mounted-Immersion Cycled in Situ RT-PCR for the Localization of mRNA in Tissue Sections," Biotechniques, 1998, 24(1):92-100.
Butler et al., "Integrating single-cell transcriptomic data across different conditions, technologies, and species," Nat Biotechnol., Jun. 2018, 36(5):411-420.
Caliari et al., "A practical guide to hydrogels for cell culture," Nat Methods., Apr. 2016, 13(5):405-14.
Cha et al., "Specificity, efficiency, and fidelity of PCR," Genome Res., 1993, 3(3):S18-29.

(56) References Cited

OTHER PUBLICATIONS

Chandra et al., "Cell-free synthesis-based protein microarrays and their applications," Proteomics, 2009, 5(6):717-30.

Chatterjee et al., "Mitochondrial DNA mutations in human cancer. Oncogene," 2006, 25(34):4663-4674.

Chen et al., "DNA hybridization detection in a microfluidic Channel using two fluorescently labelled nucleic acid probes, " Biosensors and Bioelectronics, 2008, 23(12):1878-1882.

Chen et al., "Efficient in situ barcode sequencing using padlock probe-based BaristaSeq," Nucleic Acids Res., 2018, 46(4): e22, 11 pages.

Chen et al., "Expansion microscopy," Science, 2015, 347(6221):543-548.

Chen et al., "Large field of view-spatially resolved transcriptomics at nanoscale resolution," bioRxiv, Jan. 19, 2021, retrieved from URL <https://www.biorxiv.org/node/1751045.abstract>, 37 pages.

Chen et al., "Nanoscale imaging of RNA with expansion microscopy," Nat Methods, Aug. 2016, 13(8):679-84.

Chen et al., "Parallel single nucleotide polymorphism genotyping by surface invasive cleavage with universal detection," Anal Chem., Apr. 2005, 77(8):2400-5.

Chen et al., "RNA imaging. Spatially resolved, highly multiplexed RNA profiling in single cells," Science, Apr. 2015, 348(6233):aaa6090, 21 pages.

Chen et al., "Spatial Transcriptomics and In Situ Sequencing to Study Alzheimer's Disease," Cell, Aug. 2020, 182(4):976-991.

Chen et al., "λCB-seq: microfluidic cell barcoding and sequencing for high-resolution imaging and sequencing of single cells," Lab Chip, Nov. 2020, 20(21):3899-3913.

Chester et al., "Dimethyl sulfoxide-mediated primer Tm reduction: a method for analyzing the role of renaturation temperature in the polymerase chain reaction," Anal Biochem, Mar. 1993, 209(2):284-90.

Cho et al., "Seq-Scope: Submicrometer-resolution spatial transcriptomics for single cell and subcellular studies," bioRxiv, Jan. 27, 2021, retrieved from URL <https://www.biorxiv.org/node/1754517.abstract>, 50 pages.

Chrisey et al., "Covalent attachment of synthetic DNA to self-assembled monolayer films," Nucleic Acids Res., Aug. 1996, 24(15):3031-9.

Ciaccio et al., "Systems analysis of EGF receptor signaling dynamics with microwestern arrays," Nat Methods, Feb. 2010, 7(2):148-55.

Codeluppi et al., "Spatial organization of the somatosensory cortex revealed by osmFISH," Nature Methods, Nov. 2018, 15:932-935.

Constantine et al., "Use of genechip high-density oligonucleotide arrays for gene expression monitoring," Life Science News, Amersham Life Science, 1998, pp. 11-14.

Corces et al., "An improved ATAC-seq protocol reduces background and enables interrogation of frozen tissues," Nat. Methods, 2017, 14(10):959-962.

Credle et al., "Multiplexed analysis of fixed tissue RNA using Ligation in situ Hybridization," Nucleic Acids Research, 2017, 45(14):e128, 9 pages.

Crosetto et al., "Spatially resolved transcriptomics and beyond," Nature Review Genetics, 2015, 16(1):57-66.

Cruz et al., "Methylation in cell-free DNA for early cancer detection," Ann Oncol., Jun. 2018, 29(6):1351-1353.

Cujec et al., "Selection of v-Abl tyrosine kinase substrate sequences from randomized peptide and cellular proteomic libraries using mRNA display," Chemistry and Biology, 2002, 9(2):253-264.

Czarnik, "Encoding methods for combinatorial chemistry," Curr Opin Chem Biol., Jun. 1997, 1(1):60-6.

Dahl et al., "Circle-to-circle amplification for precise and sensitive DNA analysis," Proc. Natl. Acad. Sci., 2004, 101(13):4548-4553.

Dalma-Weiszhausz et al., "The affymetrix GeneChip platform: an overview," Methods Enzymol., 2006, 410:3-28.

Darmanis et al., "ProteinSeq: High-Performance Proteomic Analyses by Proximity, Ligation and Next Generation Sequencing," PLos One, 2011, 6(9):e25583, 10 pages.

Daubendiek et al., "Rolling-Circle RNA Synthesis: Circular Oligonucleotides as Efficient Substrates for T7 RNA Polymerase," J. Am. Chem. Soc., 1995, 117(29):7818-7819.

Davies et al., "How best to identify chromosomal interactions: a comparison of approaches," Nat. Methods, 2017, 14(2):125-134.

Deamer et al., "Characterization of nucleic acids by Nanopore analysis," Acc Chem Res., Oct. 2002, 35(10):817-25.

Dean et al., "Comprehensive human genome amplification using multiple displacement amplification," Proc Natl. Acad. Sci. USA, 2002, 99(8):5261-66.

Dean et al., "Rapid Amplification of Plasmid and Phage DNA Using Phi29 DNA Polymerase and Multiply-Primed Rolling Circle Amplification," Genome Research, Jun. 2001, 11:1095-1099.

Deng et al., "Spatial Epigenome Sequencing at Tissue Scale and Cellular Level," BioRxiv, Mar. 2021, 40 pages.

Dressman et al., "Transforming single DNA molecules into fluorescent magnetic particles for detection and enumeration of genetic variations," Proc. Natl. Acad. Sci. USA, 2003, 100(15):8817-8822.

Drmanac et al., "CoolMPS™: Advanced massively parallel sequencing using antibodies specific to each natural nucleobase, " BioRxiv, 2020, 19 pages.

Druley et al., "Quantification of rare allelic variants from pooled genomic DNA," Nat. Methods, 2009, 6(4):263-65.

Duncan et al., "Affinity chromatography of a sequence-specific DNA binding protein using Teflon-linked oligonucleotides," Anal. Biochem., 1988, 169(1):104-108.

Eberwine, "Amplification of mRNA populations using aRNA generated from immobilized oligo(dT)-T7 primed cDNA, "BioTechniques, 1996, 20(4):584-91.

Eguiluz et al., "Multitissue array review: a chronological description of tissue array techniques, applications and procedures," Pathology Research and Practice, 2006, 202(8):561-568.

Eldridge et al., "An in vitro selection strategy for conferring protease resistance to ligand binding peptides," Protein Eng Des Sel., 2009, 22(11):691-698.

Ellington et al., "Antibody-based protein multiplex platforms: technical and operational challenges," Clin Chem, 2010, 56(2):186-193.

Eng et al., "Profiling the transcriptome with RNA SPOTs," Nat Methods., 2017, 14(12):1153-1155.

Eng et al., "Transcriptome-scale super-resolved imaging in tissues by RNA seqFISH+," Nature, Apr. 2019, 568(7751):235-239, 37 pages.

Ergin et al., "Proteomic Analysis of PAXgene-Fixed Tissues," J Proteome Res., 2010, 9(10):5188-96.

Eskicioglu et al., "Image Quality Measures and Their Performance," Computer Science, IEEE Trans. Communications, Dec. 1995, 43(12):2959-2965.

Evers et al., "The effect of formaldehyde fixation on RNA: optimization of formaldehyde adduct removal, " J Mol Diagn., May 2011, 13(3):282-8.

Faruqi et al., "High-throughput genotyping of single nucleotide polymorphisms with rolling circle amplification," BMC Genomics, Aug. 2001, 2:4, 10 pages.

Fire et al., "Rolling replication of short DNA circles, " Proc. Natl. Acad. Sci., 1995, 92(10):4641-4645.

Firestone et al., "Comparison of Autofocus Methods for automated Microscopy," Cytometry, 1991, 12:195-206.

Flanigon et al., "Multiplex protein detection with DNA readout via mass spectrometry," N. Biotechnol., 2013, 30(2):153-158.

Fluidigm, "Equivalence of Imaging Mass Cytometry and Immunofluorescence on FFPE Tissue Sections," White Paper, 2017, 12 pages.

Fodor et al., "Light-directed, spatially addressable parallel chemical synthesis," Science, 1995, 251(4995):767-773.

Forster et al., "A human gut bacterial genome and culture collection for improved metagenomic analyses, " Nature Biotechnology, 2019, 37(2):186-192.

Frese et al., "Formylglycine aldehyde Tag—protein engineering through a novel post-translational modification," ChemBioChem., 2009, 10(3):425-27.

Fu et al., "Continuous Polony Gels for Tissue Mapping with High Resolution and RNA Capture Efficiency," bioRxiv, 2021, 20 pages.

(56) References Cited

OTHER PUBLICATIONS

Fu et al., "Counting individual DNA molecules by the stochastic attachment of diverse labels, " PNAS, 2011, 108(22):9026-9031.
Fu et al., "Repeat subtraction-mediated sequence capture from a complex genome," Plant J., Jun. 2010, 62(5):898-909.
Fullwood et al., "Next-generation DNA sequencing of paired-end tags (PET) for transcriptome and genome analyses," Genome Res., 2009, 19(4):521-532.
Ganguli et al., "Pixelated spatial gene expression analysis from tissue," Nat Commun., Jan. 2018, 9(1):202, 9 pages.
Gansauge et al., "Single-stranded DNA library preparation from highly degraded DNA using T4 DNA ligase," Nucleic Acids Res., Jun. 2017, 45(10):e79, 10 pages.
Gao et al., "A highly homogeneous expansion microscopy polymer composed of tetrahedron-like monomers," bioRxiv, Oct. 22, 2019, 23 pages (Preprint).
Gao et al., "Q&A: Expansion microscopy," BMC Biology, 15:50, 9 pages, 2017.
Gene@arrays[online], BeadArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.
Gerard et al., "Excess dNTPs minimize RNA hydrolysis during reverse transcription," Biotechniques, Nov. 2002, 33(5):984, 986, 988, 990.
Geusebroek et al., "Robust Autofocusing in Microscopy," Cytometry, Jan. 1, 2000, 39(1):1-9.
Gilar et al., "Study of phosphorothioate-modified oligonucleotide resistance to 3'-exonuclease using capillary electrophoresis," J Chromatogr B Biomed Sci Appl., Aug. 28, 1998, 714(1):13-20.
Gill et al., "Nucleic acid isothermal amplification technologies: a review," Nucleosides Nucleotides Nucleic Acids, Mar. 2008, 27(3):224-43.
Glass et al., "SIMPLE: a sequential immunoperoxidase labeling and erasing method," J. Histochem. Cytochem., Oct. 2009, 57(10):899-905.
Gloor, "Gene targeting in Drosophila, " Methods Mol Biol., 2004, 260:97-114.
Gnanapragasam, "Unlocking the molecular archive: the emerging use of formalin-fixed paraffin-embedded tissue for biomarker research in urological cancer," BJU International, 2009, 105(2):274-278.
Goh et al., "Highly Specific Multiplexed RNA Imaging In Tissues With Split-FISH," Nat Methods, Jun. 15, 2020, 17(7):689-693, 21 pages.
Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Goldmeyer et al., "Development of a novel one-tube isothermal reverse transcription thermophilic helicase-dependent amplification platform for rapid RNA detection," Journal of Molecular Diagnostics, American Society for Investigative Pathology and the Association for Molecular Pathology, Nov. 1, 2007, 9(5):639-644.
Goransson et al., "A single molecule array for digital targeted molecular analyses," Nucleic Acids Res., Nov. 25, 2009, 37(1):e7, 9 pages.
Goryshin et al., "Tn5 in vitro transposition," J Biol Chem., Mar. 1998, 273(13):7367-74.
Gracia Villacampa et al., "Genome-wide Spatial Expression Profiling in FFPE Tissues," bioRxiv, 2020, pp. 38 pages.
Groelz et al., "Impact of storage conditions on the quality of nucleic acids in paraffin embedded tissues," PLoS One, Sep. 2018, 13(9):e0203608, 16 pages.
Grokhovsky, "Specificity of DNA cleavage by ultrasound," Molecular Biology, 2006, 40(2):276-283.
Grünweller et al., "Locked Nucleic Acid Oligonucleotides," BioDrugs, Jul. 2007, 21(4): 235-243.
Gu et al., "Multiplex single-molecule interaction profiling of DNA-barcoded proteins," Nature, Sep. 21, 2014, 515:554-557.
Gu et al., "Protein tag-mediated conjugation of oligonucleotides to recombinant affinity binders for proximity ligation," N Biotechnol., 2013, 30(2): 144-152.
Gunderson et al., "Decoding randomly ordered DNA arrays," Genome Research, 2004, 14(5):870-877.
Guo et al., "Direct fluorescence analysis of genetic polymorphisms by hybridization with oligonucleotide arrays on glass supports," Nucleic Acids Res., Dec. 1994, 22(24):5456-65.
Guo et al., "RNA Sequencing of Formalin-Fixed, Paraffin-Embedded Specimens for Gene Expression Quantification and Data Mining," Int J Genomics, 2016, 2016:9837310, 11 pages.
Gupta et al., "Single-cell isoform RNA sequencing characterizes isoforms in thousands of cerebellar cells," Nature Biotechnol., Oct. 2018, 36:1197-1202.
Hafner et al., "Identification of microRNAs and other small regulatory RNAs using cDNA library sequencing," Methods, Jan. 2008, 44(1):3-12.
Hahnke et al., "Striptease on glass: validation of an improved stripping procedure for in situ microarrays," J Biotechnol., Jan. 2007, 128(1):1-13.
Hamaguchi et al., "Direct reverse transcription-PCR on oligo(dT)-immobilized polypropylene microplates after capturing total mRNA from crude cell lysates," Clin Chem., Nov. 1998, 44(11):2256-63.
Hanauer et al., "Separation of nanoparticles by gel electrophoresis according to size and shape," Nano Lett., Sep. 2007, 7(9):2881-5.
Hardenbol et al., "Highly multiplexed molecular inversion probe genotyping: over 10,000 targeted SNPs genotyped in a single tube assay," Genome Res., Feb. 2005, 15(2):269-75.
Hardenbol et al., "Multiplexed genotyping with sequence-tagged molecular inversion probes," Nature Biotechnol., Jun. 2003, 21(6):673-678.
Hayes et al., "Electrophoresis of proteins and nucleic acids: I-Theory," BMJ, Sep. 1989, 299(6703):843-6.
He et al., "In situ synthesis of protein arrays," Current Opinion in Biotechnology, 2008, 19(1):4-9.
He et al., "Printing protein arrays from DNA arrays," Nature Methods, 2008, 5(2):175-77.
He, "Cell-free protein synthesis: applications in proteomics and biotechnology," New Biotechnology, 2008, 25(2-3):126-132.
Healy, "Nanopore-based single-molecule DNA analysis," Nanomedicine (Lond), Aug. 2007, 2(4):459-81.
Hejatko et al., "In situ hybridization technique for mRNA detection in whole mount Arabidopsis samples," Nature Protocols, 2006, 1(4):1939-1946.
Helmli et al., "Adaptive Shape from Focus with An Error Estimation in Light Microscopy," IEEE Conference Publication, ISPA, Jun. 19, 2001, 6 pages.
Hessner et al., "Genotyping of factor V G1691A (Leiden) without the use of PCR by invasive cleavage of oligonucleotide probes," Clin Chem., Aug. 2000, 46(8 Pt 1):1051-6.
Hiatt et al., "Parallel, tag-directed assembly of locally derived short sequence reads," Nature Methods, 2010, 7(2):119-25.
Ho et al., "Bacteriophage T4 RNA ligase 2 (gp24.1) exemplifies a family of RNA ligases found in all phylogenetic domains," PNAS, Oct. 2002, 99(20):12709-14.
Ho et al., "Characterization of an ATP-Dependent DNA Ligase Encoded by Chlorella Virus PBCV-1," Journal of Virology, Mar. 1997, 71(3): 1931-1937.
Hoffman et al., "Formaldehyde crosslinking: a tool for the study of chromatin complexes," J Biol Chem., Oct. 2015, 290(44):26404-11.
Hsuih et al., "Novel, Ligation-Dependent PCR Assay for Detection of Hepatitis C Virus in Serum," Journal of Clinical Microbiology, Mar. 1996, 34(3):501-507.
Hu et al., "High reproducibility using sodium hydroxide-stripped long oligonucleotide DNA microarrays," Biotechniques, Jan. 2005, 38(1):121-4.
Hughes et al., "Microfluidic Western blotting," PNAS, Dec. 2012, 109(52):21450-21455.
Hycultbiotech.com, [online], "Immunohistochemistry, Paraffin" Apr. 2010, retrieved on Apr. 16, 2020, retrieved from URL<https://www.hycultbiotech.com/media/wysiwyg/Protocol_Immunohistochemistry_Paraffin_2.pdf>, 3 pages.

(56) References Cited

OTHER PUBLICATIONS

Ichikawa et al., "In vitro transposition of transposon Tn3," J Biol. Chem., Nov. 1990, 265(31):18829-32, Abstract.
Illumina.com [online], "Ribo-Zero® rRNA Removal Kit Reference Guide," Aug. 2016, retrieved on Apr. 26, 2022, retrieved from URL<https://jp.support.illumina.com/content/dam/illumina-support/documents/documentation/chemistry_documentation/ribosomal-depletion/ribo-zero/ribo-zero-reference-guide-15066012-02.pdf>, 36 pages.
Imbeaud et al., "Towards standardization of RNA quality assessment using user-independent classifiers of microcapillary electrophoresis traces," Nucleic Acids Res., Mar. 2005, 33(6):e56, 12 pages.
Jaffe et al., "qSVA framework for RNA quality correction in differential expression analysis," Proc Natl Acad Sci USA, Jul. 2017, 114(27):7130-7135.
Jamur et al., "Permeabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Jensen et al., "Zinc fixation preserves flow cytometry scatter and fluorescence parameters and allows simultaneous analysis of DNA content and synthesis, and intracellular and surface epitopes," Cytometry A., Aug. 2010, 77(8):798-804.
Jucá et al., "Effect of dimethyl sulfoxide on reverse transcriptase activity," Braz. J. Med. Biol. Res., Mar. 1995, 28(3):285-90.
Kalantari et al., "Deparaffinization of formalin-fixed paraffin-embedded tissue blocks using hot water instead of xylene," Anal Biochem., Aug. 2016, 507:71-3.
Kap et al., "Histological assessment of PAXgene tissue fixation and stabilization reagents," PLoS One, 2011, 6:e27704, 10 pages.
Kapteyn et al., "Incorporation of non-natural nucleotides into template-switching oligonucleotides reduces background and improves cDNA synthesis from very small RNA samples," BMC Genomics, Jul. 2010, 11:413, 9 pages.
Karmakar et al., "Organocatalytic removal of formaldehyde adducts from RNA and DNA bases," Nature Chemistry, Aug. 3, 2015, 7(9):752-758.
Kaya-Okur et al., "CUT&Tag for efficient epigenomic profiling of small samples and single cells," Apr. 2019, 10(1):1930, 10 pages.
Ke et al., "In situ sequencing for RNA analysis in preserved tissue and cells," Nat Methods., Sep. 2013, Supplementary Materials, 29 pages.
Kennedy-Darling et al., "Measuring the Formaldehyde Protein-DNA Cross-Link Reversal Rate," Analytical Chemistry, 2014, 86(12):5678-5681.
Kent et al., "Polymerase θ is a robust terminal transferase that oscillates between three different mechanisms during end-joining" Elife, Jun. 2016, 5:e13740, 25 pages.
Khaled, "Nucleic Acid Integrity Assessment of FFPE Specimens," KTH, School of Engineering Sciences in Chemistry, Biotechnology and Health (CBH), Master Thesis, 2020, 29 pages.
Kirby et al., "Cryptic plasmids of Mycobacterium avium: Tn552 to the rescue," Mol Microbiol., Jan. 2002, 43(1): 173-86.
Kleckner et al., "Tn10 and IS10 transposition and chromosome rearrangements: mechanism and regulation in vivo and in vitro," Curr Top Microbiol Immunol., 1996, 204:49-82.
Kokkat et al., "Archived formalin-fixed paraffin-embedded (FFPE) blocks: A valuable underexploited resource for extraction of DNA, RNA, and protein," Mar. 2013, 11(2):101-6.
Korbel et al., "Paired-end mapping reveals extensive structural variation in the human genome," Science, 2007, 318(5849):420-426.
Kozlov et al., "A highly scalable peptide-based assay system for proteomics," PLoS ONE, 2012, 7(6):e37441, 10 pages.
Kozlov et al., "A method for rapid protease substrate evaluation and optimization," Comb Chem High Throughput Screen, 2006, 9(6):481-87.
Kristensen et al., "High-Throughput Methods for Detection of Genetic Variation," BioTechniques, Feb. 2001, 30(2):318-332.
Krotkov et al., "Range from Focus," 1986 IEEE Conference, Apr. 7, 1986, 3:1093-1098.
Krzywkowski et al., "Chimeric padlock and iLock probes for increased efficiency of targeted RNA detection, " RNA, Jan. 2019, 25(1):82-89.
Krzywkowski et al., "Fidelity of RNA templated end-joining by Chlorella virus DNA ligase and a novel iLock assay with improved direct RNA detection accuracy," Nucleic Acids Research, Oct. 2017, 45(18):e161, 9 pages.
Kumar et al., "Template-directed oligonucleotide strand ligation, covalent intramolecular DNA circularization and catenation using click chemistry," J Am Chem Soc., May 2007, 129(21):6859-64.
Kurz et al., "cDNA—protein fusions: covalent protein—gene conjugates for the in vitro selection of peptides and proteins," ChemBioChem., 2001, 2(9):666-72.
Kwok, "High-throughput genotyping assay approaches," Pharmocogenomics, Feb. 2000, 1(1):95-100.
Lage et al., "Whole genome analysis of genetic alterations in small DNA samples using hyperbranched strand displacement amplification and array-CGH," Genome Research, 2003, 13(2):294-307.
Lahiani et al., "Enabling Histopathological Annotations on Immunofluorescent Images through Virtualization of Hematoxylin and Eosin," J Pathol Inform., Feb. 2018, 9:1, 8 pages.
Lampe et al., "A purified mariner transposase is sufficient to mediate transposition in vitro," EMBO J., Oct. 1996, 15(19):5470-9.
Landegren et al., "Reading bits of genetic information: methods for single-nucleotide polymorphism analysis," Genome Res., Aug. 1998, 8(8):769-76.
Langdale et al., "A rapid method of gene detection using DNA bound to Sephacryl," Gene, 1985, 36(3):201-210.
Larman et al., "Sensitive, multiplex and direct quantification of RNA sequences using a modified RASL assay," Nucleic Acids Research, 2014, 42(14):9146-9157.
Lee et al., "Fluorescent in situ sequencing (FISSEQ) of RNA for gene expression profiling in intact cells and tissues," Nature Protocols, 2015, 10(3):442-458.
Lee et al., "Improving the efficiency of genomic loci capture using oligonucleotide arrays for high throughput resequencing," BMC Genomics, Dec. 2009, 10:646, 12 pages.
Lee et al., "Reduced Energy Measure Ratio for Robust Autofocusing in Digital Camera," IEEE Signal Processing Letters, Feb. 2009, 16(2):133-136.
Leriche et al., "Cleavable linkers in chemical biology," Bioorganic & Medicinal Chemistry, 2012, 20:571-582.
Li et al., "A new GSH-responsive prodrug of 5-aminolevulinic acid for photodiagnosis and photodynamic therapy of tumors," European Journal of Medicinal Chemistry, Nov. 2019, 181:111583, 9 pages.
Li et al., "A photocleavable fluorescent nucleotide for DNA sequencing and analysis," Proc. Natl. Acad. Sci., 2003, 100(2):414-419.
Li et al., "An activity-dependent proximity ligation platform for spatially resolved quantification of active enzymes in single cells," Nat Commun, Nov. 2017, 8(1):1775, 12 pages.
Li et al., "RASL-seq for Massively Parallel and Quantitative Analysis of Gene Expression," Curr Protoc Mol Biol., Apr. 2012, 4(13):1-10.
Li et al., "Review: a comprehensive summary of a decade development of the recombinase polymerase amplification," Analyst, Dec. 2018, 144(1):31-67.
Lin et al., "Highly multiplexed imaging of single cells using a high-throughput cyclic immunofluorescence method," Nat Commun., Sep. 2015, 6:8390, 7 pages.
Linnarsson, "Recent advances in DNA sequencing methods—general principles of sample preparation," Experimental Cell Research, 2010, 316(8):1339-1343.
Liu et al., "High-Spatial-Resolution Multi-Omics Atlas Sequencing of Mouse Embryos via Deterministic Barcoding in Tissue," BioRxiv, 2019, 55 pages.
Liu et al., "High-Spatial-Resolution Multi-Omics Sequencing via Deterministic Barcoding in Tissue," Cell, Nov. 13, 2020, 183(6):1665-1681, 36 pages.

(56) References Cited

OTHER PUBLICATIONS

Liu et al., "Spatial transcriptome sequencing of FFPE tissues at cellular level," bioRxiv 788992, Oct. 14, 2020, 39 pages.
Lizardi et al., "Mutation detection and single-molecule counting using isothermal rolling-circle amplification," Nat. Genet., 1998, 19(3):225-232.
Lou et al., "A review of room temperature storage of biospecimen tissue and nucleic acids for anatomic pathology laboratories and biorepositories," Clin Biochem., Mar. 2014, 47(4-5):267-73.
Lovatt et al., "Transcriptome in vivo analysis (TIVA) of spatially defined single cells in live tissue," Nature Methods, 2013, 11(2):190-196.
Lund et al., "Assessment of methods for covalent binding of nucleic acids to magnetic beads, Dynabeads, and the characteristics of the bound nucleic acids in hybridization reactions," Nucleic Acids Res., 1988, 16(22):10861-80.
Lundberg et al., "High-fidelity amplification using a thermostable DNA polymerase isolated from Pyrococcus furiosus, " Gene, 1991, 108(1):1-6.
Lundberg et al., "Homogeneous antibody-based proximity extension assays provide sensitive and specific detection of low-abundant proteins in human blood," Nucleic Acids Res., 2011, 39(15):e102, 8 pages.
Lundberg et al., "Multiplexed homogeneous proximity ligation assays for high-throughput protein biomarker research in serological material," Mol Cell Proteomics, 2011, 10(4):M110.004978, 11 pages.
Lundin et al., "Increased throughput by parallelization of library preparation for massive sequencing," PLoS One, Apr. 2010, 5(4):e10029, 7 pages.
Lyamichev et al., "Invader assay for SNP genotyping," Methods Mol Biol., 2003, 212:229-40.
Lyamichev et al., "Polymorphism identification and quantitative detection of genomic DNA by invasive cleavage of oligonucleotide probes," Nat Biotechnol., Mar. 1999, 17(3):292-6.
Lyck et al., "Immunohistochemical markers for quantitative studies of neurons and glia in human neocortex," J Histochem Cytochem, 2008, 56(3):201-21.
Lykidis et al., "Novel zinc-based fixative for high quality DNA, RNA and protein analysis," Nucleic Acids Res., Jun. 2007, 35(12):e85, 10 pages.
Ma et al., "Isothermal amplification method for next-generation sequencing," PNAS, Aug. 12, 2013, 110(35):14320-14323.
MacBeath et al., "Printing proteins as microarrays for high-throughput function determination," Science, Sep. 2000, 289(5485):1760-1763.
MacIntyre, "Unmasking antigens for immunohistochemistry.," Br J Biomed Sci., 2001, 58(3):190-6.
Marx, "Method of the Year: spatially resolved transcriptomics," Nature Methods, 2021, 18(1):9-14.
Masuda et al., "Analysis of chemical modification of RNA from formalin-fixed samples and optimization of molecular biology applications for such samples," Nucleic Acids Research, Nov. 1999, 27(22):4436-4443.
Mathieson et al., "A Critical Evaluation of the PAXgene Tissue Fixation System: Morphology, Immunohistochemistry, Molecular Biology, and Proteomics," Am J Clin Pathol., Jul. 8, 2016, 146(1):25-40.
McCloskey et al., "Encoding PCR products with batch-stamps and barcodes," Biochem. Genet., 2007, 45(11-12):761-767.
Meers et al., "Improved CUT&RUN chromatin profiling tools," Elife, Jun. 2019, 8:e46314, 16 pages.
Merritt et al., "Multiplex digital spatial profiling of proteins and RNA in fixed tissue," Nat Biotechnol, May 2020, 38(5):586-599.
Metzker, "Sequencing technologies—the next generation," Nature Reviews Genetics, 2010, 11(1):31-46.
Miele et al., "Mapping cis- and trans-chromatin interaction networks using chromosome conformation capture (3C)," Methods Mol Biol., 2009, 464:105-21.
Mignardi et al., "Oligonucleotide gap-fill ligation for mutation detection and sequencing in situ," Nucleic Acids Research, Aug. 3, 2015, 43(22):e151, 12 pages.
Miller et al., "Basic concepts of microarrays and potential applications in clinical microbiology," Clinical Microbiology Reviews, 2009, 22(4):611-633.
Miller et al., "Chapter 11—Solid and Suspension Microarrays for Microbial Diagnostics," Methods in Microbiology, 2015, 42:395-431.
Miner et al., "Molecular barcodes detect redundancy and contamination in hairpin-bisulfite PCR," Nucleic Acids Res., Sep. 2004, 32(17):e135, 4 pages.
Minhas et al., "3D Shape from Focus and Depth Map computation Using Steerable Filters," ICIAR 2009: Image Analysis and Recognition, Jul. 2009, pp. 573-583.
Mishra et al., "Three-dimensional genome architecture and emerging technologies: looping in disease," Genome Medicine, 2017, 9(1):87, 14 pages.
Mitra et al., "Digital genotyping and haplotyping with polymerase colonies," Proc. Natl. Acad. Sci. USA, May 2003, 100(10):5926-5931.
Miura et al., "Highly efficient single-stranded DNA ligation technique improves low-input whole-genome bisulfite sequencing by post-bisulfite adaptor tagging," Nucleic Acids Res., Sep. 2019, 47(15):e85, 10 pages.
Mizusawa et al., "A bacteriophage lambda vector for cloning with BamHI and Sau3A," Gene, 1982, 20(3):317-322.
Mohsen et al., "The Discovery of Rolling Circle Amplification and Rolling Circle Transcription," Acc Chem Res., Nov. 15, 2016, 49(11):2540-2550, 25 pages.
Morlan et al., "Selective depletion of rRNA enables whole transcriptome profiling of archival fixed tissue," PLoS One, Aug. 2012, 7(8):e42882, 8 pages.
Motea et al., "Terminal deoxynucleotidyl transferase: the story of a misguided DNA polymerase," Biochim Biophys Acta., May 2010, 1804(5):1151-66.
Mueller et al., "RNA Integrity Number (RIN)-Standardization of RNA Quality Control," Agilent Technologies, 2004, 8 pages.
Mulder et al., "CapTCR-seq: hybrid capture for T-cell receptor repertoire profiling," Blood Advances, Dec. 2018, 2(23):3506-3514.
Nadji et al., "Immunohistochemistry of tissue prepared by a molecular-friendly fixation and processing system," Appl Immunohistochem Mol Morphol., Sep. 2005, 13(3):277-82.
Nallur et al., "Signal amplification by rolling circle amplification on DNA microarrays," Nucleic Acids Res., Dec. 1, 2001, 29(23):e118, 9 pages.
Nanda et al. "Practical calibrations for a Real-Time Digital Omnidirectional Camera," Proceedings of CVPR, Technical Sketch, Jan. 2001, 4 pages.
Nandakumar et al., "How an RNA Ligase Discriminates RNA versus DNA Damage," Molecular Cell, 2004, 16:211-221.
Nandakumar et al., "RNA Substrate Specificity and Structure-guided Mutational Analysis of Bacteriophage T4 RNA Ligase 2," Journal of Biological Chemistry, Jul. 2004, 279(30):31337-31347.
Nayar, "Shape from Focus," CMU-RI-TR-89-27, Carnegie Mellon University, Nov. 1989, 33 pages.
Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.
Ng et al., "Gene identification signature (GIS) analysis for transcriptome characterization and genome annotation," Nature Methods, 2005, 2(2):105-111.
Nichols et al., "RNA Ligases," Curr Protoc Mol Biol., Oct. 2008, 84(1):3.15.1-3.15.4.
Niedringhaus et al., "Landscape of next-generation sequencing technologies," Anal Chem., Jun. 2011, 83(12):4327-41.
Nikiforov et al., "The use of 96-well polystyrene plates for DNA hybridization-based assays: an evaluation of different approaches to oligonucleotide immobilization," Anal Biochem, May 1995, 227(1):201-9.

(56) References Cited

OTHER PUBLICATIONS

Niklas et al., "Selective permeabilization for the high-throughput measurement of compartmented enzyme activities in mammalian cells," Anal Biochem, Sep. 2011, 416(2):218-27.
Nilsson et al., "RNA-templated DNA ligation for transcript analysis," Nucleic Acids Res., Jan. 2001, 29(2):578-81.
Nowak et al., "Entering the Postgenome Era," Science, 1995, 270(5235):368-71.
Ohtsubo et al., "Bacterial insertion sequences," Curr Top Microbiol Immunol., 1996, 204:1-26.
Olivier, "The Invader assay for SNP genotyping," Mutat. Res., Jun. 2005, 573(1-2):103-110.
Orenstein et al., "γPNA FRET Pair Miniprobes for Quantitative Fluorescent In Situ Hybridization to Telomeric DNA in Cells and Tissue," Molecules, Dec. 2, 2017, 22(12):2117, 15 pages.
Ozsolak et al., "Digital transcriptome profiling from attomole-level RNA samples," Genome Res., Apr. 2010, 20(4):519-25.
Pandey et al., "Inhibition of terminal deoxynucleotidyl transferase by adenine dinucleotides. Unique inhibitory action of Ap5A," FEBS Lett., Mar. 1987, 213(1):204-8.
Park et al., "Single cell trapping in larger microwells capable of supporting cell spreading and proliferation," Microfluid Nanofluid, 2010, 8:263-268.
Passow et al., "RNAlater and flash freezing storage methods nonrandomly influence observed gene expression in RNAseq experiments," bioRxiv, Jul. 2018, 28 pages.
PCT International Preliminary Report on Patentability in International Appln. No. PCT/US2021/016833, dated Jul. 28, 2022, 14 pages.
PCT International Search Report and Written Opinion in International Appln. No. PCT/US2021/016833, dated May 18, 2021, 18 pages.
Pech-Pacheco et al., "Diatom Autofocusing in Brightfield Microscopy: A Comparative Study," IEEE Proceedings 15th International Conference on Pattern Recognition, ICPR-2000, Sep. 3, 2000, 4 pages.
Pellestor et al., "The peptide nucleic acids (PNAs), powerful tools for molecular genetics and cytogenetics," Eur J Hum Genet., Sep. 2004, 12(9):694-700.
Pemov et al., "DNA analysis with multiplex microarray-enhanced PCR," Nucl. Acids Res., Jan. 2005, 33(2):e11, 9 pages.
Penland et al., "RNA expression analysis of formalin-fixed paraffin-embedded tumors," Laboratory Investigation, Apr. 2007, 87(4):383-391.
Penno et al., "Stimulation of reverse transcriptase generated cDNAs with specific indels by template RNA structure: retrotransposon, dNTP balance, RT-reagent usage," Nucleic Acids Res., Sep. 2017, 45(17):10143-10155.
Perler et al., "Intervening sequences in an Archaea DNA polymerase gen," Proc Natl Acad Sci USA, Jun. 1992, 89(12):5577-5581.
Perocchi et al., "Antisense artifacts in transcriptome microarray experiments are resolved by actinomycin D," Nucleic Acids Res., 2007, 35(19):e128, 7 pages.
Petterson et al., "Generations of sequencing technologies," Genomics, 2009, 93(2):105-111.
Picelli et al., "Full-length RNA-seq from single cells using Smart-seq2," Nat Protoc., Jan. 2014, 9(1):171-81.
Picelli et al., "Tn5 transposase and tagmentation procedures for massively scaled sequencing projects," Genome Res., Dec. 2014, 24(12):2033-40.
Pipenburg et al., "DNA detection using recombination proteins," PLoS Biol., Jul. 2006, 4(7):e204, 7 pages.
Plasterk, "The Tc1/mariner transposon family," Curr Top Microbiol Immunol., 1996, 204:125-43.
Plongthongkum et al., "Advances in the profiling of DNA modifications: cytosine methylation and beyond," Nature Reviews Genetics, Aug. 2014, 15(10):647-661.
Polsky-Cynkin et al., "Use of DNA immobilized on plastic and agarose supports to detect DNA by sandwich hybridization," Clin. Chem., 1985, 31(9):1438-1443.
Porreca et al., "Polony DNA sequencing," Curr Protoc Mol Biol., Nov. 2006, Chapter 7, Unit 7.8, pp. 7.8.1-7.8.22.
U.S. Appl. No. 61/267,363, filed Dec. 7, 2009, 33 pages.
Qiu et al., "Combination probes with intercalating anchors and proximal fluorophores for DNA and RNA detection," Nucleic Acids Research, Sep. 2016, 44(17):e138, 12 pages.
Raab et al., "Human tRNA genes function as chromatin insulators," EMBO J., Jan. 2012, 31(2):330-50.
Raj et al., "Imaging individual mRNA molecules using multiple singly labeled probes," Nature Methods, Oct. 2008, 5(10):877-879, 9 pages.
Ranki et al., "Sandwich hybridization as a convenient method for the detection of nucleic acids in crude samples," Gene, 1983, 21(1-2):77-85.
Reinartz et al., "Massively parallel signature sequencing (MPSS) as a tool for in-depth quantitative gene expression profiling in all organisms," Brief Funct Genomic Proteomic, Feb. 2002, 1(1):95-104.
Reznikoff, "Tn5 as a model for understanding DNA transposition," Mol Microbiol., Mar. 2003, 47(5):1199-206.
Ristic et al., "Detection of Protein-Protein Interactions and Post-translational Modifications Using the Proximity Ligation Assay: Application to the Study of the SUMO Pathway," Methods Mol. Biol., 2016, 1449:279-90.
Robinson et al., "Small-sample estimation of negative binomial dispersion, with applications to SAGE data," Biostatistics, Apr. 2008, 9(2):321-332.
Rodriques et al., "Slide-seq: A scalable technology for measuring genome-wide expression at high spatial resolution," Science, 2019, 363(6434):1463-1467.
Ronaghi et al., "A sequencing method based on real-time pyrophosphate," Science, Jul. 1998, 281(5375):363-365.
Ronaghi et al., "Real-time DNA sequencing using detection of pyrophosphate release," Analytical Biochemistry, Nov. 1996, 242(1):84-89.
Ronaghi, "Pyrosequencing sheds light on DNA sequencing," Genome Res, Jan. 2001, 11(1):3-11.
Roy et al., "Assessing long-distance RNA sequence connectivity via RNA-templated DNA-DNA ligation," eLife, 2015, 4:e03700, 21 pages.
Salmén et al., "Barcoded solid-phase RNA capture for Spatial Transcriptomics profiling in mammalian tissue sections," Nature Protocols, Oct. 2018, 13(11):2501-2534.
Santos et al., "Evaluation of Autofocus Functions in Molecular Cytogenetic Analysis," J. Microscopy, Dec. 1997, 188(3):264-272, 9 pages.
Saxonov et al., "10x Genomics, Mastering Biology to Advance Human Health," PowerPoint, 10x, 2020, 41 pages.
Schena et al., "Quantitative monitoring of gene expression patterns with a complementary DNA microarray," Science, Oct. 1995, 270(5235):467-470.
Schouten et al., "Relative quantification of 40 nucleic acid sequences by multiplex ligation-dependent probe amplification," Nucleic Acids Res., Jun. 2002, 30(12):e57, 13 pages.
Schroeder et al., "The RIN: an RNA integrity number for assigning integrity values to RNA measurements," BMC Molecular Biology, Jan. 2006, 7:3, 14 pages.
Schweitzer et al., "Immunoassays with rolling circle DNA amplification: A versatile platform for ultrasensitive antigen detection," Proc. Natl Acad. Sci. USA, May 22, 2000, 97:10113-119.
Schweitzer et al., "Multiplexed protein profiling on microarrays by rolling-circle amplification," Nature Biotechnology, Apr. 2002, 20(4):359-365.
Schwers et al., "A high-sensitivity, medium-density, and target amplification-free planar waveguide microarray system for gene expression analysis of formalin-fixed and paraffin-embedded tissue," Clin. Chem., Nov. 2009, 55(11):1995-2003.
Shalon et al., "A DNA microarray system for analyzing complex DNA samples using two-color fluorescent probe hybridization," Genome Res., Jul. 1996, 6(7):639-45.
Shelbourne et al., "Fast copper-free click DNA ligation by the ring-strain promoted alkyne-azide cycloaddition reaction," Chem. Commun., 2011, 47(22):6257-6259.

(56) References Cited

OTHER PUBLICATIONS

Shen et al., "Robust Focus Measure for Low Contrast Images," IEEE Digest of Technical Papers, International Conference on Consumer Electronics, Jan. 7, 2006, 2.3-3:69-70.
Shendure et al., "Accurate multiplex polony sequencing of an evolved bacterial genome," Science, 2005, 309(5741):1728-1732.
Shi et al., "The MicroArray Quality Control (MAQC) project shows inter- and intraplatform reproducibility of gene expression measurements," Nature Biotechnology, 2006, 24(9):1151-61.
Shirvaikar, "An Optical Measure for Camera Focus and Exposure," Proceedings of the IEEE SSST, Mar. 16, 2004, 4 pages.
Simonis et al., "Nuclear organization of active and inactive chromatin domains uncovered by chromosome conformation capture-on-chip (4C)," Nat Genet., Nov. 2006, 38(11):1348-54.
Singh et al., "High-throughput targeted long-read single cell sequencing reveals the clonal and transcriptional landscape of lymphocytes," Nat Commun., Jul. 2019, 10(1):3120, 13 pages.
Skene et al., "An efficient targeted nuclease strategy for high-resolution mapping of DNA binding sites," Elife, Jan. 2017, 6:e21856, 35 pages.
Slomovic et al., "Addition of poly(A) and poly(A)-rich tails during RNA degradation in the cytoplasm of human cells," Proc Natl Acad Sci USA, Apr. 2010, 107(16):7407-12.
Software with Metaxpress, "ImageXpress Nano Automated Imaging System," moleculardevices.com, Oct. 1, 2017, retrieved from URL <https://www.moleculardevices.com/sites/default/files/en/assets/user-guide/dd/img/imagexpress-nano- automated-imaging-system-with-metaxpress-software.pdf>, 175 pages.
Sountoulidis et al., "Scrinshot, a spatial method for single-cell resolution mapping of cell states in tissue sections, " PLoS Biol., Nov. 2020, 18(11):e3000675, 32 pages.
Spiess et al., "A highly efficient method for long-chain cDNA synthesis using trehalose and betaine," Anal. Biochem., Feb. 2002, 301(2):168-74.
Spitale et al., "Structural imprints in vivo decode RNA regulatory mechanisms," Nature, 2015, 519(7544):486-90.
Stahl et al., "Visualization and analysis of gene expression in tissue sections by spatial transcriptomics," Science, Jul. 2016, 353(6294):78-82.
Stahl et al., "Visualization and analysis of gene expression in tissue sections by spatial transcriptomics," Supplementary Materials, Science, Jul. 2016, 353(6294):78-82, 41 pages.
Stimpson et al., "Real-time detection of DNA hybridization and melting on oligonucleotide arrays by using optical wave guides," Proc Natl Acad Sci USA, Jul. 1995, 92(14):6379-83.
Stoddart et al., "Single-nucleotide discrimination in immobilized DNA oligonucleotides with a biological nanopore," PNAS USA., May 2009, 106(19):7702-7707.
Strell et al., "Placing RNA in context and space—methods for spatially resolved transcriptomics," The FEBS Journal, 2019, 286(8):1468-1481.
Stroh et al., "Quantum dots spectrally distinguish multiple species within the tumor milieu in vivo," Nat Med., Jun. 2005, 11(6):678-82.
Subbarao et al., "Focusing Techniques," SPIE Proceedings, Nov. 1, 1992, Machine Vision Applications, Architectures, and Systems Integration, 1823:163-174.
Sutherland et al., "Utility of formaldehyde cross-linking and mass spectrometry in the study of protein-protein interactions," J. Mass Spectrom., Jun. 2008, 43(6):699-715.
Takei et al., "Integrated Spatial Genomics Reveals Global Architecture of Single Nuclei," Nature, Jan. 27, 2021, 590(7845):344-350, 53 pages.
Taylor et al., "Mitochondrial DNA mutations in human disease," Nature Reviews Genetics, May 2005, 6(5):389-402.
Tentori et al., "Detection of Isoforms Differing by a Single Charge Unit in Individual Cells," Chem. Int. Ed., 2016, 55(40):12431-5.
Thelen et al., "Improvements in Shape-from-Focus for Holographic Reconstructions," IEEE Transactions on Image Processing, Jan. 2009, 18(1):151-157.
Tian et al., "Antigen peptide-based immunosensors for rapid detection of antibodies and antigens," Anal Chem, 2009, 81(13):5218-5225.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Tolbert et al., "New methods for proteomic research: preparation of proteins with N-terminal cysteines for labeling and conjugation," Angewandte Chemie International Edition, Jun. 2002, 41(12):2171-4.
Toubanaki et al., "Dry-reagent disposable biosensor for visual genotyping of single nucleotide polymorphisms by oligonucleotide ligation reaction: application to pharmacogenetic analysis," Hum Mutat., Aug. 2008, 29(8):1071-8.
Trejo et al., "Extraction-free whole transcriptome gene expression analysis of FFPE sections and histology-directed subareas of tissue, " PLoS ONE, Feb. 2019, 14(2):e0212031, 22 pages.
Tu et al., "TCR sequencing paired with massively parallel 3' RNA-seq reveals clonotypic T cell signatures," Nature Immunology, Dec. 2019, 20(12):1692-1699.
Twyman et al., "Techniques Patents for SNP Genotyping," Pharmacogenomics, Jan. 2003, 4(1):67-79.
Ulery et al., "Biomedical Applications of Biodegradable Polymers," J Polym Sci B Polym Phys., Jun. 2011, 49(12):832-864.
U.S. Appl. No. 60/416,118 Fan et al., Multiplex Nucleic Acid Analysis Using Archived or Fixed Samples, filed Oct. 3, 2002, 22 pages.
Van Gelder et al., "Amplified RNA synthesized from limited quantities of heterogeneous cDNA," Proc. Natl. Acad. Sci. USA, 1990, 87(5):1663-1667.
Vandenbroucke et al., "Quantification of splice variants using real-time PCR, " Nucleic Acids Research, 2001, 29(13):e68, 7 pages.
Vandernoot et al., "cDNA normalization by hydroxyapatite chromatography to enrich transcriptome diversity in RNA-seq applications," Biotechniques, Dec. 2012, 53(6):373-80.
Vasiliskov et al., "Fabrication of microarray of gel-immobilized compounds on a chip by copolymerization," Biotechniques, Sep. 1999, 27(3):592-606.
Vázquez Bernat et al., "High-Quality Library Preparation for NGS-Based Immunoglobulin Germline Gene Inference and Repertoire Expression Analysis," Front Immunol., Apr. 2019, 10:660, 12 pages.
Velculescu et al., "Serial analysis of gene expression," Science, Oct. 1995, 270(5235):484-7.
Vickovic et al., "High-definition spatial transcriptomics for in situ tissue profiling," Nat Methods, Oct. 2019, 16(10):987-990.
Vickovic et al., "SM-Omics: An automated Platform for High-Throughput Spatial Multi-Omics," bioRxiv, Oct. 2020, 40 pages.
Vincent et al., "Helicase-dependent isothermal DNA amplification," EMBO Rep., Aug. 2004, 5(8):795-800.
Viollet et al., "T4 Rna ligase 2 truncated active site mutants: improved tools for RNA analysis," BMC Biotechnol., Jul. 2011, 11:72, 14 pages.
Vogelstein et al., "Digital PCR," Proceedings of the National Academy of Sciences, Aug. 1999, 96(16):9236-9241.
Waichman et al., "Functional immobilization and patterning of proteins by an enzymatic transfer reaction," Analytical chemistry, 2010, 82(4):1478-85.
Walker et al., "Strand displacement amplification—an isothermal, in vitro DNA amplification technique," Nucleic Acids Research, 1992, 20(7):1691-1696.
Wang et al., "Concentration gradient generation methods based on microfluidic systems," RSC Adv., 2017, 7:29966-29984.
Wang et al., "High-fidelity mRNA amplification for gene profiling," Nature Biotechnology, Apr. 2000, 18(4):457-459.
Wang et al., "Imaging-based pooled CRISPR screening reveals regulators of lncRNA localization," Proc Natl Acad Sci USA, May 2019, 116(22):10842-10851.
Wang et al., "Optimization of Process Conditions for Infected Animal Tissues by Alkaline Hydrolysis Technology, " Procedia Environmental Sciences, 2016, 31:366-374.

(56) References Cited

OTHER PUBLICATIONS

Wang et al., "Tagmentation-based whole-genome bisulfite sequencing," Nature Protocols, Oct. 2013, 8(10):2022-2032.
Wang, "RNA amplification for successful gene profiling analysis," J Transl Med., Jul. 2005, 3:28, 11 pages.
Weinreich et al., "Evidence that the cis Preference of the Tn5 Transposase is Caused by Nonproductive Multimerization, " Genes and Development, Oct. 1994, 8(19):2363-2374.
Wiedmann et al., "Ligase chain reaction (LCR)—overview and applications," PCR Methods Appl., Feb. 1994, 3(4):S51-64.
Wilson et al., "New transposon delivery plasmids for insertional mutagenesis in Bacillus anthracis," J Microbiol Methods, Dec. 2007, 71(3):332-5.
Wohnhaas et al., "DMSO cryopreservation is the method of choice to preserve cells for droplet-based single-cell RNA sequencing, " Scientific Reports, Jul. 2019, 9(1):10699, 14 pages.
Wolf et al., "Rapid hybridization kinetics of DNA attached to submicron latex particles," Nucleic Acids Res, 1987, 15(7):2911-2926.
Wong et al., "Direct Site-Selective Covalent Protein Immobilization Catalyzed by a Phosphopantetheinyl Transferase," J. Am. Chem Soc., 2008, 130(37): 12456-64.
Woo et al., "A Comparison of cDNA, Oligonucleotide, and Affymetrix GeneChip Gene Expression Microarray Platforms," Journal of Biomolecular Techniques, 2004, 15(4), 276-284.
Worthington et al., "Cloning of random oligonucleotides to create single-insert plasmid libraries," Anal Biochem, 2001, 294(2): 169-175.
Wu et al., "Detection DNA Point Mutation with Rolling-Circle Amplification Chip," IEEE, 2010 4th International Conference on Bioinformatics and Biomedical Engineering, Jun. 2010, 4 pages.
Wu et al., "RollFISH achieves robust quantification of single-molecule RNA biomarkers in paraffin-embedded tumor tissue samples," Commun Biol., Nov. 2018, 1:209, 8 pages.
Xia et al., "Spatial transcriptome profiling by MERFISH reveals subcellular RNA compartmentalization and cell cycle-dependent gene expression", Proceedings of the National Academy of Sciences, Sep. 2019, 116(39):19490-19499.
Yang et al., "Wavelet-Based Autofocusing and Unsupervised Segmentation of Microscopic Images," IEEE Xplore Conference: Intelligent Robots and Systems, Oct. 27, 2003, 3:2143-2148.
Yasukawa et al., "Effects of organic solvents on the reverse transcription reaction catalyzed by reverse transcriptases from avian myeloblastosis virus and Moloney murine leukemia virus," Biosci Biotechnol Biochem., 2010, 74(9):1925-30.
Yeakley et al., "A trichostatin A expression signature identified by TempO-Seq targeted whole transcriptome profiling," PLoS ONE, May 2017, 12(5):e0178302, 22 pages.
Yeakley et al., "Profiling alternative splicing on fiber-optic arrays," Nature biotechnology, 2002, 20:353-358.
Yershov et al., "DNA analysis and diagnostics on oligonucleotide microchips," Proc. Natl. Acad. Sci. USA, May 1996, 93(10):4913-4918.
Yin et al., "Genetically encoded short peptide tag for versatile protein labeling by Sfp phosphopantetheinyl transferase, " PNAS, 2005, 102(44):15815-20.
Yu et al., "Shrinkage estimation of dispersion in Negative Binomial models for RNA-seq experiments with small sample size, " Bioinformatics, May 2013, 29(10):1275-1282.
Zahra et al., "Assessment of Different Permeabilization Methods of Minimizing Damage to the Adherent Cells for Detection of Intracellular RNA by Flow Cytometry, " Avicenna Journal of Medical Biotechnology, Jan. 1, 2014, 6(1):38-46.
Zhang et al., "Archaeal RNA ligase from Thermoccocus kodakarensis for template dependent ligation," RNA Biol., Jan. 2017, 14(1):36-44.
Zhang et al., "Assembling DNA through Affinity Binding to Achieve Ultrasensitive Protein Detection," Angew Chem Int Ed Engl., 2013, 52(41):10698-705.

Zhang et al., "Binding-induced DNA assembly and its application to yoctomole detection of proteins," Anal Chem, 2012, 84(2):877-884.
Zhang et al., "Genome-wide open chromatin regions and their effects on the regulation of silk protein genes in Bombyx mori," Sci Rep., Oct. 2017, 7(1): 12919, 9 pages.
Zhang et al., "Multiplex ligation-dependent probe amplification (MLPA) for ultrasensitive multiplexed microRNA detection using ribonucleotide-modified DNA probes†," Chem. Commun., 2013, 49:10013-10015.
Zhao et al., "Isothermal Amplification of Nucleic Acids," Chemical Reviews, Nov. 2015, 115(22):12491-12545.
Zhao et al., "Robustness of RNA sequencing on older formalin-fixed paraffin-embedded tissue from high-grade ovarian serous adenocarcinomas," PLoS One, May 2019, 14(5):e0216050, 23 pages.
Zheng et al., "Origins of human mitochondrial point mutations as DNA polymerase gamma-mediated errors," Mutat. Res., 2006, 599(1-2):11-20.
Zhou et al., "Genetically encoded short peptide tags for orthogonal protein labeling by Sfp and AcpS phosphopantetheinyl transferases," ACS Chemical Biol., 2007, 2(5):337-346.
Zhu et al., "Reverse transcriptase template switching: a SMART approach for full-length cDNA library construction," Biotechniques, Apr. 2001, 30(4):892-897.
10xGenomics.com, [online], "Visium Spatial Gene Expression Reagent Kits—User Guide," Jan. 2022, retrieved on Jun. 27, 2024, retrieved from URL<https://web.archive.org/web/20230326192142/https://www.10xgenomics.com/support/spatial-gene-expression-fresh-frozen/documentation/steps/library-construction/visium-spatial-gene-expression-reagent-kits-user-guide>, 71 pages.
Kuhn et al., "A novel, high-performance random array platform for quantitative gene expression profiling," Genome Res, 2004, 14:2347-2356.
Howell et al., "iFRET: An Improved Fluorescence System for DNA-Melting Analysis," Genome Research, 2002, 12:1401-1407.
Nam et al., "Nanoparticle-Based Bio-Bar Codes for the Ultrasensitive Detection of Proteins," Science, Sep. 26, 2003, 301(5641):1884-1886.
Redmond et al., "Single-cell TCRseq: paired recovery of entire T-cell alpha and beta chain transcripts in T-cell receptors from single-cell RNAseq," Genome Med, 2016, 8:80, 12 pages.
10xGenomics.com, [online], "Visium Spatial Gene Expression Reagent Kits—Tissue Optimization—User Guide," Feb. 2022, retrieved on Mar. 29, 2024, retrieved from URL<https://cdn.10xgenomics.com/image/upload/v1660261286/support-documents/CG000238_VisiumSpatialTissueOptimizationUserGuide_RevE.pdf>, 46 pages.
Asp et al., "A spatiotemporal organ-wide gene expression and cell atlas of the developing human heart," Cell, Dec. 12, 2019, 179(7):1647-1660.
Belaghzal et al., "Hi-C 2.0: An Optimized Hi-C Procedure for High-Resolution Genome-Wide Mapping of Chromosome Conformation," Methods, Jul. 1, 2017, 123:56-65, 20 pages.
Belton et al., "Hi-C: A comprehensive technique to capture the conformation of genomes," Methods, Nov. 2012, 58(3):268-276, 16 pages.
Bentzen et al., "Large-scale detection of antigen-specific T cells using peptide-MHC-I multimers labeled with DNA barcodes," Nat Biotechnol., Oct. 2016, 34(10):1037-1045, 12 pages.
Fan et al., "Illumina Universal Bead Arrays," Methods in Enzymology, 2006, 410:57-73.
Hadrup et al., "Parallel detection of antigen-specific T-cell responses by multidimensional encoding of MHC multimers," Nat. Methods., Jul. 2009, 6(7), 520-526.
Hobro et al., "An evaluation of fixation methods: Spatial and compositional cellular changes observed by Raman imaging," Vibrational Spectroscopy, Jul. 2017, 91:31-45.
Landegren et al., "A Ligase-Mediated Gene Detection Technique," Science, 1988, 241(4869):1077-1080.
Mamedov et al., "Preparing unbiased T-cell receptor and antibody cDNA libraries for the deep next generation sequencing profiling, " Frontiers in Immunol., Dec. 23, 2013, 4(456):1-10.
Oksuz et al., "Systematic evaluation of chromosome conformation capture assays," Nature Methods, Sep. 2021, 18:1046-1055.

(56) References Cited

OTHER PUBLICATIONS

Rohland et al., "Partial uracil-DNA-glycosylase treatment for screening of ancient DNA," Phil. Trans. R. Soc. B, Jan. 19, 2015, 370(1660): Jun. 24, 2013, 11 pages.

Schmidl et al., "ChIPmentation: fast, robust, low-input ChIP-seq for histones and transcription factors," Nature Methods, Oct. 2015, 12:963-965.

Su et al., "Restriction enzyme selection dictates detection range sensitivity in chromatin conformation capture-based variant-to-gene mapping approaches," bioRxiv, Dec. 15, 2020, 22 pages.

* cited by examiner

Human Kidney

Mouse Olfactory Bulb

Mouse Spleen

Human Lung

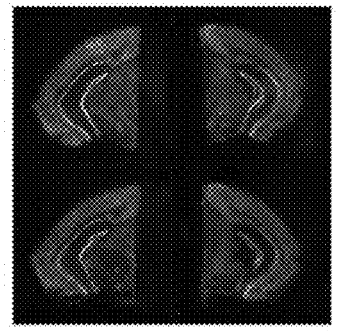 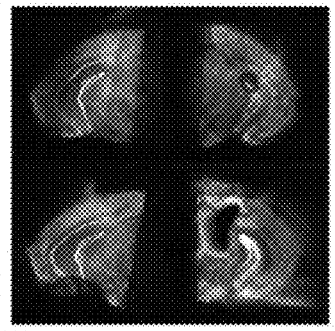 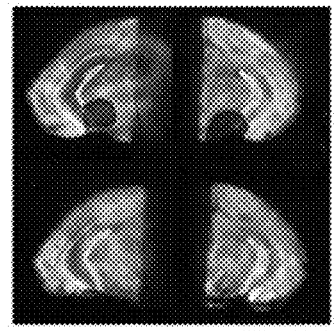
FIG. 4a        FIG. 4b        FIG. 4c
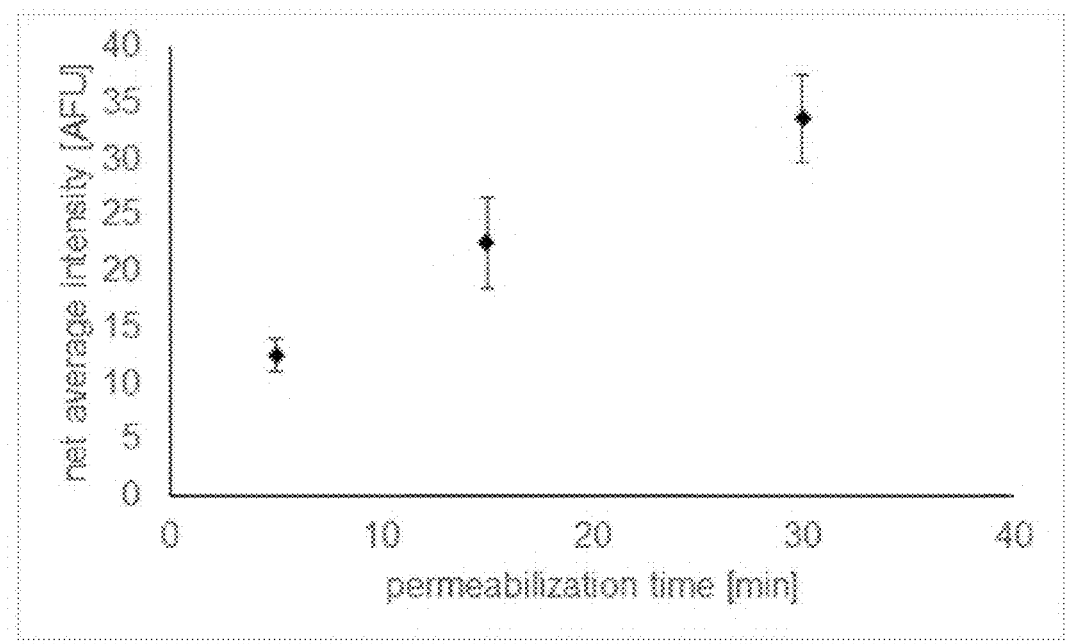
FIG. 5

FIG. 10

Region on slide

| | 1 | 2 | 3 | 4 | 5 | 6 | 7 | 8 |
|---|---|---|---|---|---|---|---|---|
| AMCO | 0.00 | 1.00 | 0.70 | 0.90 | 0.70 | 0.50 | 0.50 | 0.70 |
| BREN | 0.00 | 1.00 | 0.40 | 0.60 | 0.20 | 0.10 | 0.20 | 0.30 |
| CONTA | 0.00 | 1.00 | 0.50 | 0.70 | 0.35 | 0.20 | 0.30 | 0.35 |
| CURV | 0.00 | 1.00 | 0.45 | 0.70 | 0.20 | 0.00 | 0.10 | 0.20 |
| DCTEA | 0.00 | 1.00 | 0.50 | 0.55 | 0.10 | 0.20 | 0.50 | 0.20 |
| DCTRA | 0.00 | 1.00 | 0.90 | 0.90 | 0.55 | 0.55 | 0.80 | 0.50 |
| GDER | 0.00 | 0.70 | 0.55 | 1.00 | 0.60 | 0.20 | 0.30 | 0.55 |
| GLVA | 0.00 | 1.00 | 0.70 | 0.90 | 0.80 | 0.55 | 0.55 | 0.85 |
| GLLV | 0.00 | 0.20 | 0.30 | 0.70 | 0.90 | 0.20 | 0.65 | 0.55 |
| GLVN | 0.00 | 1.00 | 0.60 | 0.85 | 0.85 | 0.55 | 0.60 | 0.90 |
| GRAE | 0.00 | 1.00 | 0.50 | 0.75 | 0.40 | 0.20 | 0.30 | 0.35 |
| GRAT | 0.00 | 1.00 | 0.45 | 0.70 | 0.50 | 0.30 | 0.40 | 0.50 |
| GRAS | 0.00 | 1.00 | 0.50 | 0.75 | 0.30 | 0.10 | 0.30 | 0.30 |
| HELM | 0.00 | 1.00 | 0.35 | 0.40 | 0.20 | 0.10 | 0.35 | 0.10 |
| HISE | 0.00 | 1.00 | 0.90 | 0.95 | 0.70 | 0.70 | 0.70 | 0.80 |
| HISR | 0.00 | 0.90 | 0.90 | 0.90 | 0.90 | 0.60 | 0.90 | 0.90 |
| LAPE | 0.00 | 1.00 | 0.70 | 0.90 | 0.50 | 0.30 | 0.40 | 0.40 |
| LAPM | 0.00 | 1.00 | 0.50 | 0.70 | 0.40 | 0.20 | 0.20 | 0.30 |
| LAPV | 0.00 | 1.00 | 0.30 | 0.50 | 0.20 | 0.10 | 0.10 | 0.20 |
| LAPD | 0.00 | 1.00 | 0.50 | 0.70 | 0.30 | 0.20 | 0.20 | 0.35 |
| SFIL | 0.00 | 0.90 | 0.75 | 1.00 | 0.65 | 0.50 | 0.55 | 0.65 |
| SFRQ | 0.00 | 1.00 | 0.60 | 0.90 | 0.50 | 0.30 | 0.40 | 0.55 |
| TENG | 0.00 | 1.00 | 0.35 | 0.70 | 0.40 | 0.20 | 0.20 | 0.30 |
| TENV | 0.00 | 0.80 | 0.20 | 0.60 | 0.50 | 0.10 | 0.95 | 0.30 |
| VOLA | 0.00 | 1.00 | 0.35 | 0.75 | 0.30 | 0.20 | 0.35 | 0.35 |
| WAVSA | 0.00 | 1.00 | 0.50 | 0.70 | 0.40 | 0.20 | 0.20 | 0.30 |
| WAVVA | 0.00 | 1.00 | 0.20 | 0.50 | 0.10 | 0.10 | 0.10 | 0.20 |
| WAVRA | 0.00 | 1.00 | 0.35 | 0.50 | 0.50 | 0.20 | 0.40 | 0.55 |

Image Sharpness

FIG. 13

Region on slide

| | | 1 | 2 | 3 | 4 | 5 | 6 | 7 | 8 |
|---|---|---|---|---|---|---|---|---|---|
| | AMCO | 0.00 | 0.70 | 1.00 | 0.70 | 0.75 | 1.00 | 1.00 | 0.90 |
| | BREN | 0.00 | 0.50 | 1.00 | 0.45 | 0.60 | 0.80 | 0.70 | 0.50 |
| | CONTA | 0.00 | 0.75 | 1.00 | 0.60 | 0.80 | 0.80 | 0.90 | 0.80 |
| | CURV | 0.00 | 0.80 | 1.00 | 0.70 | 0.85 | 0.95 | 0.95 | 0.80 |
| | DCTEA | 0.00 | 1.00 | 1.00 | 0.40 | 0.20 | 0.30 | 0.20 | 0.00 |
| | DCTRA | 0.00 | 0.90 | 1.00 | 0.60 | 0.20 | 0.40 | 0.30 | 0.00 |
| | GDER | 0.00 | 0.40 | 1.00 | 0.55 | 0.55 | 0.95 | 0.75 | 0.60 |
| | GLVA | 0.00 | 0.60 | 1.00 | 0.70 | 0.70 | 1.00 | 1.00 | 0.75 |
| | GLLV | 0.00 | 0.10 | 0.80 | 0.35 | 0.20 | 1.00 | 0.55 | 0.30 |
| | GLVN | 0.00 | 0.60 | 1.00 | 0.55 | 0.40 | 0.70 | 0.60 | 0.40 |
| Image Sharpness | GRAE | 0.00 | 0.80 | 1.00 | 0.70 | 1.00 | 0.90 | 0.85 | 0.95 |
| | GRAT | 0.00 | 0.70 | 1.00 | 0.60 | 0.80 | 0.85 | 0.80 | 0.70 |
| | GRAS | 0.00 | 0.80 | 1.00 | 0.70 | 0.80 | 0.90 | 0.85 | 0.95 |
| | HELM | 0.20 | 0.75 | 1.00 | 0.10 | 0.10 | 0.20 | 0.10 | 0.00 |
| | HISE | 0.00 | 0.80 | 1.00 | 0.80 | 0.80 | 1.00 | 1.00 | 0.95 |
| | HISR | 0.30 | 0.00 | 0.70 | 0.55 | 0.60 | 1.00 | 0.85 | 0.80 |
| | LAPE | 0.00 | 1.00 | 1.00 | 0.70 | 0.80 | 0.80 | 0.80 | 0.85 |
| | LAPM | 0.00 | 0.80 | 1.00 | 0.55 | 0.70 | 0.80 | 0.80 | 0.70 |
| | LAPV | 0.00 | 0.55 | 1.00 | 0.40 | 0.60 | 0.75 | 0.60 | 0.50 |
| | LAPD | 0.00 | 0.80 | 1.00 | 0.55 | 0.75 | 0.80 | 0.80 | 0.75 |
| | SFIL | 0.00 | 0.60 | 1.00 | 0.70 | 0.70 | 1.00 | 0.95 | 0.70 |
| | SFRQ | 0.00 | 0.95 | 1.00 | 0.80 | 1.00 | 0.95 | 0.95 | 0.95 |
| | TENG | 0.00 | 0.50 | 1.00 | 0.50 | 0.50 | 0.80 | 0.70 | 0.50 |
| | TENV | 0.00 | 0.10 | 1.00 | 0.10 | 0.30 | 0.70 | 0.40 | 0.10 |
| | VOLA | 0.00 | 0.50 | 1.00 | 0.50 | 0.50 | 0.80 | 0.70 | 0.50 |
| | WAVSA | 0.00 | 0.55 | 1.00 | 0.55 | 0.70 | 0.75 | 0.75 | 0.70 |
| | WAVVA | 0.00 | 0.40 | 1.00 | 0.40 | 0.50 | 0.70 | 0.60 | 0.50 |
| | WAVRA | 0.00 | 0.10 | 1.00 | 0.10 | 0.40 | 0.40 | 0.30 | 0.20 |

FIG. 20

Region on slide

| | 1 | 2 | 3 | 4 | 5 | 6 | 7 | 8 |
|---|---|---|---|---|---|---|---|---|
| AMCO | 0.00 | 0.80 | 0.60 | 0.55 | 0.90 | 0.95 | 0.90 | 1.00 |
| BREN | 0.00 | 1.00 | 0.50 | 0.30 | 0.80 | 0.90 | 0.75 | 0.70 |
| CONTA | 0.00 | 1.00 | 0.60 | 0.50 | 0.80 | 0.80 | 0.80 | 0.80 |
| CURV | 0.00 | 0.95 | 0.80 | 0.75 | 0.90 | 0.95 | 0.90 | 1.00 |
| DCTEA | 0.00 | 1.00 | 0.80 | 0.60 | 0.65 | 0.60 | 0.80 | 0.75 |
| DCTRA | 0.00 | 0.70 | 0.80 | 0.70 | 0.75 | 0.70 | 1.00 | 0.80 |
| GDER | 0.00 | 0.50 | 0.55 | 0.40 | 0.80 | 0.95 | 0.95 | 1.00 |
| GLVA | 0.00 | 0.95 | 0.75 | 0.55 | 0.95 | 1.00 | 0.95 | 1.00 |
| GLLV | 0.00 | 0.50 | 0.55 | 0.00 | 0.55 | 1.00 | 0.55 | 0.50 |
| GLVN | 0.00 | 1.00 | 0.70 | 0.45 | 0.75 | 0.80 | 0.75 | 0.85 |
| GRAE | 0.00 | 1.00 | 0.60 | 0.45 | 0.95 | 0.80 | 1.00 | 1.00 |
| GRAT | 0.00 | 1.00 | 0.70 | 0.65 | 0.95 | 1.00 | 0.95 | 0.85 |
| GRAS | 0.00 | 1.00 | 0.50 | 0.45 | 0.80 | 0.80 | 0.85 | 0.90 |
| HELM | 0.00 | 0.85 | 0.95 | 0.45 | 0.50 | 1.00 | 0.50 | 0.20 |
| HISE | 0.00 | 0.95 | 0.80 | 0.80 | 1.00 | 1.00 | 1.00 | 1.00 |
| HISR | 0.00 | 1.00 | 0.75 | 0.45 | 0.70 | 0.70 | 0.55 | 0.70 |
| LAPE | 0.00 | 1.00 | 0.70 | 0.65 | 0.80 | 0.80 | 0.95 | 0.80 |
| LAPM | 0.00 | 1.00 | 0.60 | 0.45 | 0.70 | 0.70 | 0.75 | 0.70 |
| LAPV | 0.00 | 1.00 | 0.55 | 0.00 | 0.35 | 0.35 | 0.35 | 0.40 |
| LAPD | 0.00 | 1.00 | 0.60 | 0.55 | 0.70 | 0.70 | 0.75 | 0.70 |
| SFIL | 0.00 | 0.70 | 0.65 | 0.60 | 0.80 | 0.85 | 0.85 | 1.00 |
| SFRQ | 0.00 | 1.00 | 0.75 | 0.70 | 1.00 | 0.95 | 1.00 | 1.00 |
| TENG | 0.00 | 1.00 | 0.60 | 0.40 | 0.80 | 1.00 | 0.80 | 0.85 |
| TENV | 0.00 | 1.00 | 0.55 | 0.00 | 0.40 | 0.55 | 0.40 | 0.20 |
| VOLA | 0.00 | 0.80 | 0.65 | 0.55 | 0.70 | 1.00 | 0.80 | 0.90 |
| WAVSA | 0.00 | 1.00 | 0.60 | 0.40 | 0.00 | 0.60 | 0.70 | 0.80 |
| WAVVA | 0.00 | 1.00 | 0.55 | 0.35 | 0.55 | 0.55 | 0.50 | 0.55 |
| WAVRA | 0.00 | 1.00 | 0.55 | 0.20 | 0.30 | 0.35 | 0.40 | 0.30 |

Image Sharpness

FIG. 25

Region on slide

| | 1 | 2 | 3 | 4 | 5 | 6 | 7 | 8 |
|---|---|---|---|---|---|---|---|---|
| AMCO | 0.80 | 0.85 | 0.80 | 0.70 | 0.85 | 1.00 | 0.85 | 0.00 |
| BREN | 0.40 | 0.70 | 0.55 | 0.50 | 0.70 | 1.00 | 0.60 | 0.00 |
| CONTA | 0.55 | 0.80 | 0.70 | 0.70 | 0.80 | 1.00 | 0.80 | 0.00 |
| CURV | 0.25 | 0.70 | 0.55 | 0.50 | 0.70 | 1.00 | 0.60 | 0.00 |
| DCTEA | 0.20 | 0.85 | 0.90 | 0.95 | 0.35 | 0.85 | 1.00 | 0.00 |
| DCTRA | 0.25 | 1.00 | 1.00 | 1.00 | 0.55 | 0.95 | 0.95 | 0.00 |
| GDER | 0.55 | 0.80 | 0.60 | 0.55 | 0.80 | 1.00 | 0.55 | 0.00 |
| GLVA | 0.70 | 0.80 | 0.70 | 0.70 | 0.80 | 1.00 | 0.75 | 0.00 |
| GLLV | 0.25 | 0.80 | 0.40 | 0.45 | 0.70 | 1.00 | 0.40 | 0.00 |
| GLVN | 0.65 | 0.80 | 0.75 | 0.80 | 0.75 | 1.00 | 1.00 | 0.00 |
| GRAE | 0.65 | 0.80 | 0.75 | 0.75 | 0.80 | 1.00 | 0.80 | 0.00 |
| GRAT | 0.65 | 0.80 | 0.70 | 0.70 | 0.75 | 1.00 | 0.75 | 0.00 |
| GRAS | 0.65 | 0.80 | 0.75 | 0.75 | 0.80 | 1.00 | 0.80 | 0.00 |
| HELM | 0.00 | 0.60 | 0.80 | 1.00 | 0.00 | 0.55 | 0.65 | 0.00 |
| HISE | 0.80 | 0.95 | 0.80 | 0.85 | 0.95 | 1.00 | 0.80 | 0.00 |
| HISR | 0.95 | 1.00 | 0.85 | 0.95 | 0.85 | 0.90 | 0.85 | 0.00 |
| LAPE | 0.75 | 0.80 | 0.80 | 0.80 | 0.95 | 1.00 | 0.80 | 0.00 |
| LAPM | 0.60 | 0.80 | 0.70 | 0.70 | 0.80 | 1.00 | 0.70 | 0.00 |
| LAPV | 0.40 | 0.70 | 0.55 | 0.55 | 0.60 | 1.00 | 0.70 | 0.00 |
| LAPD | 0.60 | 0.80 | 0.70 | 0.70 | 0.80 | 1.00 | 0.80 | 0.00 |
| SFIL | 0.65 | 0.90 | 0.70 | 0.65 | 0.60 | 1.00 | 0.70 | 0.00 |
| SFRQ | 0.70 | 0.95 | 0.80 | 0.80 | 0.95 | 1.00 | 0.95 | 0.00 |
| TENG | 0.40 | 0.80 | 0.55 | 0.55 | 0.70 | 1.00 | 0.50 | 0.00 |
| TENV | 0.00 | 0.60 | 0.30 | 0.30 | 0.50 | 1.00 | 0.30 | 0.00 |
| VOLA | 0.40 | 0.70 | 0.55 | 0.50 | 0.60 | 1.00 | 0.55 | 0.00 |
| WAVSA | 0.55 | 0.80 | 0.70 | 0.70 | 0.80 | 1.00 | 0.90 | 0.00 |
| WAVVA | 0.40 | 0.70 | 0.55 | 0.55 | 0.60 | 1.00 | 0.90 | 0.00 |
| WAVRA | 0.30 | 0.60 | 0.55 | 0.60 | 0.40 | 0.80 | 1.00 | 0.00 |

Image Sharpness

FIG. 29

Region on slide

| | 1 | 2 | 3 | 4 | 5 | 6 | 7 | 8 |
|---|---|---|---|---|---|---|---|---|
| AMCO | 0.00 | 0.50 | 0.40 | 0.60 | 1.00 | 0.60 | 0.50 | 0.70 |
| BREN | 0.00 | 0.30 | 0.30 | 0.30 | 1.00 | 0.30 | 0.35 | 0.30 |
| CONTA | 0.00 | 0.60 | 0.30 | 0.70 | 1.00 | 0.70 | 0.60 | 0.80 |
| CURV | 0.00 | 0.80 | 0.70 | 0.90 | 1.00 | 0.80 | 0.70 | 1.00 |
| DCTEA | 0.00 | 0.40 | 0.20 | 1.00 | 0.40 | 0.35 | 0.30 | 0.60 |
| DCTRA | 0.00 | 0.50 | 0.00 | 1.00 | 0.50 | 0.20 | 0.20 | 0.60 |
| GDER | 0.00 | 0.35 | 0.20 | 0.40 | 1.00 | 0.50 | 0.35 | 0.50 |
| GLVA | 0.00 | 0.45 | 0.30 | 0.50 | 1.00 | 0.60 | 0.45 | 0.60 |
| GLLV | 0.00 | 0.10 | 0.00 | 0.10 | 1.00 | 0.40 | 0.00 | 0.00 |
| GLVN | 0.00 | 0.20 | 0.10 | 0.50 | 1.00 | 0.55 | 0.40 | 0.55 |
| GRAE | 0.00 | 0.65 | 0.55 | 0.80 | 1.00 | 0.75 | 0.65 | 1.00 |
| GRAT | 0.00 | 0.55 | 0.40 | 0.70 | 1.00 | 0.70 | 0.60 | 0.70 |
| GRAS | 0.00 | 0.55 | 0.40 | 0.80 | 1.00 | 0.80 | 0.65 | 1.00 |
| HELM | 0.40 | 0.10 | 0.00 | 0.60 | 1.00 | 0.55 | 0.40 | 0.45 |
| HISE | 0.00 | 0.80 | 0.75 | 0.80 | 1.00 | 0.80 | 0.75 | 0.95 |
| HISR | 0.50 | 0.50 | 0.00 | 0.40 | 1.00 | 0.80 | 0.50 | 0.40 |
| LAPE | 0.00 | 0.70 | 0.65 | 0.90 | 1.00 | 0.80 | 0.75 | 0.95 |
| LAPM | 0.00 | 0.65 | 0.55 | 0.70 | 1.00 | 0.70 | 0.65 | 0.80 |
| LAPV | 0.00 | 0.55 | 0.20 | 0.55 | 1.00 | 0.60 | 0.40 | 0.50 |
| LAPD | 0.00 | 0.60 | 0.55 | 0.75 | 1.00 | 0.75 | 0.70 | 0.80 |
| SFIL | 0.00 | 0.50 | 0.40 | 0.70 | 1.00 | 0.65 | 0.55 | 0.75 |
| SFRQ | 0.00 | 0.70 | 0.60 | 0.95 | 1.00 | 0.80 | 0.75 | 1.00 |
| TENG | 0.00 | 0.30 | 0.20 | 0.50 | 1.00 | 0.50 | 0.30 | 0.50 |
| TENV | 0.00 | 0.20 | 0.00 | 0.20 | 1.00 | 0.20 | 0.00 | 0.00 |
| VOLA | 0.00 | 0.30 | 0.20 | 0.20 | 1.00 | 0.30 | 0.40 | 0.50 |
| WAVSA | 0.00 | 0.55 | 0.50 | 0.70 | 1.00 | 0.70 | 0.60 | 0.70 |
| WAVVA | 0.00 | 0.30 | 0.20 | 0.20 | 1.00 | 0.20 | 0.40 | 0.50 |
| WAVRA | 0.00 | 0.30 | 0.30 | 0.80 | 1.00 | 0.60 | 0.65 | 0.65 |

Image Sharpness

Pixels within an individual spot

Pixels within an individual spot and outside the spot

QUANTITATIVE AND AUTOMATED PERMEABILIZATION PERFORMANCE EVALUATION FOR SPATIAL TRANSCRIPTOMICS

CROSS-REFERENCE TO RELATED APPLICATIONS

This application is a U.S. National Phase filing under 35 U.S.C. § 371 of International Application No. PCT/US2021/016833, filed Feb. 5, 2021, and published as WO 2021/158925 A1 on Aug. 12, 2021, which claims the benefit of priority to U.S. Provisional Application No. 62/971,711, filed Feb. 7, 2020, and to U.S. Provisional Application No. 62/989,062, filed Mar. 13, 2020, each of which is incorporated herein by reference in their entirety.

FIELD OF THE INVENTION

This invention relates to an improved method of quantifying, evaluating and optimizing permeabilization techniques used in spatial transcriptomics.

BACKGROUND OF THE INVENTION

Messenger RNA ("mRNA") is a family of RNA molecules that convey genetic information from DNA to the ribosomes, where they specify the amino acid sequence of protein products of gene expression. Spatial transcriptomics is a technology used to spatially resolve RNA-sequence data, including all mRNA's, present in individual tissue sections. Spatially barcoded reverse transcription primers are applied in ordered fashion to the surfaces of microscope slides referred to as gene expression assay slides, thus enabling the encoding and maintenance of positional information throughout the mRNA sample processing and sequencing. When a fresh-frozen tissue section is attached to the gene expression slide, the spatially barcoded primers bind and capture mRNAs from the adjacent tissue. Post mRNA capture, reverse transcription of the mRNA occurs, and the resulting cDNA library incorporates the spatial barcode and preserves spatial information. The barcoded cDNA library enables data for each mRNA transcript to be mapped back to its point of origin in the tissue section.

Permeabilization is a process of making a membrane or cell wall permeable. Permeabilization conditions can greatly affect the ability of the GEX assay slide to capture mRNAs. Permeabilization can be accomplished using surfactants or reagents that reduce the surface tension of the membrane or cell wall and/or dissolve lipids from the cell membranes, making them permeable to antibodies. Reagents include various buffers, salts, enzymes and detergents. Permeabilization can also be accomplished by selective puncture of the cell wall or membrane. When reagents are used, permeabilization is also a function of time and temperature. Higher temperatures and longer exposure times to the reagents increase the amount of permeabilization.

In order to provide access to and detect intracellular antigens, cells must first be permeabilized using a selection of reagent, time, temperature and other conditions. Typically, the conditions affecting permeabilization tend to be optimized for each type of cellular tissue, for example using a tissue optimization (TO) assay slide. The conventional tissue permeabilization assay technique enables choosing optimal conditions based on a qualitative assessment of the appearance of a fluorescent cDNA signal that results from the assay. Samples of fresh frozen tissue are placed on TO slides having six, eight, or another number of square regions that have been coated with oligonucleotide capture probes. A single tissue section is placed on each region. The tissue can optionally be treated with a fixing agent which stabilizes the tissue for the permeabilization process, optionally stained with a suitable coloring agent that amplifies the visible features of the tissue and imaged using photomicrographs. Permeabilization reagents are added to permeabilize the tissue and enable RNA from the tissue sections to hybridize to adjacent RNA-capture probes.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

The following U.S. patents and U.S. published patent applications are each incorporated by reference in their entirety into this application:

U.S. Pat. No. 9,593,365 (Ser. No. 14/434,274), issued Mar. 14, 2017 and titled, "Methods and Product for Optimising Localized or Spatial Detection of Gene expression in a Tissue Sample"; U.S. Pat. No. 10,030,261 (Ser. No. 14/111,482), issued Jul. 24, 2018 and titled, "Method and Product for Localized or Spatial Detection of Nucleic Acid in a Tissue Sample"; and U.S. Pat. No. 10,774,374 (Ser. No. 15/565,637), published Jul. 4, 2019 and titled, "Spatially Distinguished, Multiplex Nucleic Acid Analysis of Biological Specimens.

Other references listed throughout the application are incorporated by reference in their entirety.

SUMMARY OF THE INVENTION

Disclosed here are methods for optimizing permeabilization of cellular tissues for spatial transcriptomics. In some examples, the methods use a series of different permeabilization conditions (time, temperature, reagent type and concentration, etc.) for a tissue of interest. Following permeabilization, cDNA synthesis incorporating a fluorescently labelled nucleotide is performed on the tissue samples. In order to detect the cDNA that is generated, the permeabilized tissue is removed and the remaining cDNA footprint is imaged. The tissue removal is another point of optimization. Optimal permeabilization conditions result in a fluorescent cDNA footprint on the TO slide that closely resembles and preferably mirrors the tissue morphology image when the tissue is previously stained and imaged. A combination of qualitative brightness and sharpness of the fluorescence signal are used to determine the optimal conditions. Brightness is used as a proxy for the amount of transcripts captured and indicates assay sensitivity. Sharpness is used as a proxy for the resolution of the assay.

The present invention is directed to methods of optimizing the permeabilization of cellular tissues used for spatial transcriptomics. In some embodiments, the method includes the steps of:

a) selecting at least one parameter that affects permeabilization of the tissue sample;

b) preparing a plurality of sections of the tissue sample for permeabilization;
c) permeabilizing the sections of the tissue sample, wherein the permeabilization parameter is varied for the different tissue sections during permeabilization;
d) generating a cDNA footprint of each of the permeabilized tissue sections;
e) imaging the cDNA footprints;
f) determining a level of permeabilization for each tissue section by quantifying at least one image property that is determinative of the level of permeabilization; and
g) correlating the at least one image property with the variations of the permeabilization parameter to determine a value for the parameter that indicates an optimum level of the permeabilization parameter, thereby optimizing the permeabilization conditions for the tissue sample.

In some embodiments, the plurality of tissue sections comprises placing each tissue section on a separate area on a slide, wherein the slide comprises a plurality of array areas for placing tissue sections, and each array area comprising a plurality of capture probes immobilized thereon. In some embodiments, the plurality of capture probes comprise capture domains and after permeabilization analytes are released from the tissue sections and a plurality of the released analytes hybridize to the capture domains.

In some embodiments, the cDNA footprint can be generated by extending the capture domains of the capture probes using the hybridized analytes as a template to create cDNA molecules of the hybridized analytes. The capture domains can be extended enzymatically in the presence of one or more fluorescently labelled nucleotides, dATP, dCTP, dGTP or dTTP. In some embodiments, the cDNA footprint can be generated by hybridizing a primer that is complementary to the analytes hybridized to the capture domains and extending the primer enzymatically using the analytes as a template to create cDNA molecules of the hybridized analytes.

In some embodiments, the analyte can be DNA or RNA. In some embodiments, the analyte can be mRNA. In some embodiments, the capture domains comprise a poly(T) sequence, a poly(T) random sequence, a random nucleic acid sequence, a semi-random nucleic acid sequence or a non-random nucleotide sequence.

In some embodiments, the at least one parameter selected can be permeabilization time, permeabilization temperature, type of permeabilization reagent, a fixing agent used to fix the cellular tissue before permeabilization, and a staining agent used to stain the cellular tissue before permeabilization. The type of permeabilization reagent can be varied between one or more of organic solvents, cross-linking agents, detergents, enzymes, lysis reagents, and combinations thereof.

In some embodiments, the at least one image property can be image brightness, image sharpness, or both.

In some embodiments, the invention is directed to a quantitative method of optimizing the permeabilization of tissue samples used for spatial transcriptomics, comprising the steps of:
a) selecting two or more parameters that influence permeabilization in the tissue sample;
b) preparing a first plurality of sections of the tissue sample for permeabilization;
c) permeabilizing the first plurality of sections of the tissue sample, wherein the first of the two or more permeabilization parameters is varied for the different tissue sections,
d) generating a cDNA footprint of each of the first plurality of permeabilized tissue sections;
e) imaging the cDNA footprint for each of the tissue sections;
f) determining a level of permeabilization for each tissue section of the first plurality of tissue sections by quantifying at least one image property that is determinative of permeabilization;
g) correlating the at least one image property with the variations in the first parameter to determine a first value for the first parameter that yields an optimum level of permeabilization based on the first parameter;
h) preparing a second plurality of tissue sections of tissue sample for permeabilization;
i) permeabilizing the second plurality of tissue sections, wherein the second of the two permeabilization parameters is varied for the different tissue sections;
j) generating a cDNA footprint of each of the second plurality of permeabilized tissue sections;
k) imaging the cDNA footprint for each of the tissue sections;
l) determining a level of permeabilization for each tissue section of the second plurality of tissue sections by quantifying at least one image property that is determinative of permeabilization; and
m) correlating the at least one image property with the variations in the second parameter to determine a second value for the second parameter that yields an optimum level of permeabilization based on the second parameter, and based on the first and second values determine the optimal permeabilization of the tissue sample.

In some embodiments, additional tissue sections may be prepared to test additional parameters for levels of permeabilization, quantifying a relevant image property, correlating the image property with variations in the additional parameter and implementing a value for the additional parameter, along with values determined for other parameters, to optimize permeabilization of the tissue sample.

The invention may also include an instrument for quantitatively optimizing the permeabilization of tissue samples used for spatial transcriptomics, comprising:
a) an apparatus for receiving and storing data for at least one parameter that influences permeabilization in the tissue sample;
b) an apparatus for correlating variations in the at least one parameter with at least one image property that is determinative of permeabilization in the tissue sample;
c) an apparatus for determining an optimum value for the at least one parameter based on the correlation between the variations in the parameter and the image property;
d) an apparatus for storing the optimum value of the at least one parameter; and
e) an apparatus for informing a user of the optimum value of the at least one parameter.

The foregoing and other features and advantages of the invention will become further apparent from the following detailed description of the invention, read in conjunction with the Figures.

BRIEF DESCRIPTION OF THE FIGURES

FIGS. 4a-4c show photomicrographic images of a tissue optimization slide representing cDNA footprints of mouse brain tissue as a function of permeabilization time after 5 minutes, 15 minutes and 30 minutes, respectively.

FIG. 5 shows a plot of net average image intensity (arbitrary fluorescent units) versus permeabilization time (minutes) for each of the images shown in FIGS. 4a-4c.

FIG. 10 is a table containing normalized metrics for the eight images (columns 1-8) from the tissue optimization slide represented in FIG. 8. The metrics normalize image sharpness, on a scale of 0 to 1 for 28 different image sharpness algorithms (rows AMCO through WAVRA).

FIG. 13 is a table containing normalized metrics for the eight images (columns 1-8) from the tissue optimization slide represented in FIG. 11. The metrics normalize image sharpness, on a scale of 0 to 1, for 28 different image sharpness algorithms (rows AMCO through WAVRA).

FIG. 20 is a table containing normalized metrics for the eight images (columns 1-8) from the tissue optimization slide represented in FIG. 18. The metrics normalize image sharpness, on a scale of 0 to 1, for 28 different image sharpness algorithms (rows AMCO through WAVRA).

FIG. 25 is a table containing normalized metrics for the eight images (columns 1-8) from the tissue optimization slide represented in FIG. 23. The metrics normalize image sharpness, on a scale of 0 to 1, for 28 different image sharpness algorithms (rows AMCO through WAVRA).

FIG. 29 is a table containing normalized metrics for the eight images (columns 1-8) from the tissue optimization slide represented in FIG. 26. The metrics normalize image sharpness, on a scale of 0 to 1, for 28 different image sharpness algorithms (rows AMCO through WAVRA).

DETAILED DESCRIPTION OF THE INVENTION

Figure 1:
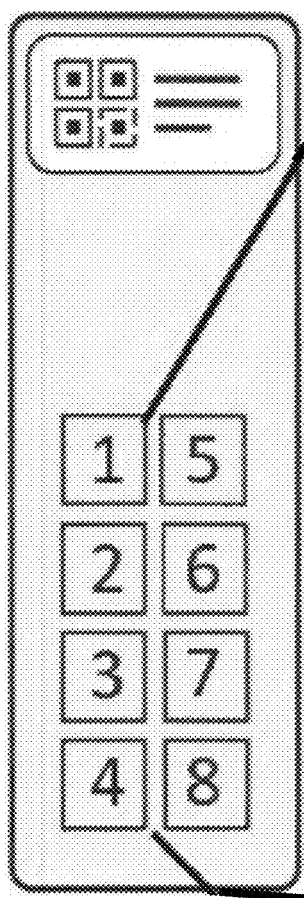
FIG. 1 schematically illustrates a template for a tissue optimization slide having eight square subsections or regions (top to bottom, left to right, numbered as 1-4 and 5-8, respectively), as used for the permeabilized tissue sample represented in FIGS. 2a-2e.

Disclosed are methods for optimizing permeabilization of cellular tissues used for spatial transcriptomics. Various parameters that influence the permeabilization may be selected, used to permeabilize cells and to release analytes (e.g., RNAs) from the cells onto, for example, an array surface. The analytes on the array, or amplification products (e.g., cDNA) made from mRNA analytes on the array, may be imaged. Various image properties may be analyzed to determine values for the parameter tested that yield optimal permeabilization.

By correlating the image property with the variations in the parameters examined, the permeabilization can be optimized for a parameter. The method can be used to optimize the value of one parameter, to independently optimize the value of two or more parameters, or to optimize the values of two or more parameters simultaneously and in combination.

Exemplary image properties that can be quantified to determine an optimal level of permeabilization include without limitation image brightness and sharpness. Exemplary parameters that influence these image properties include without limitation permeabilization time, permeabilization temperature, composition and concentration of permeabilization reagent, tissue fixing agent, and tissue staining agent.

In one embodiment, the property to be quantified and optimized is image brightness. Image brightness is representative of the amount of transcripts captured and indicates assay sensitivity. In one embodiment, the tissue sample that has been optionally fixed and optionally stained is permeabilized on a tissue optimization slide that includes a reverse transcription primer, using selected permeabilization conditions. The reverse transcription primer can include an oligonucleotide (e.g., fluorescent DNA or RNA capture probes) as described herein. Following permeabilization, reverse transcription of the mRNA released from the permeabilized tissue sample and captured on the oligonucleotides on the array surface can be performed using procedures described in the "User Guide for Visium Spatial Gene Expression Reagent Kits—Tissue Optimization," Rev. A, November 2019, published by 10×Genomics. The reverse transcription yields a cDNA footprint on the slide surface which can then be imaged following removal of the tissue sample from the slide. The brightness of the resulting image (which is suitably a fluorescence image) can be quantified using a variety of techniques as described herein.

In one embodiment, the areas of the image that correspond to the permeabilized tissue and the areas of the image that correspond to the background can be identified. In one implementation of this technique, a mask image can be prepared that minimizes or eliminates the background components of the image. In one example, the mask assigns a value of 1 for each pixel in the tissue region of the image and a value of zero for each pixel in the background region of the image (e.g., areas around the tissue region). The original image and the mask image can be merged to yield a tissue image that attributes a pixel value only to the tissue region of the image and minimizes the background region. The values of the pixels in the tissue image can be plotted to quantify the pixel count versus pixel intensity (histogram of pixel intensities) for the tissue region of the image. The same can be done for the background region of the tissue. Statistical parameters (such as mean, median, mode, standard deviation, root mean square error, different percentiles, quartiles, etc.) of the pixel intensity values of both the tissue and the background can then be calculated, reported, and plotted as quantitative metrics to compare the different permeabilization conditions. This procedure can be repeated using tissue samples permeabilized under various conditions of time, temperature, reagent composition and concentration in order to quantify the optimal image brightness as an aide for optimizing the permeabilization conditions of a tissue.

In another embodiment, the property to be quantified and optimized is image sharpness. Image sharpness is a proxy for the resolution of the assay. In one embodiment, image sharpness can be quantified using a variety of quantification instruments and techniques, including without limitation Fast Fourier Transform ("FFT") approaches. Fourier Transform converts an image into its sine and cosine components and thereby represents the image in a frequency domain. If the input signal is an image, then the number of frequencies in the frequency domain is equal to the number of pixels in the image or spatial domain. FFT processes the images in two dimensions, x and y, to provide a radial profile of each image. The FFT thus displays the spatial frequency of each image, which is a measure of how often the sinusoidal components of the image repeat per unit of distance, to indicate the size of features present in the image. Smaller features coupled with higher spatial frequencies correlate with resolution or sharpness. A high level of such smaller features indicates higher resolution and a sharper image. The resulting measurements can be used to calculate metrics for resolution such as average frequency over a range, intensity of a frequency range or ratio of different frequencies, thereby serving as an aide for optimizing the permeabilization conditions of the tissue.

Image sharpness of the assay can also be quantified using any combination of the following algorithms that are used in autofocusing applications:

Absolute Central Moment, Brenner's function, Image contrast, Image curvature, DCT energy ratio, DCT reduced energy ratio, Gaussian derivative, Graylevel variance, Graylevel local variance, Normalized GLV, Energy of gradient, Thresholded gradient, Squared gradient, Helmli's mean method, Histogram entropy, Histogram range, Energy of Laplacian, Modified Laplacian, Variance of Laplacian, Diagonal Laplacian, Steerable filters, Spatial frequency, Tenengrad, Tenengrad variance, Vollath's correlation, Sum of Wavelet coefficients, Sum of Wavelet coefficients A, Variance of Wavelet, and Multi-level two-dimensional inverse FWT.

Various other techniques for quantifying image brightness and image sharpness can also be employed, as described herein.

Definitions

Unless defined otherwise, all technical and scientific terms used herein have the same meaning as commonly understood by one of ordinary skill in the art to which the present invention pertains. It is to be understood that the terminology used herein is for describing embodiments only and is not intended to be limiting. For purposes of interpreting this disclosure, the following description of terms will apply and, where appropriate, a term used in the singular form will also include the plural form and vice versa.

Herein, "analyte" refers to a substance whose chemical constituents are being identified and/or measured. Generally, this application refers to analytes from and/or produced by cells, for example as found in tissue samples. Any or all molecules or substance from or produced by a cell may be referred to herein as analytes. Chemically, cellular analytes may include proteins, polypeptides, peptides, saccharides, polysaccharides, lipids, nucleic acids, and other biomolecules. In some examples, the analytes referred to in this application are RNAs, particularly mRNAs.

Herein, "array" refers to a region on a support that contains multiple demarcated regions of oligonucleotides, interspersed with intervening regions that do not contain oligonucleotides. In some examples, these regions may be referred to as "oligonucleotide arrays" or "capture areas". The arrays herein generally have oligonucleotides that contain spatial barcodes and, thus, the arrays may be referred to as "spatial" arrays.

Herein, "brightness" or "image brightness" is an image property that may be used to determine permeabilization. Brightness is generally used as a proxy for the amounts of transcripts captured and indicates assay sensitivity. "Brightness" represents the fluorescence output per fluorophore.

Herein, "footprint" refers to analytes released from permeabilized cells that are part of a tissue sample. Analytes can be mRNA. In some examples, the released mRNA may be quantified by detecting immunofluorescent probes hybridized to the mRNA. In some examples, the released mRNA may be quantified by detecting cDNA that incorporates fluorescent nucleoside triphosphates using the mRNA as template. The fluorescent cDNA can therefore provide a cDNA footprint.

Herein, "fix," refers to formation of covalent bonds, such as crosslinks, between biomolecules or within molecules. The process of fixing cells for example, is called "fixation." The agent that causes fixation is generally referred to as a "fixative" or "fixing agent." "Fixed cells" or "fixed tissues" refer to cells or tissues that have been in contact with a fixative under conditions sufficient to allow or result in formation of intra- and inter-molecular crosslinks between biomolecules in the biological sample. Fixation may be reversed and the process of reversing fixation may be referred to as "un-fixing" or "decrosslinking." Unfixing or decrosslinking refers to breaking or reversing the formation of covalent bonds in biomolecules formed by fixatives. Non limiting examples of fixatives or fixing agents include methanol, paraformaldehyde, formalin, and acetone to name a few.

Herein, "hybridize" refers to a nucleotide sequence of a single-stranded nucleic acid molecule forming a complex with a nucleic acid molecule having a partially, substantially or fully complementary nucleotide sequence. Generally, the complex forms through hydrogen bonding between complementary nucleotide bases in separate nucleic acid molecules.

Herein, "parameter" refers to a condition that may influence permeabilization of a tissue sample.

Herein, "permeabilize" means to cause cells, generally within a tissue, to release analytes by disrupting the integrity of cellular membranes and/or cell walls.

Herein, "sample" or "biological sample" generally refers to a collection of cells or to a tissue. Generally, a tissue contains multiple cells, often similar cells that may perform the same or similar functions. The sample may be a cell sample. The sample may be a cell line or cell culture sample. The sample can include one or more cells, or one or more cell aggregates or clusters. The sample may be a tissue sample, such as a biopsy, core biopsy, needle aspirate, or fine needle aspirate. The sample may be a tissue from a diseased or cancerous organ, or one suspected of being diseased or cancerous. Example tissue types in animals may include connective, epithelial, brain, adipose, muscle and nervous tissue. The sample may be a fluid sample, such as a blood sample, urine sample, or saliva sample. The sample may be a skin sample. The sample may be a cheek swab. The sample may be a plasma or serum sample. In some examples, a sample may comprise any number of macromolecules, for example, cellular macromolecules or cellular analytes. The present disclosure is not limited to any particular type of tissue.

Herein, "section" generally refers to a thin layer or slice from a larger object. Generally, herein, sections are thin slices taken from tissue blocks, such as 10 um sections for example.

Herein, "sharpness" or "image sharpness" is an image property that may be used to determine permeabilization. Sharpness is generally used as a proxy for the resolution of the assay.

Obtaining Spatially Aligned Analyte Expression Data from Cells and Tissues

Spatial analysis methodologies and compositions described herein can provide a vast amount of analyte and/or expression data for a variety of analytes within a biological sample at high spatial resolution. Spatial analysis methods and compositions can include, e.g., the use of a capture probe including a spatial barcode (e.g., a nucleic acid sequence that provides information as to the location or position of an analyte within a cell or a tissue sample, including a mammalian cell or a mammalian tissue sample) and a capture domain that is capable of binding to an analyte (e.g., a protein and/or a nucleic acid) produced by and/or present in a cell. Spatial analysis methods and compositions can also include the use of a capture probe having a capture domain that captures an intermediate agent for indirect detection of an analyte. For example, the intermediate agent can include a nucleic acid sequence (e.g., a barcode) associated with the intermediate agent. Detection of the intermediate agent is therefore indicative of the analyte in the cell or tissue sample, it serves as a proxy for the analyte.

Non-limiting aspects of spatial analysis methodologies and compositions are described in U.S. Pat. Nos. 10,774, 374, 10,724,078, 10,480,022, 10,059,990, 10,041,949, 10,002,316, 9,879,313, 9,783,841, 9,727,810, 9,593,365, 8,951,726, 8,604,182, 7,709,198, U.S. Patent Application Publication Nos. 2020/239946, 2020/080136, 2020/0277663, 2020/024641, 2019/330617, 2019/264268, 2020/256867, 2020/224244, 2019/194709, 2019/161796, 2019/085383, 2019/055594, 2018/216161, 2018/051322, 2018/0245142, 2017/241911, 2017/089811, 2017/067096, 2017/029875, 2017/0016053, 2016/108458, 2015/000854, 2013/171621, WO 2018/091676, WO 2020/176788, Rodrigues et al., Science 363(6434):1463-1467, 2019; Lee et al., Nat. Protoc. 10(3):442-458, 2015; Trejo et al., PLoS ONE 14(2): e0212031, 2019; Chen et al., Science 348(6233):aaa6090, 2015; Gao et al., BMC Biol. 15:50, 2017; and Gupta et al., Nature Biotechnol. 36:1197-1202, 2018; the Visium Spatial Gene Expression Reagent Kits User Guide (e.g., Rev C, dated June 2020), and/or the Visium Spatial Tissue Optimization Reagent Kits User Guide (e.g., Rev C, dated July 2020), both of which are available at the 10×Genomics Support Documentation website, and can be used herein in any combination. The above references, if US Patents or US Patent Publications, are incorporated herein by reference in their entirety. Further non-limiting aspects of spatial analysis methodologies and compositions are described herein.

Array-based spatial analysis methods involve the transfer of one or more analytes from a biological sample to an array of features (e.g., spots) on a substrate, where each feature is associated with a plurality of capture probes that provide a unique spatial location on the array. Subsequent analysis of the transferred analytes includes determining the identity of the analytes and the spatial location of the analytes within the biological sample. The spatial location of an analyte within the biological sample is determined based on the feature to which the analyte is bound (e.g., directly or indirectly) on the array, and the feature's relative spatial location within the array.

There are at least two methods to associate a spatial barcode with one or more neighboring cells, such that the spatial barcode identifies the one or more cells, and/or contents of the one or more cells, as associated with a particular spatial location. One method is to promote analytes or analyte proxies (e.g., intermediate agents) out of a cell and towards a spatially-barcoded array (e.g., including spatially-barcoded capture probes). Another method is to cleave spatially-barcoded capture probes from an array and promote the spatially-barcoded capture probes towards and/ or into or onto the biological sample.

In some cases, capture probes may be configured to prime, replicate, and consequently yield optionally barcoded extension products from a template (e.g., a DNA or RNA template, such as an analyte or an intermediate agent, including a ligation product or an analyte capture agent, or a portion thereof), or derivatives thereof (see, e.g., Section (II)(b)(vii) of WO 2020/176788 and/or U.S. Patent Application Publication No. 2020/0277663 regarding extended capture probes; incorporated herein by reference in their entirety). In some cases, capture probes may be configured to form ligation products with a template (e.g., a DNA or RNA template, such as an analyte or an intermediate agent, or portion thereof), thereby creating ligation products that serve as proxies for a template. As used herein, an "extended capture probe" refers to a capture probe having additional nucleotides added to the terminus (e.g., 3' or 5' end) of the capture probe thereby extending the overall length of the capture probe. For example, an "extended 3' end" indicates additional nucleotides were added to the most 3' nucleotide of the capture probe to extend the length of the capture probe, for example, by polymerization reactions used to extend nucleic acid molecules including templated polymerization catalyzed by a polymerase (e.g., a DNA polymerase or a reverse transcriptase). In some embodiments, extending the capture probe includes adding to a 3' end of a capture probe a nucleic acid sequence that is complementary to a nucleic acid sequence of an analyte or intermediate agent specifically bound to the capture domain of the capture probe. In some embodiments, the capture probe is extended using reverse transcription. In some embodiments, the capture probe is extended using one or more DNA polymerases. The extended capture probes include the sequence of the capture probe and the sequence of the spatial barcode of the capture probe.

In some embodiments, extended capture probes are amplified (e.g., in bulk solution or on the array) to yield quantities that are sufficient for downstream analysis, e.g., via DNA sequencing. In some embodiments, extended capture probes (e.g., DNA molecules) act as templates for an amplification reaction (e.g., a polymerase chain reaction).

Additional variants of spatial analysis methods, including in some embodiments, an imaging step, are described in Section (II)(a) of WO 2020/176788 and/or U.S. Patent Application Publication No. 2020/0277663. Analysis of captured analytes (and/or intermediate agents or portions thereof), for example, including sample removal, extension of capture probes, sequencing (e.g., of a cleaved extended capture probe and/or a cDNA molecule complementary to an extended capture probe), sequencing on the array (e.g., using, for example, in situ hybridization or in situ ligation approaches), temporal analysis, and/or proximity capture, is described in Section (II)(g) of WO 2020/176788 and/or U.S. Patent Application Publication No. 2020/0277663. Some quality control measures are described in Section (II)(h) of WO 2020/176788 and/or U.S. Patent Application Publication No. 2020/0277663.

Spatial information can provide information of biological and/or medical importance. For example, the methods and compositions described herein can allow for: identification of one or more biomarkers (e.g., diagnostic, prognostic, and/or for determination of efficacy of a treatment) of a disease or disorder; identification of a candidate drug target for treatment of a disease or disorder; identification (e.g., diagnosis) of a subject as having a disease or disorder; identification of stage and/or prognosis of a disease or disorder in a subject; identification of a subject as having an increased likelihood of developing a disease or disorder; monitoring of progression of a disease or disorder in a subject; determination of efficacy of a treatment of a disease or disorder in a subject; identification of a patient subpopulation for which a treatment is effective for a disease or disorder; modification of a treatment of a subject with a disease or disorder; selection of a subject for participation in a clinical trial; and/or selection of a treatment for a subject with a disease or disorder.

Spatial information can provide information of biological importance. For example, the methods and compositions described herein can allow for: identification of transcriptome and/or proteome expression profiles (e.g., in healthy and/or diseased tissue); identification of multiple analyte types in close proximity (e.g., nearest neighbor analysis); determination of up- and/or down-regulated genes and/or proteins in diseased tissue; characterization of tumor microenvironments; characterization of tumor immune responses; characterization of cells types and their co-localization in tissue; and identification of genetic variants within tissues (e.g., based on gene and/or protein expression profiles associated with specific disease or disorder biomarkers).

In some cases, spatial analysis can be performed by detecting multiple oligonucleotides that hybridize to an analyte. In some instances, for example, spatial analysis can be performed using RNA-templated ligation (RTL). Methods of RTL have been described previously (See, e.g., Credle et al., *Nucleic Acids Res.* 2017 Aug. 21; 45(14): e128). Typically, RTL includes hybridization of two oligonucleotides to adjacent sequences on an analyte (e.g., an RNA molecule, such as an mRNA molecule). In some instances, the oligonucleotides are DNA molecules. In some instances, one of the oligonucleotides includes at least two ribonucleic acid bases at the 3' end and/or the other oligonucleotide includes a phosphorylated nucleotide at the 5' end. In some instances, one of the two oligonucleotides includes a capture domain (e.g., a poly(A) sequence, a non-homopolymeric sequence). After hybridization to the analyte, a ligase (e.g., SplintR ligase) ligates the two oligonucleotides together, creating a ligation product. In some instances, the two oligonucleotides hybridize to sequences that are not adjacent to one another. For example, hybridization of the two oligonucleotides creates a gap between the hybridized oligonucleotides. In some instances, a polymerase (e.g., a DNA polymerase) can extend one of the oligonucleotides prior to ligation. After ligation, the ligation product is released from the analyte. In some instances, the ligation product is released using an endonuclease (e.g., RNAse H). The released ligation product can then be captured by capture probes (e.g., instead of direct capture of an analyte) on an array, optionally amplified, and sequenced, thus determining the location and optionally the abundance of the analyte in the biological sample.

During analysis of spatial information, sequence information for a spatial barcode associated with an analyte is obtained, and the sequence information can be used to provide information about the spatial distribution of the analyte in the biological sample. Various methods can be used to obtain the spatial information. In some embodiments, specific capture probes and the analytes they capture are associated with specific locations in an array of features on a substrate. For example, specific spatial barcodes can be associated with specific array locations prior to array fabrication, and the sequences of the spatial barcodes can be stored (e.g., in a database) along with specific array location information, so that each spatial barcode uniquely maps to a particular array location.

Some exemplary spatial analysis workflows are described in the Exemplary Embodiments section of WO 2020/176788 and/or U.S. Patent Application Publication No. 2020/0277663. See, for example, the Exemplary embodiment starting with "In some non-limiting examples of the workflows described herein, the sample can be immersed . . . " of WO 2020/176788 and/or U.S. Patent Application Publication No. 2020/0277663. See also, e.g., the Visium Spatial Gene Expression Reagent Kits User Guide (e.g., Rev C, dated June 2020), and/or the Visium Spatial Tissue Optimization Reagent Kits User Guide (e.g., Rev C, dated July 2020).

In some embodiments, spatial analysis can be performed using dedicated hardware and/or software, such as any of the systems described in Sections (II)(e)(ii) and/or (V) of WO 2020/176788 and/or U.S. Patent Application Publication No. 2020/0277663, or any of one or more of the devices or methods described in Sections Control Slide for Imaging, Methods of Using Control Slides and Substrates for, Systems of Using Control Slides and Substrates for Imaging, and/or Sample and Array Alignment Devices and Methods, Informational labels of WO 2020/123320.

Prior to transferring analytes from the biological sample to the array of features on the substrate, the biological sample can be aligned with the array. Alignment of a biological sample and an array of features including capture probes can facilitate spatial analysis, which can be used to detect differences in analyte presence and/or level within different positions in the biological sample, for example, to generate a three-dimensional map of the analyte presence and/or level.

In some cases, a map of analyte presence and/or level can be aligned to an image of a biological sample using one or more fiducial markers (e.g., objects placed in the field of view of an imaging system which appear in the image produced, as described in the Substrate Attributes Section and Control Slide for Imaging Section of WO 2020/123320). Fiducial markers can be used as a point of reference or measurement scale for alignment (e.g., to align a sample and an array, to align two substrates, to determine a location of a sample or array on a substrate relative to a fiducial marker) and/or for quantitative measurements of sizes and/or distances.

Systems and methodologies in the field of spatial transcriptomics are designed to obtain spatially resolved analyte expression data (e.g., genomics, proteomics, transcriptomics) from tissues. In some examples, a tissue may be overlaid onto a support comprising barcoded oligonucleotides or capture probes. Generally, the oligonucleotides comprise a spatial barcode, which is correlated with and is an identifier for the location of the particular oligonucleotide on the support (e.g., in some examples, oligonucleotides having known barcode sequences are printed onto designated areas of the support). When analytes are released from a biological sample and migrate toward and contact the barcoded oligonucleotides, the barcoded oligonucleotides capture, or hybridize to, the analytes. In some examples, mRNAs may be the analytes and barcoded oligonucleotides may capture mRNAs having specific nucleotide sequences by hybridization, for example the barcoded oligonucleotides comprise a poly(T) capture domain that can hybridize a poly(A) tail of a mRNA. In the examples where mRNA is the analyte, reverse transcription of the captured mRNA can be initiated using added primers, and cDNA is produced using the barcoded oligonucleotide as a template. The resultant cDNA that is synthesized incorporates the barcodes included in the barcoded oligonucleotide or capture probe. The cDNAs may be amplified. A library of the cDNAs/amplified cDNAs is prepared and nucleotide sequences of the libraries are obtained. Nucleotide sequences of the spatial barcodes provides for the data for an mRNA transcript to be mapped back to its location on the support, and by also obtaining an image of the tissue and cells overlaid onto the support at the beginning of the procedure, mRNA transcripts may be mapped to the location in the overlaid tissue, where the mRNA was expressed.

In some examples, a planar support on the surface of which is attached a spatially ordered arrangement of barcoded oligonucleotides comprising analyte capture domains is used. In some examples, an analyte capture domain may be an oligo(dT) sequence for capturing poly(A) sequences of eukaryotic mRNA. Other sequences may be used to capture specific nucleic acids, including specific mRNAs. The arrangement of the oligonucleotides on the surface of the support can be known because the oligonucleotides comprise spatial barcodes. In some examples, the oligonucleotides, with known spatial barcodes, are printed in a known pattern onto specific, known areas of the surface of the planar support in a predetermined arrangement. A tissue is then applied to the surface of the support and analytes (e.g., mRNA) are released from the cells that make up the tissue. mRNAs released from the tissue migrate to the surface of the support and hybridize to oligo(dT) capture domain sequences of the attached oligonucleotides. The hybridized mRNAs are amplified using reverse transcription into complementary oligonucleotides that include sequences from the captured mRNA linked to the spatial barcode of the oligonucleotide to which the mRNA bound. Obtaining and decoding the nucleotide sequences of the complementary oligonucleotides reveals where on the support specific mRNAs bound to oligonucleotides. These locations are then correlated to regions of the tissue that was applied to the surface of the support.

In modifications of the above method, a tissue sample may be probed for expression of specific proteins using antibodies. The antibodies may have attached nucleotide tags having a specific nucleotide sequence that capture domains of the barcoded molecules on a support are designed to capture through hybridization. Thus, proteomic data can be obtained from the oligonucleotide arrays.

In modifications of the above method, a tissue sample may be probed for presence or absence of genetic mutations, variants, diversity, polymorphisms and the like in genomes, including single-nucleotide polymorphisms (SNPs) or single-nucleotide variants (SNVs) in genomes of cells making up the tissue. In some examples, a probe for a SNP or SNV may include a specific nucleotide sequence that can differentially hybridize to a genomic sequence dependent on whether a SNP or SNV is present. In some examples, a probe for a SNP or SNV may include a nucleotide sequence that can hybridize to a genomic sequence that is linked to (e.g., upstream of downstream of) a genomic region that might contain the SNP or SNV. Extension of the hybridized sequence, using the region of the genome that might contain the SNP/SNV as a template, and nucleotide sequencing of the extension product, may be used to determine if the SNP/SNV is present in the extension product. In some examples, probes for specific SNPS or SNVs may be part of the capture domain of certain oligonucleotides that make up the oligonucleotide array. Other techniques may be used to detect SNPs and/or SNVs.

In modifications of the above method, a tissue sample may be probed for isoforms of genes, transcripts (e.g., alternative transcription start sites, alternatively spliced mRNAs) or proteins. In some examples, a probe for an isoform of a gene or transcript may be designed to hybridize to one form but not the other, or may be designed to hybridize to or near a region that may contain the isoform such that amplification and/or extension of the hybridized probe, and optional nucleotide sequencing of the amplified product, can detect presence or absence of specific isoforms. In some examples, a probe for an isoform of a protein may be an antibody designed to differentially bind to the different isoforms. The antibodies used may have attached nucleotide tags that can capture domains of the barcoded molecules on a support, as described above.

Cell Permeabilization in Spatial Transcriptomics

The ability of a spatial array to capture an analyte and determine its spatial location within a tissue sample is dependent on many factors. One of those factors is the ability of the analyte or analyte proxy to leave the tissue sample and hybridize to the capture domain of the capture probe. The present invention is directed to a quantitative method of optimizing the permeabilization of cellular tissues used for spatial transcriptomics, thereby enhancing the ability of an analyte within a tissue sample to migrate from the tissue sample and bind to the capture domain of a capture probe on the spatial array.

Common parameters that influence permeabilization include, without limitation, permeabilization time, permeabilization temperature, permeabilization reagent type and concentration, tissue preparation (including tissue fixing agent and tissue staining agent), and later removal of the tissue from the slide. Permeabilization methods can also be varied between chemical permeabilization (using reagents), mechanical permeabilization (e.g., magnetic stirring, etc.) and electrophoresis. Optimum values for the permeabilization parameters may vary depending on the tissue type. Optimizing permeabilization conditions for each tissue sample type can be very beneficial in capturing as many analytes as possible from any given tissue sample type.

Types of tissue samples for which optimized permeabilization can be beneficial using the method of the invention include without limitation mammalian brain tissue, mammalian olfactory bulb tissue, mammalian spleen tissue, mammalian lung tissue, mammalian esophageal tissue, mammalian skin tissue, mammalian liver tissue, mammalian testicular tissue, mammalian ovarian tissue, mammalian bone tissue, mammalian heart tissue, mammalian abdominal tissue, and mammalian intestinal tissue. Optimal values for permeabilization parameters vary depending on the type of mammal that produces the tissue. For example, the optimal permeabilization conditions for human lung tissue can differ from the optimal permeabilization conditions for mouse lung tissue. Further, within a species there may be differences based on the individual from which the tissued originated.

Permeabilization Time

Optimal permeabilization time is influenced not only by the tissue sample type, but also by the values for other permeabilization parameters such as temperature, reagent type and concentration. Depending on these other parameters, the optimal permeabilization time can be between about 3 minutes and about 90 minutes, suitably between about 5 minutes and about 60 minutes. In accordance with the invention, the permeabilization time can be quantified and optimized by first varying the time in suitable increments within that range. For example, the permeabilization time can be varied in increments of about three minutes, or about four minutes, or about five minutes, or about six minutes, or about eight minutes, or about ten minutes, or about twelve minutes for different sections of a tissue sample to determine the optimal permeabilization time for a given tissue type and set of conditions.

FIG. 1 illustrates an exemplary tissue optimization (TO) slide that can be used to vary the permeabilization time, temperature and other parameters for different tissue sample types. The TO slide is divided into eight rectangular capture areas, numbered 1 through 8. Each capture area is coated with a lawn of capture probes. The capture probes include capture domains comprising a single-stranded sequence of poly-deoxythymine (dT) (i.e., polyT), designed to capture poly(A) tail sequences of eukaryotic mRNAs. In some examples, capture domains may be other nucleotide sequences designed to be complementary to specific RNAs or DNAs and to capture those RNAs or DNAs through hybridization. A prepared tissue section (e.g., fresh frozen tissue section, FFPE tissue section, etc.) can be place on the array slide. The tissue section can be stained with a suitable dye as described below, and imaged. When hematoxylin and eosin (H&E) are used as the dye, the hematoxylin stains cell nuclei blue, and eosin stains the extracellular matrix and cytoplasm pink, with other structures assuming different shades, hues and combinations of these colors. A permeabilization reagent can be added to the tissue on the array.

Figure 2A:
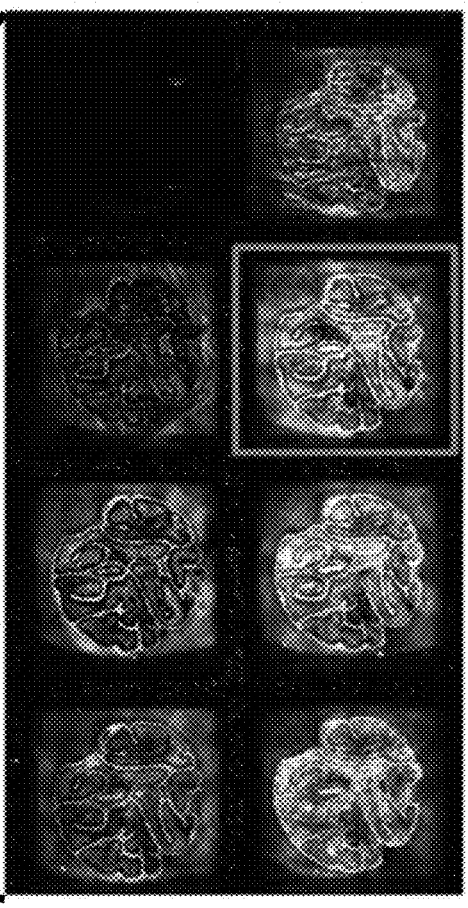
FIGS. 2a-e show photomicrographic images of a tissue optimization slide for cDNA footprints of different identified mouse tissues as a function of permeabilization time, varied in increments from top to bottom, left to right. The region of each slide outlined by a solid line box (and indicated by an arrow) was considered an optimal permeabilization result.
Figure 2B:
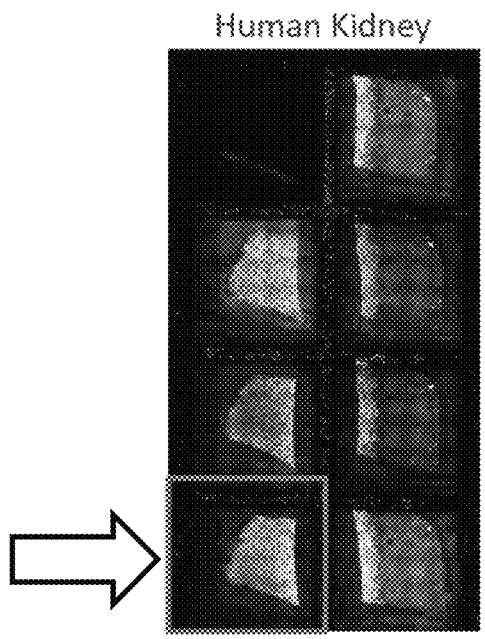
Figure 2C:
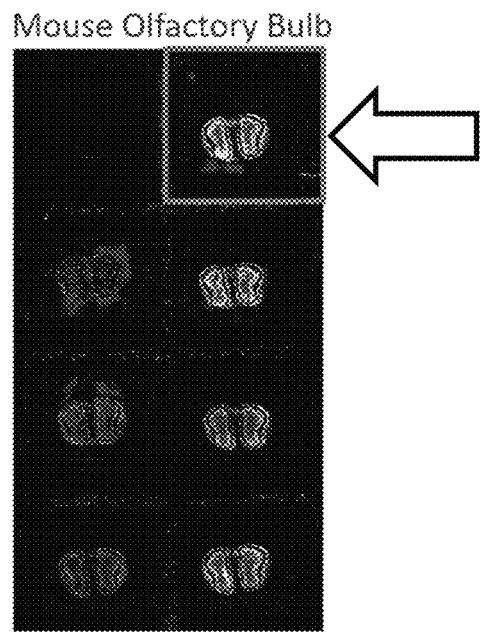
Figure 2D:
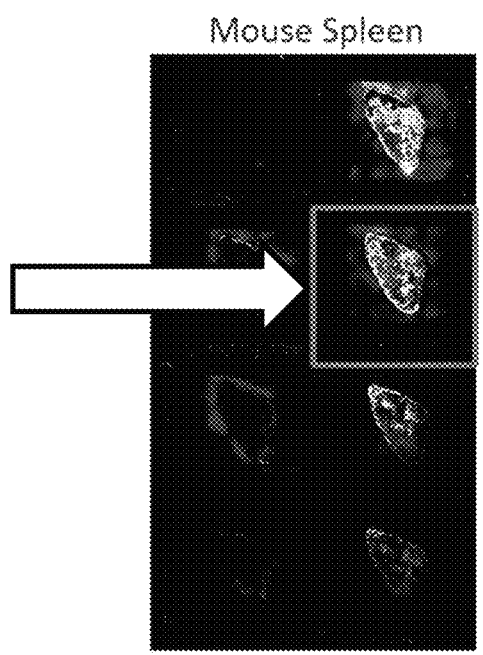
Figure 2E:
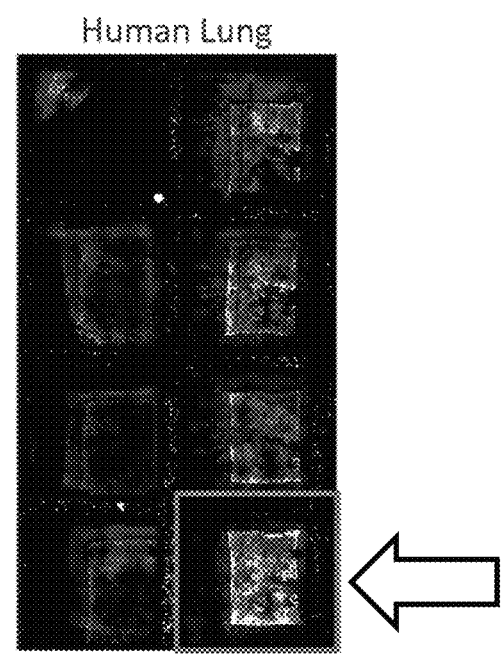

FIGS. 2a-2e demonstrate the various times that can be examined for optimization of different cellular tissue samples. For each tissue type, eight tissue sections were initially prepared using methanol as the fixing agent and no staining agent. The tissue sections were permeabilized for various times using a permeabilization temperature of 37 degrees C. and using a combination of proteinase-K with 10% by weight sodium dodecyl sulfate as the permeabilization reagent. The permeabilization times for the tissue samples placed in each of the capture regions 1-8 were as follows: Region 1—negative control (no permeabilization), Region 2—3 minutes, Region 3—6 minutes, Region 4—12 minutes, Region 5—18 minutes, Region 6—24 minutes, Region 7—30 minutes, Region 8—36 minutes. The arrow in each of the tissue type photomicrographs in FIGS. 2a-2e point to the optimal permeabilization times for each kind of tissue, represented by the best combination of image brightness and sharpness. Fluorescent cDNA synthesis was carried out, as described later in this document. FIGS. 2a-2e represent photomicrographic images that capture the fluorescence resulting from the fluorescently labelled cDNA synthesis. The optimum times varied by a factor of three and were 24 minutes for mouse small intestine tissue (FIG. 2a), 12 minutes for human kidney tissue (FIG. 2b), 18 minutes for mouse olfactory bulb tissue (FIG. 2c), 24 minutes for mouse spleen tissue (FIG. 2d) and 36 minutes for human lung tissue (FIG. 2e). FIGS. 2a-2e provide examples of qualitative optimization in which the permeabilization time is optimized by viewing the photomicrographs for brightness and sharpness. Optimization according to the invention further involves quantifying the image properties as described below.

Permeabilization Temperature

Other parameters that can be optimized include permeabilization temperature, which typically ranges from about 4 degrees C. to about 50 degrees C., depending on the tissue type, permeabilization reagent, and other variables. In order to optimize the permeabilization temperature for a given tissue type and set of conditions, the permeabilization temperature can be varied within this range in increments of about 1 degree, or about 2 degrees, or about 3 degrees, or about 4 degrees, or about 5 degrees, or about 6 degrees, or about 8 degrees, or about 10 degrees, or about 12 degrees Celsius. When two or more parameters such as permeabilization time and temperature are to be optimized, the parameters can be optimized simultaneously or in sequence.

An iterative technique may be employed for simultaneous optimization of two or more parameters. Using the foregoing examples, permeabilization time may be optimized at 37 degrees C. for a given tissue type, such as mouse spleen, resulting in an optimum time of 24 minutes as shown in FIG. 2c. Then, using the 24-minute time, a next set of cellular tissue sections can be permeabilized at selected temperature increments above and below 37 degrees C. This may result in discovery of a temperature yielding somewhat better permeabilization. Using that newly discovered temperature, a next set of cellular tissue samples can be permeabilized by varying the time in small increments above and below 24 minutes. This might result in discovery of a permeabilization time at the new temperature that yields still better permeabilization. These iterations can be repeated until the best permeabilization based on both time and temperature is achieved. Similar iterations can be performed for simultaneous optimization of reagents, reagent concentrations, and other parameters.

Permeabilization Reagent

Another parameter that can be optimized according to the method of the invention is the type of permeabilization reagent. Suitable permeabilization reagents include without limitation one or more organic solvents (e.g., acetone, ethanol, and methanol), detergents (e.g., saponin, Triton X-100™ ($C_{14}$—$H_{22}$—O—($C_2$—$H_4$—O)$_n$), Tween-20™ (polyoxyethylene sorbitan monolaurate), sodium dodecyl sulfate (SDS), and enzymes (e.g., trypsin, collagenase, proteases such as pepsin or proteinase K). In some embodiments, the detergent is an anionic detergent (e.g., SDS or N-lauroylsarcosine sodium salt solution). In some embodiments, the tissue section can be permeabilized using any of the detergents described herein before, concurrent or after treatment with any of the enzymes described herein.

In some embodiments, the permeabilization reagent can be an aqueous solution of sodium dodecyl sulfate (SDS) and/or N-lauroylsarcosine or N-lauroylsarcosine sodium salt. The tissue section can be incubated with and permeabilized using such reagents in a concentration of greater than about 1.0 w/v %, or greater than about 2.0 w/v %, or greater than about 3.0 w/v %, or greater than about 4.0 w/v %, or greater than about 5.0 w/v %, greater than about 6.0 w/v %, or greater than about 7.0 w/v %, or greater than about 8.0 w/v %, or greater than about 9.0 w/v %, or greater than about 10.0 w/v %, or greater than about 11.0 w/v %, or greater than about 12.0 w/v %, or greater than about 13.0 w/v %. Specific concentration ranges can be about 1.0 w/v % to about 14.0 w/v %, or about 2.0 w/v % to about 14.0 w/v %, or about 2.0 w/v % to about 12.0 w/v %, or about 2.0 w/v % to about 10.0 w/v %, or about 4.0 w/v % to about 14.0 w/v %, or about 4.0 w/v % to about 12.0 w/v %, or about 4.0 w/v % to about 10.0 w/v %, or about 6.0 w/v % to about 14.0 w/v %, or about 6.0 w/v % to about 12.0 w/v %, or about 6.0 w/v % to about 10.0 w/v %, or about 8.0 w/v % to about 14.0 w/v %, or about 8.0 w/v % to about 12.0 w/v %, or about 8.0 w/v % to about 10.0 w/v %, or about 10.0% w/v % to about 14.0 w/v %, or about 10.0 w/v % to about 12.0 w/v %, or about 12.0 w/v % to about 14.0 w/v %.

In some embodiments, the permeabilization reagent can be one or more lysis reagents. Examples of suitable lysis reagents include, but are not limited to, bioactive reagents such as lysis enzymes that are used for lysis of different tissue cell types, including without limitation lysozymes, achromopeptidase, lysostaphin, labiase, kitalase, lyticase, and a variety of other commercially available lysis enzymes. Other lysis reagents can additionally or alternatively be added to the biological sample to facilitate permeabilization. For example, surfactant-based lysis solutions can be used to lyse tissue cells. Lysis solutions can include ionic surfactants such as, for example, sarcosyl and sodium dodecyl sulfate (SDS). More generally, chemical lysis agents can include, without limitation, organic solvents, chelating agents, detergents, surfactants, and chaotropic agents.

In some embodiments, the cellular tissue can be permeabilized by non-chemical permeabilization methods. Non-chemical permeabilization methods include, but are not limited to, physical lysis techniques such as electroporation, mechanical permeabilization methods (e.g., bead beating using a homogenizer and grinding balls to mechanically disrupt sample tissue structures), acoustic permeabilization (e.g., sonication), and thermal lysis techniques such as heating to induce permeabilization of the tissue cells.

In some embodiments, a permeabilization reagent solution may contain one or more proteases. A tissue section treated with a protease capable of degrading histone proteins can result in the generation of fragmented genomic DNA. The fragmented genomic DNA can be captured using the same capture domain (e.g., capture domain having a poly(T) sequence) used to capture mRNA, for example by using a proxy for the DNA that includes a poly(A) tail. In some embodiments, a tissue can be treated with a protease capable of degrading histone proteins and an RNA protectant prior to spatial profiling in order to facilitate the capture of both genomic DNA and mRNA. As used herein, the term "histone protein" typically refers to a linker histone protein (e.g., H1) and/or a core histone protein (e.g., H2A, H2B, H3, and H4).

In some instances, a protease reagent can be used to degrade linker histone proteins and/or core histone proteins. Any suitable protease capable of degrading histone proteins in a cellular tissue can be used. Non-limiting examples of proteases capable of degrading histone proteins include proteases inhibited by leupeptin and TLCK (Tosyl-L-lysyl-chloromethane hydrochloride), a protease encoded by the EUO gene from *Chlamydia trachomatis* serovar A, granzyme A, a serine protease (e.g., trypsin or trypsin-like protease, neutral serine protease, elastase, cathepsin G), an aspartyl protease (e.g., cathepsin D), a peptidase family C1 enzyme (e.g., cathepsin L), pepsin, proteinase K, a protease that is inhibited by the diazomethane inhibitor Z-Phe-CHN (2) or the epoxide inhibitor E-64, a lysosomal protease, or an azurophilic enzyme (e.g., cathepsin G, elastase, proteinase 3, neutral serine protease). In some embodiments, a serine protease is a trypsin enzyme, trypsin-like enzyme or a functional variant or derivative thereof.

In some embodiments, the protease reagent can include a trypsin enzyme such as P00761, P00760, Q29463, or a combination thereof. In some embodiments, a protease reagent capable of degrading one or more histone proteins includes an amino acid sequence with at least 80% sequence identity to P00761, P00760, or Q29463. In some embodiments, a protease reagent capable of degrading one or more histone proteins includes an amino acid sequence with at least 85%, 90%, 91%, 92%, 93%, 94%, 95%, 96%, 97%, 98%, or 99% identity to P00761 (SEQ ID NO: 8), P00760 (SEQ ID NO: 9), or Q29463 (SEQ ID NO: 10). A protease reagent may be considered a functional variant if it has at least 50% e.g., at least 60%, 70%, 80%, 90%, 95%, 96%, 97%, 98%, 99%, or 100% of the activity relative to the activity of the normal or wild-type protease. In some embodiments, the protease reagent can include enzymatic treatment with pepsin enzyme, or pepsin like enzyme.

In some embodiments, the protease reagent can include a pepsin enzyme such as P00791/PEPA_PIG; P00792/PEPA_BOVIN, functional variants, derivatives, or combinations thereof. Additionally, the protease reagent may be contained in a reaction mixture (solution), which also includes other components (e.g., buffer, salt, chelator (e.g., EDTA), and/or detergent (e.g., SDS, N-lauroylsarcosine sodium salt solution)). The reaction mixture may be buffered, having a pH of about 6.5-8.5, e.g., about 7.0-8.0.

The permeabilization reagent solution can contain additional reagents or the tissue section may be treated with additional reagents in order to optimize biological sample permeabilization. In some embodiments, an additional permeabilization reagent is an RNA protectant. As used herein, the term "RNA protectant" refers to a reagent that protects RNA from RNA degradation by, for example, nucleases (e.g., RNases). Any appropriate RNA protectant that protects RNA from degradation can be used. A non-limiting example of a RNA protectant includes organic solvents (e.g., at least 60%, 65%, 70%, 75%, 80%, 85%, 90%, or 95% v/v organic solvent), which include, without limitation, ethanol, methanol, propan-2-ol, acetone, trichloroacetic acid, propanol, polyethylene glycol, acetic acid, or a combination thereof. In some embodiments, an RNA protectant includes ethanol, methanol and/or propan-2-ol, or a combination thereof. In some embodiments, an RNA protectant includes RNA-later ICE (ThermoFisher Scientific). In some embodiments, the RNA protectant includes at least about 60% ethanol. In some embodiments, the RNA protectant includes about 60-95% ethanol, about 0-35% methanol and about 0-35% propan-2-ol, wherein the total amount of organic solvent in the medium is not more than about 95%. In some embodiments, the RNA protectant includes about 60-95% ethanol, about 5-20% methanol and about 5-20% propan-2-ol, wherein the total amount of organic solvent in the medium is not more than about 95%.

In some embodiments, the RNA protectant may be combined with a salt. The salt may include ammonium sulfate, ammonium bisulfate, ammonium chloride, ammonium acetate, cesium sulfate, cadmium sulfate, cesium iron (II) sulfate, chromium (III) sulfate, cobalt (II) sulfate, copper (II) sulfate, lithium chloride, lithium acetate, lithium sulfate, magnesium sulfate, magnesium chloride, manganese sulfate, manganese chloride, potassium chloride, potassium sulfate, sodium chloride, sodium acetate, sodium sulfate, zinc chloride, zinc acetate and zinc sulfate. In some embodiments, the salt is a sulfate salt, for example, ammonium sulfate, ammonium bisulfate, cesium sulfate, cadmium sulfate, cesium iron (II) sulfate, chromium (III) sulfate, cobalt (II) sulfate, copper (II) sulfate, lithium sulfate, magnesium sulfate, manganese sulfate, potassium sulfate, sodium sulfate, or zinc sulfate. In some embodiments, the salt is ammonium sulfate. The salt may be present at a concentration of about 20 g/100 ml of medium or less, such as about 15 g/100 ml, 10 g/100 ml, 9 g/100 ml, 8 g/100 ml, 7 g/100 ml, 6 g/100 ml, 5 g/100 ml or less, e.g., about 4 g, 3 g, 2 g or 1 g/100 ml.

Additionally, the RNA protectant may be included in a medium that further includes a chelator (e.g., EDTA), a buffer (e.g., sodium citrate, sodium acetate, potassium citrate, or potassium acetate, preferably sodium acetate), and/or buffered to a pH between about 4-8 (e.g., about 5, 6, 7). In some embodiments, the cellular tissue is treated with one or more RNA protectants before, contemporaneously with, or after permeabilization. For example, a tissue section can be treated with one or more RNA protectants prior to treatment with one or more permeabilization reagents (e.g., one or more proteases). In another example, a tissue section is treated with a solution including one or more RNA protectants and one or more permeabilization reagents (e.g., one or more proteases). In yet another example, a tissue section is treated with one or more RNA protectants after the tissue section has been treated with one or more permeabilization reagents (e.g., one or more proteases). In some embodiments, a tissue section is treated with one or more RNA protectants prior to fixation. In some embodiments, identifying the location of a captured analyte in the cellular tissue includes a nucleic acid extension reaction. In some embodiments where a capture probe captures a fragmented genomic DNA molecule, a nucleic acid extension reaction includes DNA polymerase. For example, a nucleic acid extension reaction includes using a DNA polymerase to extend the capture probe that is hybridized to the captured analyte (e.g., fragmented genomic DNA) using the captured analyte (e.g., fragmented genomic DNA) as a template. Any DNA polymerase that can extend the capture probe using the captured analyte as a template can be used. Non-limiting examples of DNA polymerases include T7 DNA polymerase; Bsu DNA polymerase; and *E. coli* DNA Polymerase pol I.

In order to optimize the reagent type, the tissue sections on the TO slide can be treated with different permeabilization reagents, such as at least two, or at least three, or at least four, or at least five, or at least six, or at least seven, or at least eight different reagents or reagent combinations. The tissue sections can be permeabilized using a set of conditions that is constant except for the variations in permeabilization reagent, in order to determine the optimal permeabilization reagent for a cellular tissue. This procedure can be repeated using several additional TO slides to evaluate many different reagents and reagent combinations, in order to further optimize the permeabilization reagent type. Once the optimal reagent is determined, the method can be repeated using various amounts and concentrations of the reagent in order to determine the optimal reagent concentration.

Fixing Agents

Another parameter that can affect permeabilization is whether or not the cellular tissue is fixed before permeabilization and, if so, the type of fixing agent used to fix the cellular tissue before permeabilization. A fixing agent is a chemical species that preserves the tissue cells and/or morphology before and during permeabilization. For example, an organic solvent such as an alcohol (e.g., ethanol or methanol), ketone (e.g., acetone), or aldehyde (e.g., formaldehyde or glutaraldehyde), or any combination thereof may act as a fixing agent. Alternatively, or in addition, a cross-linking agent may act as a fixing agent. In some cases, a fixing agent may comprise disuccinimidyl suberate (DSS), dimethylsuberimidate (DMS), formalin, and dimethyladipimidate (DMA), dithio-bis (succinimidyl propionate) (DSP), disuccinimidyl tartrate (DST), and/or ethylene glycol bis (succinimidyl succinate) (EGS), and any combinations thereof. In order to optimize the fixing agent, the tissue sections on the TO slide can be treated with different fixing agents, such as at least two, or at least three, or at least four, or at least five, or at least six, or at least seven, or at least eight different fixing agents. The tissue sections can be permeabilized using a set of conditions that is constant except for the variations in fixing agent, in order to determine the optimal fixing agent for a tissue section.

Staining Agents

The staining agent (if any) used to stain the tissue section before permeabilization can also influence the level of permeabilization of the tissue section. Staining is typically performed after fixing the cellular tissue and facilitates visualization of the tissue sections, pre and post permeabilization. A wide variety of staining agents can be used, including without limitation acridine orange, Bismarck brown, carmine, Coomassie blue, cresyl violet, 4,6-diamidino-2-phenylindole (DAPI), eosin, hematoxylin, ethidium bromide, acid fuchsine, iodine, methyl green, bisbenzimides, iodine, methyl green, methylene blue, neutral red, Nile blue, Nile red, osmium tetroxide, propidium iodide, rhodamine, safrain, radioisotopes, fluorophores, chemiluminescent compounds, bioluminescent compounds, and combinations thereof.

In order to optimize the staining agent, the tissue sections on the TO slide can be treated with different staining agents, such as at least two, or at least three, or at least four, or at least five, or at least six, or at least seven, or at least eight different staining agents. The tissue sections can be permeabilized using a set of conditions that is constant except for the variations in staining agent, in order to determine the optimal staining agent for a cellular tissue.

Creating cDNA Footprints of Permeabilized Tissue Sections

Prior to placing the tissue sections on the TO slide, in some examples, each array area of the TO slide includes a plurality of capture probes that comprise capture domains that interact with the mRNA from the corresponding tissue section to cause hybridization, followed by extension of the capture domain, using the hybridized mRNA as a template, resulting in the formation of a cDNA footprint of the tissue section on the TO slide. A description of one suitable cDNA extension protocol is provided in the Visium Spatial Gene Expression Reagent Kits-Tissue Optimization User Guide, published by 10×Genomics, which is incorporated herein by reference. The incorporation of one or more fluorescently labelled dNTPs during reverse transcription results in the production of fluorescent cDNA (i.e., fluorescent cDNA synthesis) which can be detected via fluorescence microscopy, for example.

Other methods of detecting the amount of an analyte, for example mRNA, released from tissue sections overlaid onto an array after cell permeabilization may be used. In some examples, fluorescent probes that hybridize to captured RNAs released from cells may be applied and detected. In some examples, fluorescent probes that hybridize to captured RNAs may prime synthesis of cDNA and be used for detection. Labels other than fluorescent labels may be used (e.g., colorimetric labels).

In one embodiment, a reverse transcription primer includes a branched mRNA-capturing probe having a plurality of hybridization regions arranged in a straight, stepped or branched chain. The hybridization regions serve as capture domains for target mRNA present on the adjacent surface of the tissue sections. Each capture domain can be an oligonucleotide, a polypeptide, a small molecule, or any combination thereof, that binds, captures and/or detects a target mRNA.

Each capture domain can be a functional nucleic acid sequence configured to interact with the target mRNA molecules. The functional sequence can include a poly(T) sequence, which poly(T) sequences are configured to interact with the mRNA molecules via the poly(A) tail of an mRNA transcript.

Capture domains can include ribonucleotides and/or deoxyribonucleotides as well as synthetic nucleotide residues that can participate in Watson-Crick type or analogous base pair interactions. The capture domains can prime a reverse transcription reaction to generate cDNA that is complementary to the captured mRNA molecules. The capture domains can be ligated to one strand of the captured mRNA molecules. For example, SplintR ligase along with RNA or DNA sequences (e.g., degenerate RNA) can be used to ligate a single-stranded RNA to a capture domain. In some embodiments, ligases with RNA-templated ligase activity, e.g., SplintR ligase, T4 RNA ligase 2 or KOD ligase, can be used to ligate a single-stranded mRNA to the capture domain.

In some embodiments, a capture domain includes a splint oligonucleotide. A capture domain can be located at the end of the capture probe and can include a free 3' end that can be extended, e.g., by template dependent polymerization, to form an extended capture probe. In some embodiments, the capture domain includes a nucleotide sequence that is capable of hybridizing to mRNA present in the cells of the biological tissue contacted with the array. The capture domain can be selected or designed to bind selectively or specifically to a target mRNA by way of hybridization to the mRNA poly(A) tail or other region in the mRNA. Thus, the capture domain can include a poly(T) DNA oligonucleotide, e.g., a series of consecutive deoxythymidine residues linked by phosphodiester bonds, which is capable of hybridizing to the poly(A) tail of mRNA. The capture domain can include nucleotides that are functionally or structurally analogous to a poly(T) tail, for example, a poly(U) oligonucleotide or an oligonucleotide including deoxythymidine analogues. The capture domain can have a sequence that is capable of binding to mRNA. For example, the capture domain can include a nucleic acid sequence (e.g., a poly(T) sequence) capable of binding to a poly(A) tail of an mRNA. In some embodiments, a homopolymer sequence is added to an mRNA molecule using a terminal transferase enzyme in order to produce a molecule having a poly(A) or poly(T)

sequence. For example, a poly(A) sequence can be added to an mRNA, thereby making the mRNA capable of capture by a poly(T) capture domain.

In some embodiments, random sequences, e.g., random hexamers or similar sequences, can be used to form all or a part of the capture domain. For example, random sequences can be used in conjunction with poly(T) (or poly(T) analogue) sequences. Thus, where a capture domain includes a poly(T) (or a "poly(T)-like") oligonucleotide, it can also include a random oligonucleotide sequence (e.g., "poly(T)-random sequence" probe). This can, for example, be located at 5' or 3' of the poly(T) sequence, e.g., at the 3' end of the capture domain. The poly(T)-random sequence probe can facilitate the capture of the mRNA poly(A) tail. In some embodiments, the capture domain can be an entirely random sequence. In some embodiments, a capture domain can be semi-random or fully fixed or defined sequence.

In some embodiments, a pool of two or more capture probes form a mixture, where the capture domain of one or more capture probes includes a poly(T) sequence and the capture domain of one or more capture probes includes random sequences. In some embodiments, a pool of two or more capture probes form a mixture where the capture domain of one or more capture probes includes a poly(T)-like sequence and the capture domain of one or more capture probes includes random sequences. In some embodiments, a pool of two or more capture probes form a mixture where the capture domain of one or more capture probes includes a poly(T)-random sequence and the capture domain of one or more capture probes includes random sequences. In some embodiments, probes with degenerate capture domains can be added to any of the preceding combinations listed herein. In some embodiments, probes with degenerate capture domains can be substituted for one of the probes in each of the pairs described herein.

The capture domain can be based on a gene sequence, a motif sequence or common/conserved sequence that it is designed to capture (i.e., a sequence-specific capture domain). Thus, the capture domain can be capable of binding selectively to a desired sub-type or subset of nucleic acid, for example a type or subset of mRNA. In some embodiments, a capture domain includes an "anchor" or "anchoring sequence," which is a sequence of nucleotides designed to ensure that the capture domain hybridizes to the intended mRNA. The anchor sequence can include a sequence of nucleotides, including a 1-mer, 2-mer, 3-mer or longer sequence. The sequence can be random. For example, a capture domain including a poly(T) sequence can be designed to capture an mRNA. An anchoring sequence can include a random 3-mer (e.g., GGG) that helps ensure that the poly(T) capture domain hybridizes to an mRNA. In some embodiments, an anchoring sequence can be VN, N, or NN (wherein V is A, C or G and N is an nucleotide A, C, G, T or U). Alternatively, the sequence can be designed using a specific sequence of nucleotides. In some embodiments, the anchor sequence is at the 3' end of the capture domain. In some embodiments, the anchor sequence is at the 5' end of the capture domain.

Quantification of Image Properties

In order to optimize the values of each of the foregoing parameters for permeabilization optimization, the permeabilized tissue sections are removed from the TO slides following hybridization and cDNA synthesis, leaving the cDNA synthesis products as a footprint of the captured and extended mRNA on the array slide. Photomicrographic images are taken of the hybridized cDNA synthesis products and the images are quantified in a manner that is representative of the permeabilization treatment of each tissue section. The two image properties that are of primary interest are image brightness and image sharpness. Brighter images and sharper images generally indicate higher levels of permeabilization. However, the brightest images and the sharpest images do not always occur with the same set of permeabilization conditions. In such circumstances, it may be advantageous to determine the separate permeabilization conditions that yield the brightest images and the sharpest images, and then determine a set of conditions that achieves an optimal balance of both brightness and sharpness.

In one embodiment, Fast Fourier Transform (FFT) technology can be used to quantify the brightness and sharpness of the photomicrographic images. FFT is an implementation of Discrete Fourier Transform (DFT) that can be applied to convert two-dimensional digital images from the TO array slide image domain to the frequency domain. DFT is a sampled Fourier transform that does not contain all frequencies forming an image but contains a set of frequencies large enough to mathematically describe the image from the TO array slide. FFT decomposes the digital image into its real and imaginary (sine and cosine) components that represent the image in the frequency domain. The number of frequencies in the frequency domain is equal to the number of pixels in the domain image from the TO array slide. For a square image of dimensions N×N, the two-dimensional DFT is represented by the following equation:

$$F(k, l) = \sum_{i=0}^{N-1} \sum_{j=0}^{N-1} f(i, j) e^{-i2\pi\left(\frac{ki}{N} + \frac{lj}{N}\right)}$$

In the foregoing equation, f (i, j) is the image in the spatial domain and the exponential function is the base function corresponding to each point F (k, l) in the Fourier space. In simple terms, the value of each point F (k, l) in the Fourier space is calculated by multiplying the TO image with the corresponding base function and summing the results. The basis functions are sine and cosine waves with increasing frequencies. F (0, 0) represents the DC component of the image which corresponds to the average brightness. F (N−1, N−1) represents the highest frequency and is indicative of image sharpness.

The FFT simplifies the foregoing calculations using mathematical techniques that separate the two-dimensional transform into two one-dimensional transforms, one on the horizontal direction followed by the other in the vertical direction based on the result of the horizontal transform. Yet even with this simplification, the one-dimensional FFT still has $N^2$ complexity. The FFT further simplifies the calculation by reducing the $N^2$ complexity to $N \log_2 N$. The FFT thus restricts the size of the image that can be transformed, often to $N=2^n$ where n is an integer.

Figure 3A:
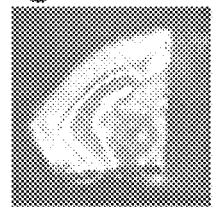
FIGS. 3a-3c show photomicrographic images of cDNA footprints from a permeabilized mouse brain tissue (FIG. 3a), masked permeabilized brain tissue (FIG. 3b), and a product of images 3a and 3b showing an image with the tissue pixel values intact (set at 1) and without the background pixel values (set at zero).
Figure 3B:
Figure 3C:
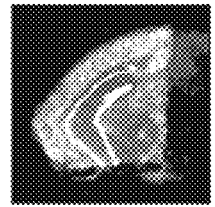

The FFT produces a complex numerical-valued output image that can be displayed with either real and imaginary (sine and cosine) parts or with magnitude and phase. Again, image magnitude is typically indicative of brightness, while image phase inversely correlates with frequency, which is indicative of image resolution or sharpness. FIGS. 3a-3c illustrate one technique for quantifying image properties. FIG. 3a is a representative photomicrographic image of a cDNA footprint taken from permeabilized mouse brain tissue. This image has both a tissue region and a background region (region around the tissue). FIG. 3b represents a mask image in which the tissue region is assigned pixel values of 1 and the background region is assigned pixel values of zero.

The mask can be obtained using various techniques for screening out the background, such as by using an intensity threshold for brightness or fluorescence of the image. FIG. 3c is a tissue image obtained by merging the original and mask images of FIGS. 3a and 3b together. In FIG. 3c, the tissue pixel values remain intact while the background pixel values are reduced to zero.

Figures 3D, 3E, 3F:
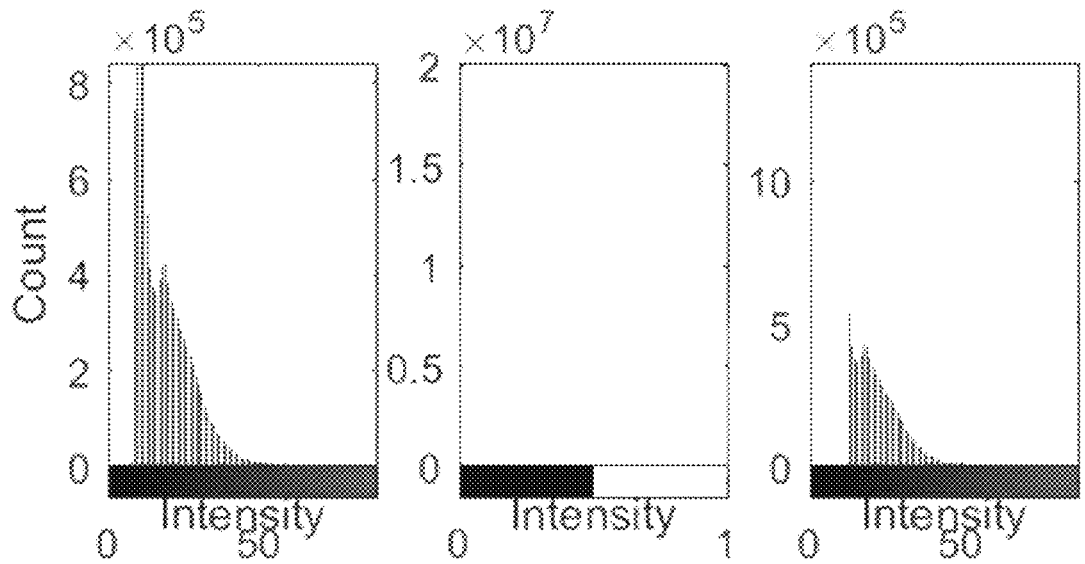
FIGS. 3d-3f are histograms of pixel counts versus pixel intensity for the images shown in FIGS. 3a-3c, respectively.

FIGS. 3d-3f are histograms of pixel count versus pixel intensity for the images in FIGS. 3a-3c, respectively. The histograms provide one method for quantifying the intensity of the images, which is representative of image brightness. The image brightness is indicative of the sensitivity of the assay to permeabilization. The FFT histograms in FIGS. 3d-3f quantify the image intensity for one permeabilized tissue section that was permeabilized using one set of parameters (one value for temperature, time, permeabilization reagent, etc.). By varying one or more of the foregoing permeabilization parameters, images like FIGS. 3a-3c and histograms like FIGS. 3d-3f can be generated to determine which value of each permeabilization parameter or combination of parameters yields the optimal brightness of the image, and therefore the optimal permeabilization condition based on optimal brightness.

The images and histograms can be generated from cDNA footprints representing a wide variety of different permeabilization conditions for a tissue type. The resulting plots and data library can then be used to correlate the image property (in this case, image brightness) with the variations in the parameter (permeabilization temperature, time, reagent type and concentration, fixing and staining agents, etc.) to determine a value for the parameter that yields an optimal level of permeabilization. The same quantification procedure can be used when evaluating different parameters and combinations of parameters (permeabilization temperature, reagents, fixing and staining agents, etc.) to determine the optimal values for each parameter and for any combination of parameters. Moreover, different metrics can be generated from the histograms, including without limitation maximum image intensity or rightness, average image intensity or brightness, and median image intensity or brightness. As explained above, iterative techniques can be employed to optimize the values of two or more parameters simultaneously.

FIGS. 4a-4c are photomicrographic images representing cDNA footprints of mouse brain tissue that has been permeabilized for 5 minutes, 15 minutes and 30 minutes, respectively, using the permeabilization conditions described above (37° C. permeabilization, methanol fixed with no staining, protease K and 10% sodium dodecyl sulfate reagents). FIG. 5 is a FFT plot of net average image intensity (AFU) versus permeabilization time. The quantitative image analysis shown in FIG. 5 is consistent with the photomicrographs (FIGS. 4a-4c) which clearly show a brighter image at 30 minutes than at 15 minutes, and a brighter image at 15 minutes than at 5 minutes.

Figure 6:
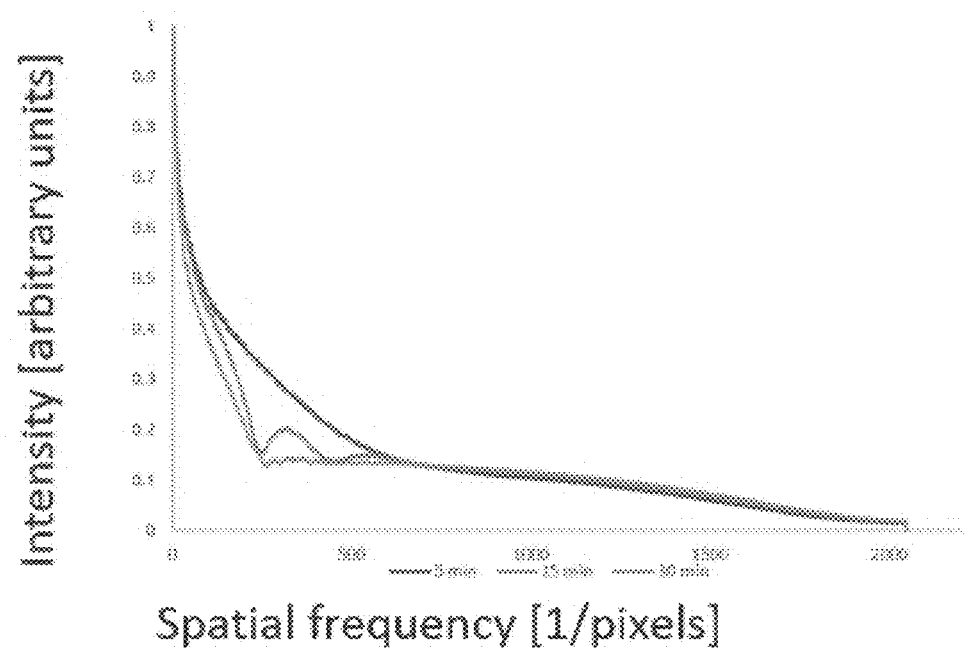
FIG. 6 shows a radial profile plot of net average image intensity (arbitrary fluorescent units) versus spatial frequency (1/pixels) for each of the images shown in FIGS. 4a-4c.

FFT images can also be used to quantify spatial frequency (frequency of sine waves over a range), which is a measure of image sharpness. This can be accomplished by processing the FFT image to extract a radial profile or a power spectrum from the FFT image. FIG. 6 includes exemplary radial profiles showing the image intensity (AFU's) versus spatial frequency (measured in units of 1/pixel length), for each of the three photomicrographs shown in FIGS. 4a-4c. The curves largely coincide except for the frequency range of about 100 to about 500 reciprocal pixels. Within that range, the image intensity of the cDNA footprint of the tissue section permeabilized for 5 minutes (upper curve) exceeds the image intensity of the cDNA footprint of the tissue section permeabilized for 15 minutes (middle curve), which in turn exceeds the image intensity of the cDNA footprint of the tissue section permeabilized for 30 minutes (lower curve). For each of the images, as the spatial frequency increases, the image intensity decreases. However, the noted difference in image intensities in the 100-500 reciprocal pixel rage indicates an overall sharper image resulting at 5 minutes permeabilization time.

Figure 7:
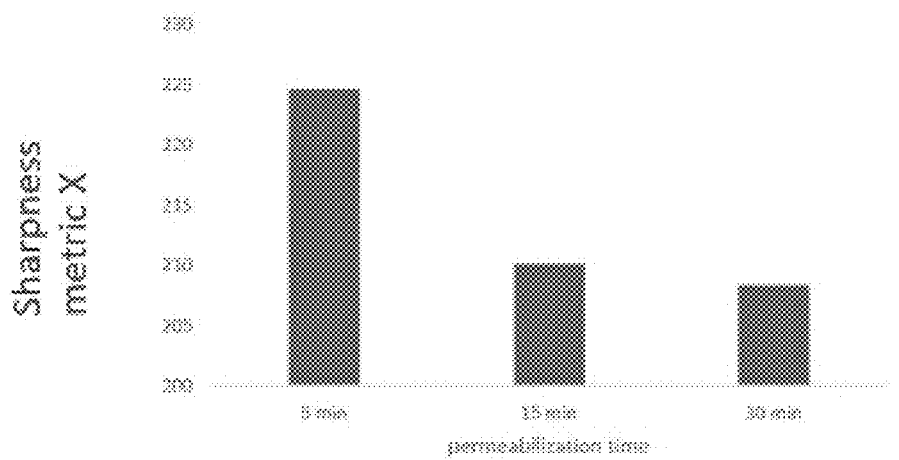
FIG. 7 shows a plot of an image sharpness metric (average spatial frequency over a selected range) versus permeabilization time for each of the images shown in FIGS. 4a-4c.

FIG. 7 is a plot of a selected sharpness metric versus permeabilization time. In this instance, the selected sharpness metric is average spatial frequency over a selected range. The average spatial frequency, which is indicative of image sharpness, is higher at the lower permeabilization time of 5 minutes than at the higher permeabilization times of 15 and 30 minutes. This is consistent with the information derived from FIG. 6.

The foregoing underscores the importance of considering both the image brightness and the image sharpness when determining optimal permeabilization conditions for a tissue section. Individual consideration of one image property to the exclusion of the other may fail to reveal that the optimal conditions for image brightness may not be the same as the optimal conditions for image sharpness. The FFT calculations reveal that the images shown in FIGS. 4a-4c become less sharp as they become brighter, as the permeabilization time is increased.

The FFT plots can be used to calculate a variety of metrics that are representative of an image property, including without limitation average frequency over a selected range of frequencies, average intensity over a selected range of frequencies, and ratio of frequencies over a plurality of selected ranges. The quantitative method of the invention can be used to optimize tissue section permeabilization for one parameter (e.g., temperature, time, reagent type and concentration, fixation agent, staining agent), for two or more parameters in sequence, for three or more parameters in sequence, for four or more parameters in sequence, or for five or more parameters in sequence. Using iterative techniques as described above, the quantitative method of the invention can also be used to optimize the permeabilization for two or more parameters simultaneously, for three or more parameters simultaneously, for four or more parameters simultaneously, or for five or more parameters simultaneously. For each of the permeabilization parameters and combinations of parameters, the method of the invention can be used to achieve an optimum image brightness, and optimum image sharpness, an optimum combination of image brightness and image sharpness, or any other image property or combination of image properties.

Additional Quantification Techniques and Examples

FIGS. 8-34 depict example results of additional techniques for quantifying image properties resulting from cDNA footprints of exemplary permeabilized tissue samples. Fixed, frozen tissue sections were placed on tissue optimization slides divided into eight rectangular capture regions 1-8, as described above with respect to FIG. 1. The permeabilization times for the tissue samples placed in each of the capture regions 1-8 were as follows: Region 1—negative control (no permeabilization), Region 2—3 minutes, Region 3—6 minutes, Region 4—12 minutes, Region 5—18 minutes, Region 6—24 minutes, Region 7—30 minutes, Region 8—36 minutes. For each example, the tissue sample was prepared, fixed, permeabilized, mRNA hybridized and fluorescently labelled cDNA synthesis products imaged using the procedure set forth in the User Guide for Visium Spatial Gene Expression Reagent Kits—Tissue Optimization, published by 10×Genomics, which is incorporated herein by reference, the permeabilization variable that was optimized was time.

Figure 8:
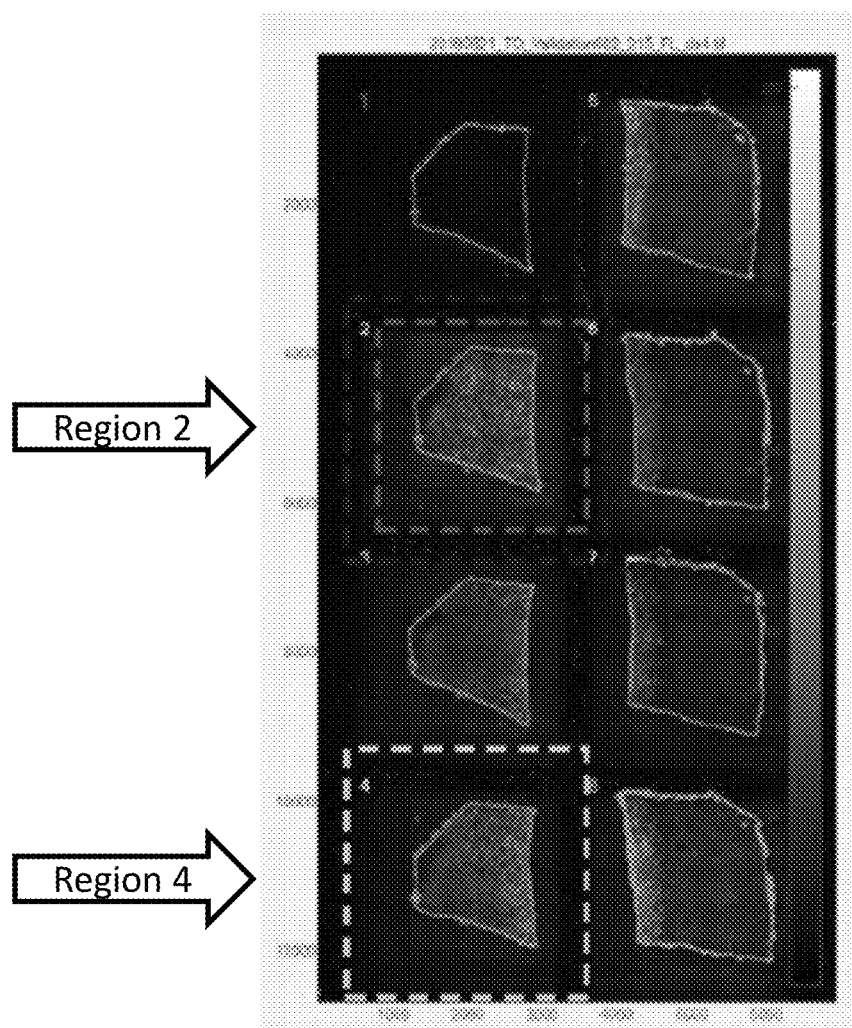
FIG. 8 shows photomicrographic images of a tissue optimization slide representing cDNA footprints of human kidney tissue as a function of permeabilization time, varied in increments from top to bottom, left to right. Region 2 was considered to have optimal brightness and sharpness. Region 4 was considered to be qualitatively optimal.

FIG. 8 provides photomicrographic images of a cDNA footprint representing permeabilization of human kidney tissue for the eight different times. The fluorescent signals were qualitatively ranked and the cDNA footprint in Region 4, representing 12 minutes permeabilization, was chosen as producing the brightest and sharpest image. However, quantitative analysis of the images revealed that the cDNA footprint in Region 2, representing 3 minutes permeabilization, produced both the brightest and the sharpest image.

Figure 9:
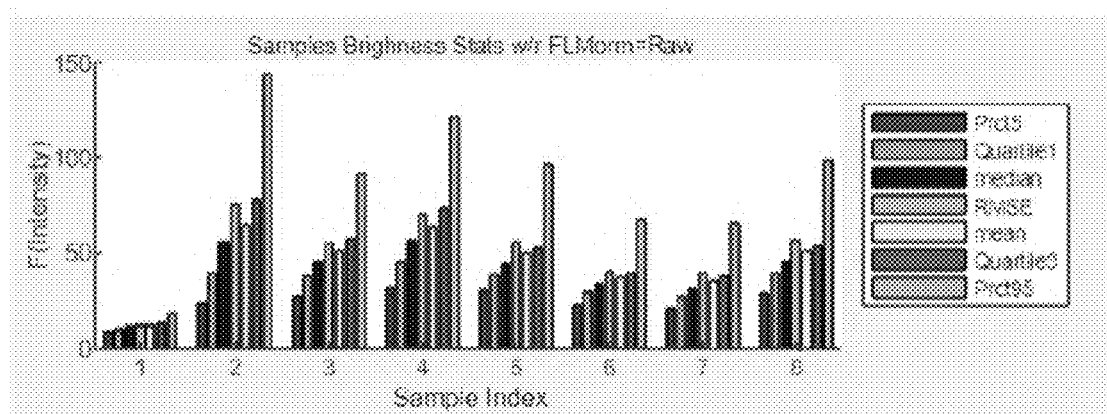
FIG. 9 is a bar graph showing pixel intensity distribution (measured in arbitrary fluorescent units, y axis) for seven statistical parameters for the eight images (x axis) from the tissue optimization slide represented in FIG. 8.

FIG. 9 is a bar graph showing pixel intensity distribution (measured in arbitrary fluorescent units) for the eight images from the tissue optimization slide represented in FIG. 8. The plots were generated from image information obtained using an inverted fluorescent microscope. The bars in each group (x-axis; Sample Indices 1-8) in the bar graph, from left to right in each group, indicate $5^{th}$ percentile, $25^{th}$ percentile, $50^{th}$ percentile, root mean square, mean, $75^{th}$ percentile and $95^{th}$ percentile. As shown in FIG. 9, the cDNA footprint from Region 2, representing 3 minutes permeabilization, produced the highest overall image intensity, representing the brightest image. Interestingly, the cDNA footprint from Region 4, representing 12 minutes permeabilization, produced the second highest overall image intensity, whereas the cDNA footprint from Region 3, representing 6 minutes permeabilization, produced less overall image intensity that the cDNA footprints from Regions 2 and 4.

FIG. 10 is a table containing normalized metrics for the eight images (columns 1-8) from the tissue optimization slide represented in FIG. 8. The metrics normalize image sharpness on a scale of zero to 1 with 1 representing the sharpest image, using 28 image sharpness algorithms (rows AMCO through WAVRA in the table). The algorithms are indicated by acronyms in FIG. 10, which have meanings according to the following Table 1. The procedures for measuring each algorithm are explained in the indicated references, each of which is public and incorporated herein by reference.

TABLE 1

Algorithms for Quantifying Image Sharpness

| Acronym | Name | Reference |
|---|---|---|
| ACMO | Absolute Central Moment | Shirvaikar, "An Optical Measure for Camera Focus and Exposure," Proceedings of the IEEE SSST (2004) |
| BREN | Brenner's function | Santos et al., "Evaluation of Autofocus Functions in Molecular Cytogenetic Analysis," J. Microscopy, Vol. 188, pt. 3 (December 1997), pp. 264-272 |
| CONT | Image contrast | Nanda et al. "Practical calibrations for a Real-Time Digital Omnidirectional Camera," Proceedings of CVPR, Technical Sketch (January 2001) |
| CONTA | Image contrast A | Nanda et al., "Practical calibrations for a Real-Time Digital Omnidirectional Camera," Proceedings of CVPR, Technical Sketch (January 2001) |
| CURV | Image curvature | Helmli et al., "Adaptive Shape from Focus with An Error Estimation in Light Microscopy," IEEE Conference Publication, ISPA (2001) |
| DCTE | DCT energy ratio | Shen et al., "Robust Focus Measure for Low Contrast Images," IEEE Digest of Technical Papers, International Conference on Consumer Electronics (2006) |
| DCTR | DCT reduced energy ratio | Lee et al., "Reduced Energy Measure Ratio for Robust Autofocusing in Digital Camera," IEEE Signal Processing Letters, Vol. 16, Issue 2 (February 2009) |
| DCTEA | DCT energy ratio A | Shen et al., "Robust Focus Measure for Low Contrast Images," IEEE Digest of Technical Papers, International Conference on Consumer Electronics (2006) |
| DCTRA | DCT reduced energy ratio A | Lee et al., "Reduced Energy Measure Ratio for Robust Autofocusing in Digital Camera," IEEE Signal Processing Letters, Vol. 16, Issue 2 (February 2009) |
| GDER | Gaussian derivative | Geusebroek et al., "Robust Autofocusing in Microscopy," Cytometry 39: 109 (2000) |
| GLVA | Graylevel variance | Krotkov et al., "Range from Focus," 1986 IEEE Conference, Vol. 3, pp. 1093-1098 (1986) |
| GLLV | Graylevel local variance | Pech-Pacheco et al., "Diatom Autofocusing in Brightfield Microscopy: A Comparative Study," IEEE Proceedings $15^{th}$ International Conference on Pattern Recognition, ICPR-2000 (2000) |
| GLVN | Normalized GLV | Santos et al., "Evaluation of Autofocus Functions in Molecular Cytogenetic Analysis," J. Microscopy, Vol. 188, pt. 3 (December 1997), pp. 264-272 |
| GRAE | Energy of gradient | Subbarao et al., "Focusing Techniques," SPIE Proceedings, Vol. 1823, Machine Vision Applications, Architectures, and Systems Integration (Nov. 1, 1992) |
| GRAT | Thresholded gradient | Santos et al., "Evaluation of Autofocus Functions in Molecular Cytogenetic Analysis," J. Microscopy, Vol. 188, pt. 3 (December 1997), pp. 264-272 |
| GRAS | Squared gradient | Eskicioglu et al., "Image Quality Measures and Their Performance," Computer Science, IEEE Trans. Communications (1995) |

TABLE 1-continued

Algorithms for Quantifying Image Sharpness

| Acronym | Name | Reference |
|---|---|---|
| HELM | Helmli's mean method | Helmli et al., "Adaptive Shape from Focus with An Error Estimation in Light Microscopy," IEEE Conference Publication, ISPA (2001) |
| HISE | Histogram entropy | Krotkov et al., "Range from Focus," 1986 IEEE Conference, Vol. 3, pp. 1093-1098 (1986) |
| HISR | Histogram range | Firestone et al., Comparison of Autofocus Methods for automated Microscopy," cytometry 12: 195-206 (1991) |
| LAPE | Energy of Laplacian | Subbarao et al., "Focusing Techniques," SPIE Proceedings, Vol. 1823, Machine Vision Applications, Architectures, and Systems Integration (Nov. 1, 1992) |
| LAPM | Modified Laplacian | Nayar, "Shape from Focus," CMU-RI-TR-89-27, Carnegie Mellon University (1989) |
| LAPV | Variance of Laplacian | Pech-Pacheco et al., "Diatom Autofocusing in Brightfield Microscopy: A Comparative Study," IEEE Proceedings $15^{th}$ International Conference on Pattern Recognition, ICPR-2000 (2000) |
| LAPD | Diagonal Laplacian | Thelen et al., "Improvements in Shape-from-Focus for Holographic Reconstructions," IEEE Transactions on Image Processing, Vol. 18, No. 1, pp. 151-157 (2009) |
| SFIL | Steerable filters | Minhas et al., "3D Shape from Focus and Depth Map computation Using Steerable Filters," ICIAR 2009: Image Analysis and Recognition, pp. 573-583 (2009" |
| SFRQ | Spatial frequency | Eskicioglu et al., "Image Quality Measures and Their Performance," Computer Science, IEEE Trans. Communications (1995) |
| TENG | Tenengrad | Krotkov et al., "Range from Focus," 1986 IEEE Conference, Vol. 3, pp. 1093-1098 (1986) |
| TENV | Tenengrad variance | Pech-Pacheco et al., "Diatom Autofocusing in Brightfield Microscopy: A Comparative Study," IEEE Proceedings $15^{th}$ International Conference on Pattern Recognition, ICPR-2000 (2000) |
| VOLA | Vollath's correlation | Santos et al., "Evaluation of Autofocus Functions in Molecular Cytogenetic Analysis," J. Microscopy, Vol. 188, pt. 3 (December 1997), pp. 264-272 |
| WAVS | Sum of Wavelet coefficients | Yang et al., "Wavelet-Based Autofocusing and Unsupervised Segmentation of Microscopic Images," IEEE Xplore Conference: Intelligent Robots and Systems, Vol. 3 (2003) |
| WAVSA | Sum of Wavelet coefficients A | Yang et al., "Wavelet-Based Autofocusing and Unsupervised Segmentation of Microscopic Images," IEEE Xplore Conference: Intelligent Robots and Systems, Vol. 3 (2003) |
| WAVV | Variance of Wavelets | Yang et al., "Wavelet-Based Autofocusing and Unsupervised Segmentation of Microscopic Images," IEEE Xplore Conference: Intelligent Robots and Systems, Vol. 3 (2003) |
| WAVR | Multi-level two-dimensional inverse FWT | Gonzalez et al., "Digital Image Processing Using MATLAB," Prentice-Hall, 2004 Revision |
| WAVRA | Multi-level two-dimensional inverse FWT A | Gonzalez et al., "Digital Image Processing Using MATLAB," Prentice-Hall, 2004 Revision |

As shown in FIG. 10, the "Region 2" (sample 2) cDNA footprint (3 minutes permeabilization time) yielded the best image sharpness in 23 of the 28 algorithms. The "Region 4" (sample 4) cDNA footprint (12 minutes permeabilization time) yielded the second-best image sharpness according to most of the algorithms.

Figure 11:
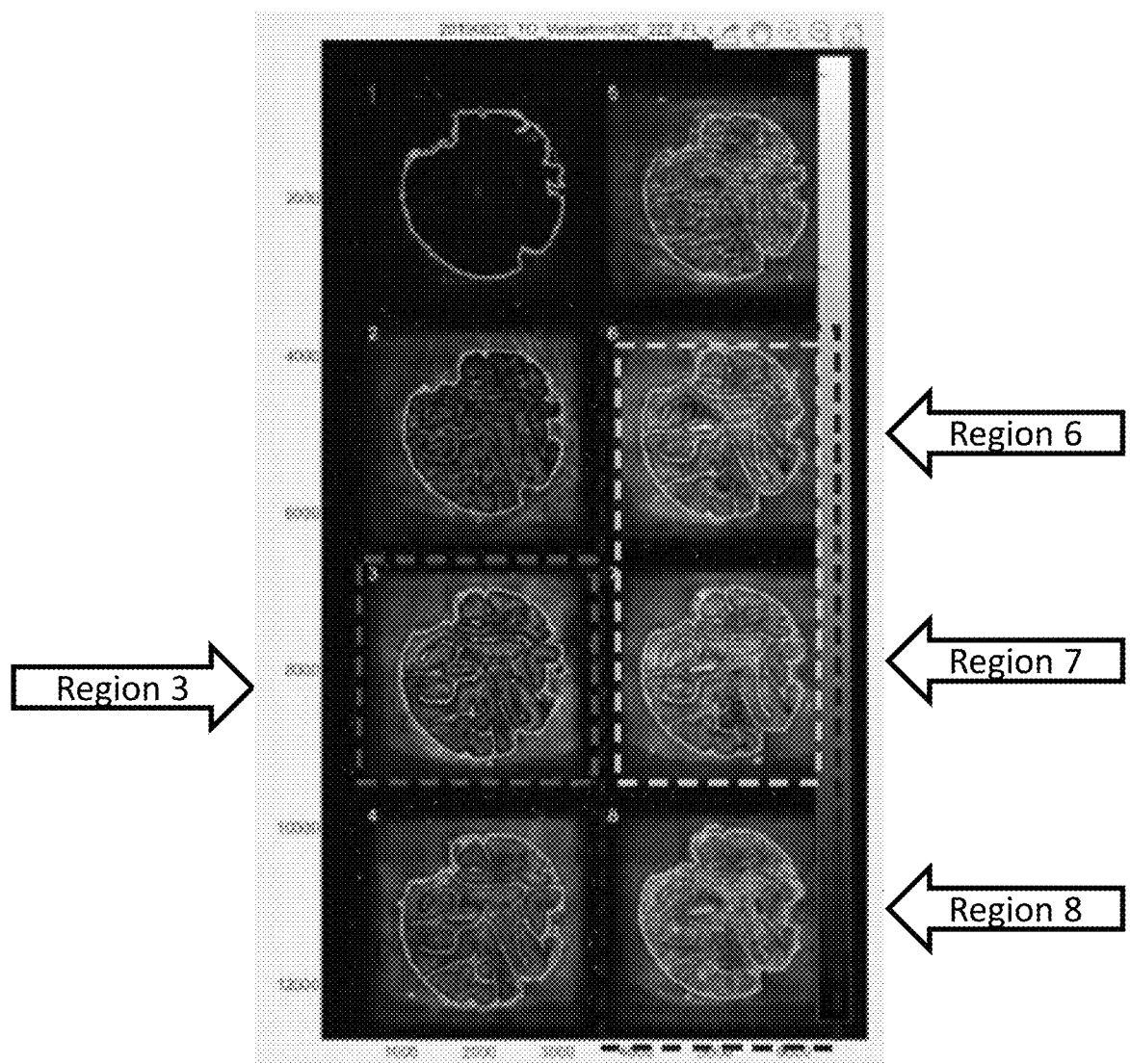
FIG. 11 shows photomicrographic images of a tissue optimization slide representing cDNA footprints of human small intestine tissue as a function of permeabilization time, varied in increments from top to bottom, left to right. Region 3 was considered to have optimal sharpness. Regions 6-8 were considered to have optimal brightness. Regions 6 and 7 were considered to be qualitatively optimal.

FIG. 11 provides photomicrographic images of cDNA footprints resulting from permeabilization of samples of human small intestine tissue for the eight different times: Region 1—negative control (no permeabilization), Region 2—3 minutes, Region 3—6 minutes, Region 4—12 minutes, Region 5—18 minutes, Region 6—24 minutes, Region 7—30 minutes, Region 8—36 minutes. Each tissue sample was prepared, fixed, permeabilized, hybridized and imaged using the procedure set forth in the above-identified User Guide for Visium Spatial Gene Expression Reagent Kits—Tissue Optimization, time was again the permeabilization variable.

Referring to FIG. 11, the eight permeabilization conditions were qualitatively ranked and the images of the cDNA footprints in Regions 6 and 7, representing 24 minutes and 30 minutes permeabilization, respectively, were chosen as producing the brightest and sharpest images. However, quantitative analysis of the images revealed that the cDNA footprint in Region 3, representing 6 minutes permeabilization, produced the sharpest image, and that the cDNA footprint in Regions 6-8, representing 24-36 minutes permeabilization, produced the brightest images.

Figure 12:
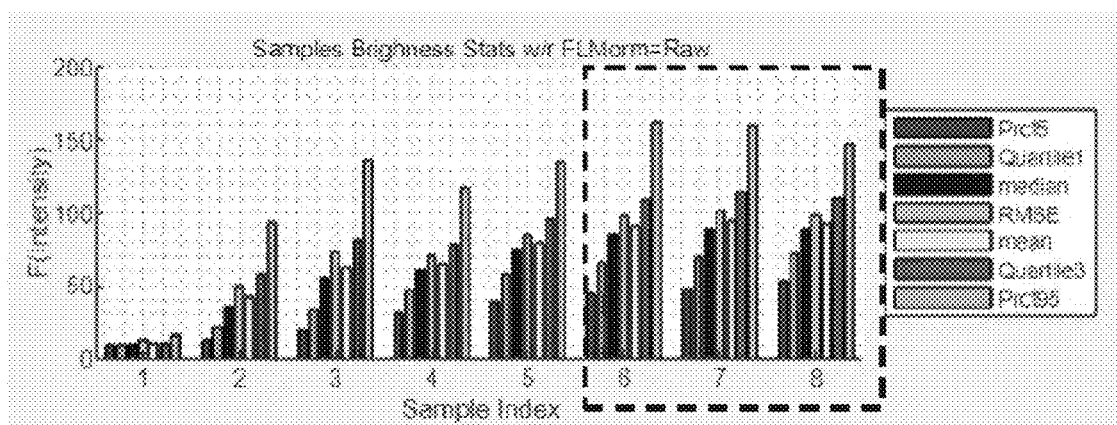
FIG. 12 is a bar graph showing pixel intensity distribution (measured in arbitrary fluorescent units, y axis) for seven statistical parameters of the eight images (x axis) from the tissue optimization slide represented in FIG. 11.

FIG. 12 is a bar graph showing pixel intensity distribution (measured in arbitrary fluorescent units) for the eight images generated in FIG. 11. The plots were generated from image information obtained using an inverted fluorescent microscope. The bars in each group (x-axis; Sample Indices 1-8) in the bar graph, from left to right in each group, indicate $5^{th}$ percentile, $25^{th}$ percentile, $50^{th}$ percentile, root mean square, mean, $75^{th}$ percentiles and $95^{th}$ percentile. As shown in FIG. 12, the cDNA footprints in Regions 6 and 7, representing 24 and 30 minutes permeabilization, respectively, produced the greatest overall image intensity, indicating the brightest images. The cDNA footprint in Region 8, representing 36 minutes permeabilization, produced almost as much overall image intensity (brightness) as the cDNA footprints in Regions 6 and 7.

FIG. 13 is a table containing normalized metrics for the eight images (columns 1-8) from the tissue optimization slide represented in FIG. 11, that normalizes image sharpness on a scale of zero to 1 using the 28 image sharpness algorithms described above (rows AMCO through WAVRA in the table). As shown in FIG. 13, the "Region 3" cDNA footprint (6 minutes permeabilization time) produced the highest image sharpness in 26 of the 28 algorithms. The "Region 6" cDNA footprint (24 minutes permeabilization time) produced the second-best image sharpness according to most of the algorithms.

Figure 14:
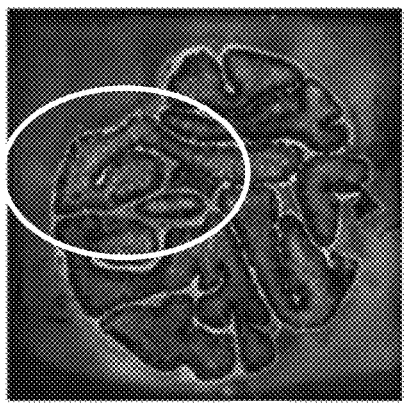
FIGS. 14 and 15 show magnifications of the sharpest image from the tissue optimization slide represented in FIG. 11, taken from Region 3 (6 minutes permeabilization time).
Figure 15:
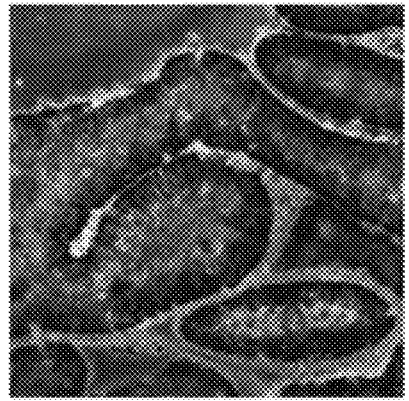
Figure 16:
FIGS. 16 and 17 show magnifications of the brightest image from the tissue optimization slide represented in FIG. 11, taken from Region 6 (24 minutes permeabilization time).
Figure 17:

FIGS. 14 and 15 show magnifications of the sharpest image resulting from cDNA footprints of the permeabilized small intestine tissue, taken from Region 3 (6 minutes permeabilization time). FIGS. 16 and 17 show magnifications of the brightest image resulting from cDNA footprints of the permeabilized small intestine tissue, taken from Region 6 (24 minutes permeabilization time). Both the sharpest and the brightest images are useful in visualizing the degree of mRNA and subsequent cDNA synthesis on the tissue optimization slide.

Figure 18:
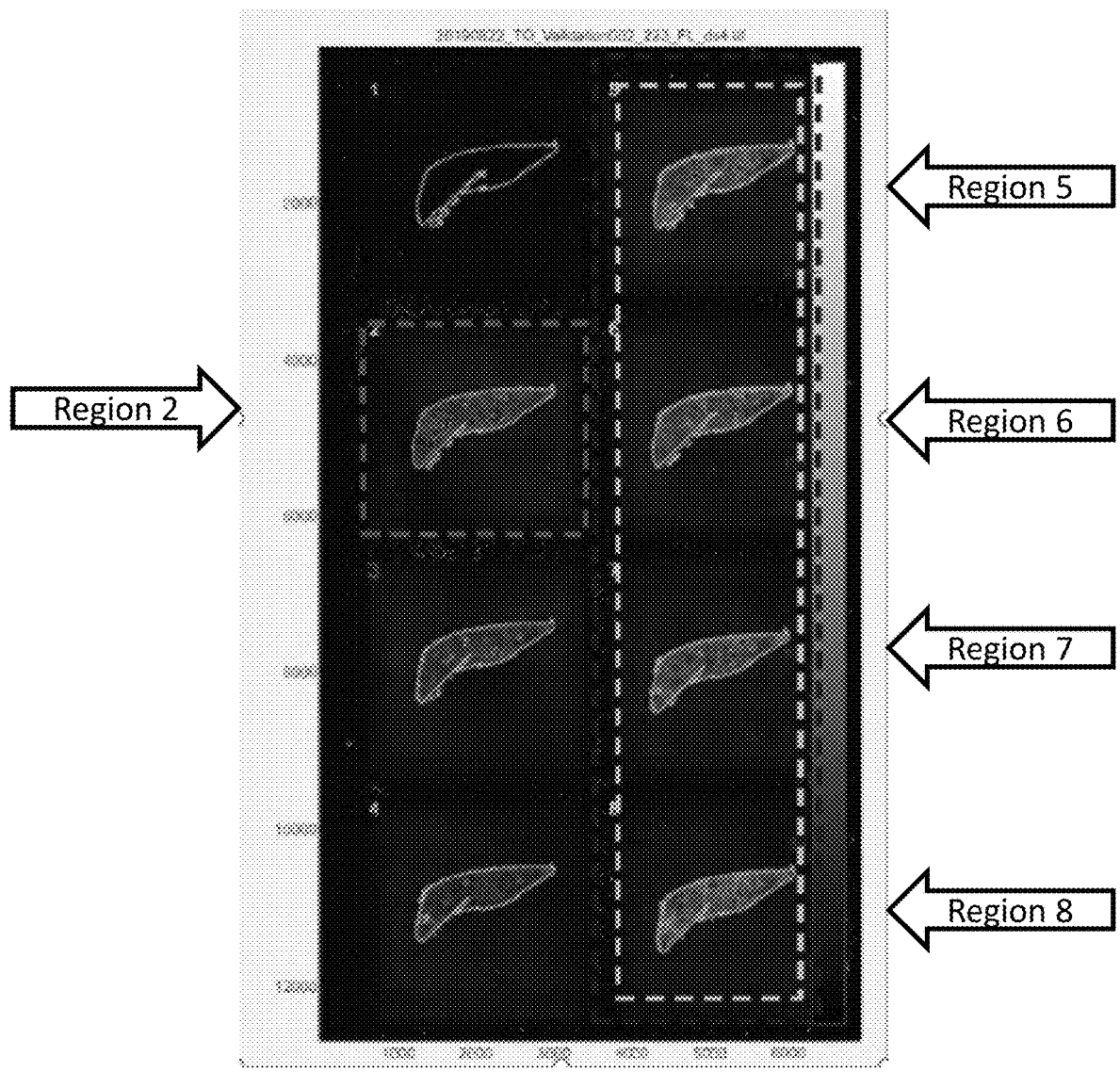
FIG. 18 shows photomicrographic images of a tissue optimization slide representing cDNA footprints of mouse lung tissue as a function of permeabilization time, varied in increments from top to bottom, left to right. Region 2 was considered to have optimal sharpness. Regions 5-8 were considered to have optimal brightness and to be qualitatively optimal.

FIG. 18 provides photomicrographic images of cDNA footprints resulting from permeabilization of samples of mouse lung tissue for the eight different times: Region 1—negative control (no permeabilization), Region 2—3 minutes, Region 3—6 minutes, Region 4—12 minutes, Region 5—18 minutes, Region 6—24 minutes, Region 7—30 minutes, Region 8—36 minutes. Each tissue sample was prepared, fixed, permeabilized, hybridized and imaged using the procedure set forth in the above-identified User Guide for Visium Spatial Gene Expression Reagent Kits—Tissue Optimization, the permeabilization time was varied.

Referring to FIG. 18, the eight conditions were qualitatively ranked and the cDNA footprints in Regions 5, 6, 7 and 8, representing 18 minutes, 24 minutes, 30 minutes and 36 minutes permeabilization, respectively, were chosen as producing the brightest and sharpest images. However, quantitative analysis of the images revealed that the cDNA footprint in Region 2, representing 3 minutes permeabilization, produced the sharpest image, and that the tissue samples in Regions 5-8, representing 18-36 minutes permeabilization, produced the brightest images.

Figure 19:
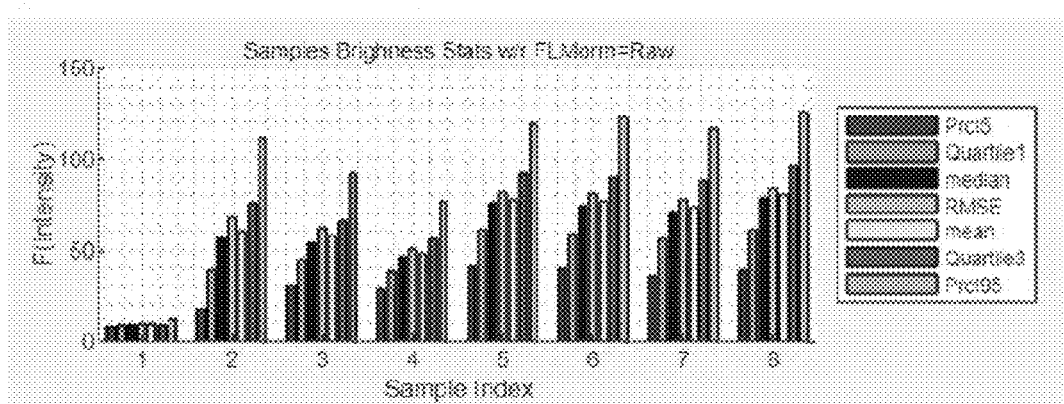
FIG. 19 is a bar graph showing pixel intensity distribution (measured in arbitrary fluorescent units, y axis) of seven statistical parameters for the eight images (x axis) from the tissue optimization slide represented in FIG. 18.

FIG. 19 is a bar graph showing pixel intensity distribution (measured in arbitrary fluorescent units) for the eight images represented in FIG. 18. The plots were generated from image information obtained using an inverted fluorescent microscope. The bars in each group (x-axis; Sample Indices 1-8) in the bar graph, from left to right in each group, indicate $5^{th}$ percentile, $25^{th}$ percentile, $50^{th}$ percentile, root mean square, mean, $75^{th}$ percentiles and $95^{th}$ percentile. As shown in FIG. 19, the cDNA footprints in Regions 5, 6, 7 and 8, representing 18, 24, 30 and 36 minutes permeabilization, respectively, produced the greatest overall image intensities, indicating the brightest images. The cDNA footprint in Region 8, representing 36 minutes permeabilization, produced slightly better overall image intensity (brightness) than the cDNA footprints in Regions 5, 6 and 7.

FIG. 20 is a table containing normalized metrics for the eight images (columns 1-8) represented in FIG. 18 that normalizes image sharpness on a scale of zero to 1, measured using the 28 image sharpness algorithms described above (rows AMCO through WAVRA in the table). As shown in FIG. 20, the "Region 2" cDNA footprint (3 minutes permeabilization time) produced the best image sharpness in 19 of the 28 algorithms. The "Region 6" cDNA footprint (24 minutes permeabilization time) produced the second-best image sharpness according to most of the algorithms.

Figures 21, 22:
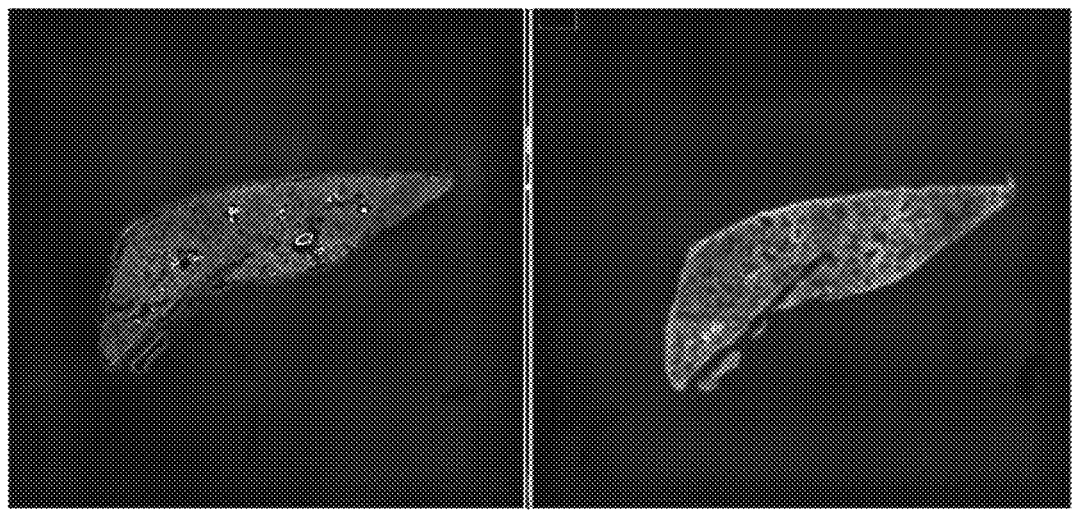
FIG. 21 shows a magnification of the sharpest image from the tissue optimization slide represented in FIG. 18, taken from Region 2 (3 minutes permeabilization time).
FIG. 22 shows a magnification of one of the brightest images from the tissue optimization slide represented in FIG. 18, taken from Region 5 (18 minutes permeabilization time).

FIGS. 21 and 22 show magnifications of the sharpest image represented in FIG. 18, taken from Region 2 (3 minutes permeabilization time), and one of the brightest images represented in FIG. 18, taken from Region 5 (18 minutes permeabilization time). Again, both the sharpest and the brightest images are useful in visualizing the degree of mRNA capture and subsequent cDNA synthesis on the tissue optimization slide.

Figure 23:
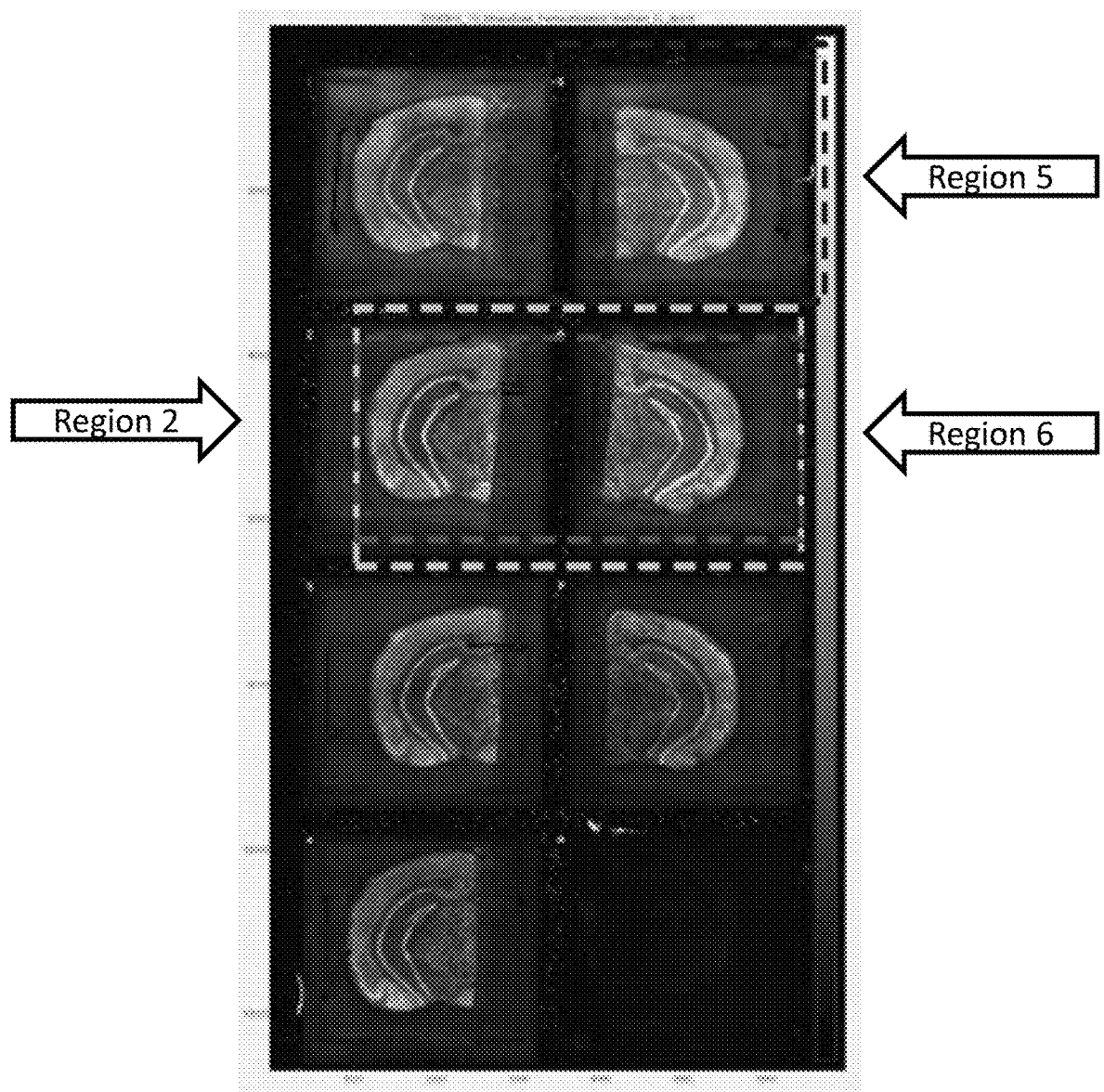
FIG. 23 shows photomicrographic images of a tissue optimization slide representing cDNA footprints of mouse brain tissue as a function of permeabilization time, varied in increments from top to bottom, left to right. Regions 2 and 6 were considered to have optimal sharpness and to be qualitatively optimal. Region 5 was considered to have optimal brightness.

FIG. 23 provides photomicrographic images of cDNA footprints resulting from permeabilization of samples of mouse brain tissue for the eight different times: Region 1—negative control (no permeabilization), Region 2—3 minutes, Region 3—6 minutes, Region 4—12 minutes, Region 5—18 minutes, Region 6—24 minutes, Region 7—30 minutes, Region 8—36 minutes. Each tissue sample was prepared, fixed, permeabilized, hybridized and imaged using the procedure set forth in the above-identified User Guide for Visium Spatial Gene Expression Reagent Kits—Tissue Optimization, permeabilization time was varied.

Referring to FIG. 23, the eight images were qualitatively ranked and the cDNA footprints in Regions 2 and 6, permeabilized for 3 minutes and 24 minutes, respectively, were chosen as producing the brightest and sharpest images. However, quantitative analysis of the images revealed that the cDNA footprint in Region 5, representing 18 minutes permeabilization, produced the brightest image, and that the CDNA footprints in Regions 2 and 6, representing 3 minutes and 24 minutes permeabilization, produced the sharpest images.

Figure 24:
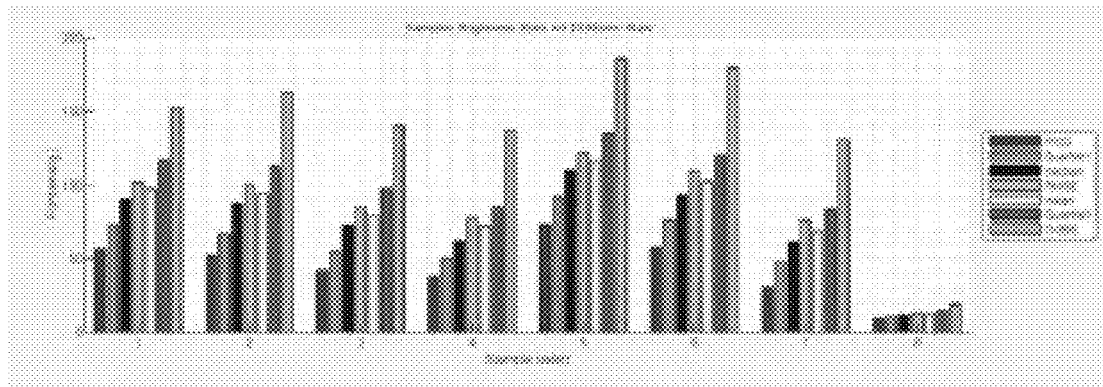
FIG. 24 is a bar graph showing pixel intensity distribution (measured in arbitrary fluorescent units, y axis) for seven statistical parameters of the eight images (x axis) from the tissue optimization slide represented in FIG. 23.

FIG. 24 is a bar graph showing pixel intensity distribution (measured in arbitrary fluorescent units) for the eight images represented in FIG. 23. The plots were generated from image information obtained using an inverted fluorescent microscope. The bars in each group (x-axis; Sample Indices 1-8) in the bar graph, from left to right in each group, indicate $5^{th}$ percentile, $25^{th}$ percentile, $50^{th}$ percentile, root mean square, mean, $75^{th}$ percentiles and $95^{th}$ percentile. As shown in FIG. 24, the cDNA footprints in Regions 5, representing 18 minutes permeabilization, produced the greatest overall image intensity, indicating the brightest image. The cDNA footprint in Region 6, representing 24 minutes permeabilization, produced a close second-place for image brightness.

FIG. 25 is a table containing normalized metrics for the eight images (columns 1-8) represented in FIG. 23 that normalizes image sharpness on a scale of zero to 1, measured using the 28 image sharpness algorithms described above (rows AMCO through WAVRA in the table). As shown in FIG. 25, the "Region 6" cDNA footprint (24 minutes permeabilization time) produced the best image sharpness in 24 of the 28 algorithms. The "Region 2" cDNA footprint (3 minutes permeabilization time) produced the second-best image sharpness according to most of the algorithms.

Figure 26:
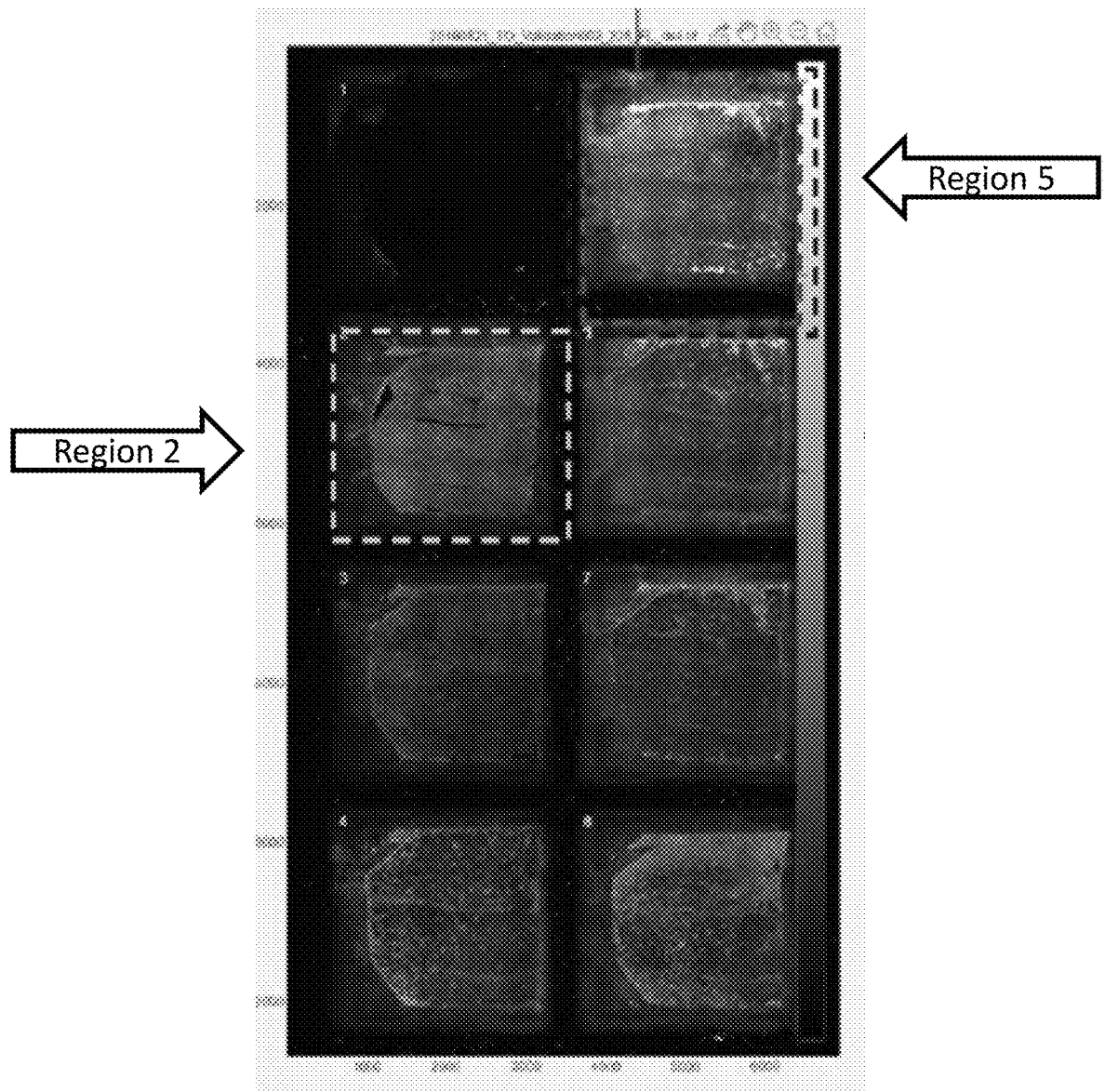
FIG. 26 shows photomicrographic images of a tissue optimization slide representing cDNA footprints of human liver tissue as a function of permeabilization time, varied in increments from top to bottom, left to right. Region 2 was considered to be qualitatively optimal. Region 5 was considered to have optimal brightness and sharpness.

FIG. 26 provides photomicrographic images of cDNA footprints resulting from permeabilization of samples of human liver tissue for the eight different times: Region 1—negative control (no permeabilization), Region 2—3 minutes, Region 3—6 minutes, Region 4—12 minutes, Region 5—18 minutes, Region 6—24 minutes, Region 7—30 minutes, Region 8—36 minutes. Each tissue sample was prepared, fixed, permeabilized, hybridized and imaged using the procedure set forth in the above-identified User Guide for Visium Spatial Gene Expression Reagent Kits—Tissue Optimization, permeabilization time was varied.

Referring to FIG. 26, the eight images were qualitatively ranked and the cDNA footprint in Region 2, representing 3 minutes permeabilization, was chosen as producing the brightest and sharpest image. However, quantitative analysis of the images revealed that the cDNA footprint in Region 5, representing 18 minutes permeabilization, yielded the brightest and the sharpest image.

Figure 27:
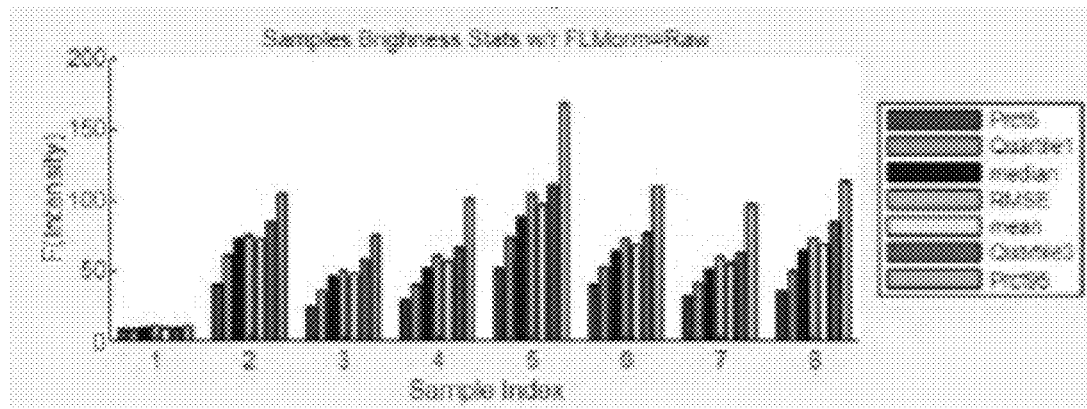
FIG. 27 is a bar graph showing pixel intensity distribution (measured in arbitrary fluorescent units, x axis) for seven statistical parameters of the eight images (y axis) from the tissue optimization slide represented in FIG. 26.

FIG. 27 is a bar graph showing pixel intensity distribution (measured in arbitrary fluorescent units) for the eight images represented in FIG. 26. The plots were generated from image information obtained using an inverted fluorescent microscope. The bars in each group (x-axis; Sample Indices 1-8) in the bar graph, from left to right in each group, indicate $5^{th}$ percentile, $25^{th}$ percentile, $50^{th}$ percentile, root mean square, mean, $75^{th}$ percentiles and $95^{th}$ percentile. As shown in FIG. 27, the cDNA footprint in Region 5, representing 18 minutes permeabilization, produced the greatest overall image intensity, indicating the brightest image. There was no close second-place image.

Figure 28:
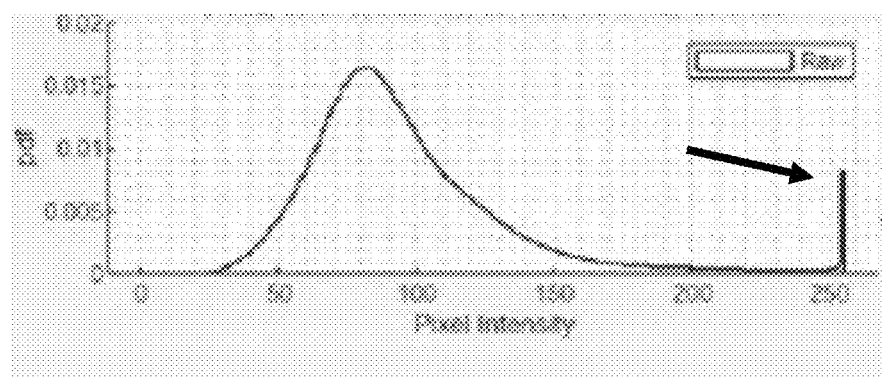
FIG. 28 is a histogram of pixel intensity (x axis) versus pixel count (y axis) for the brightest image from the tissue optimization slide of FIG. 26, taken from Region 5 (18 minutes permeabilization time).

FIG. 28 is a histogram of pixel intensity versus pixel count for the brightest image represented in Region 5 of FIG. 26. The arrow points to saturated pixels having an intensity of about 260 arbitrary fluorescent units. The existence of saturated pixels diminishes the reliability of the quantitative image analysis and indicates the need for adjustments to the magnification, filtering, and/or other controls when taking the image.

FIG. 29 is a table containing normalized metrics for the eight images (columns 1-8) represented in FIG. 26 that normalizes image sharpness on a scale of zero to 1, measured using the 28 image sharpness algorithms described above (rows AMCO through WAVRA in the table). As shown in FIG. 29, the "Region 5" cDNA footprint (18 minutes permeabilization time) produced the best image sharpness in 26 of the 28 algorithms. There was no close second-place image.

Figure 30:
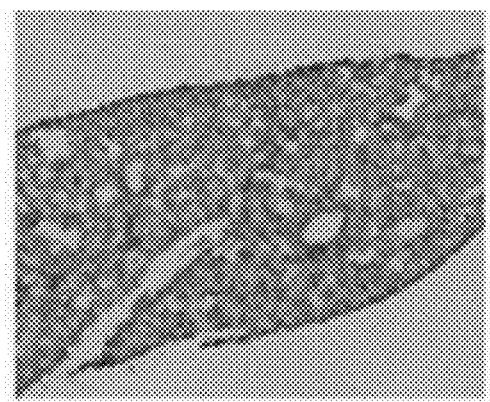
FIGS. 30 and 31 represent the transformation of a photomicrographic image (FIG. 30) of a cDNA footprint on a tissue optimization slide into a spot image (FIG. 31), according to one embodiment of the invention, using original and spot cDNA footprints of permeabilized mouse lung tissue.
Figure 31:
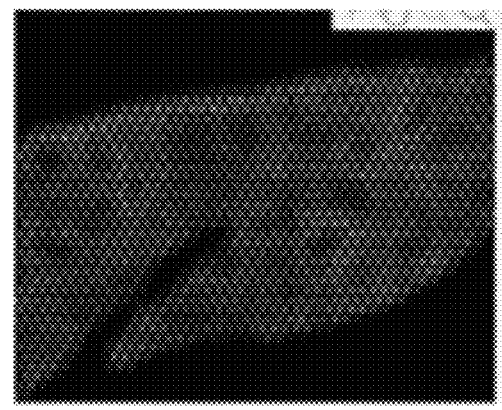

FIGS. 30-34 represent a quantification technique in which an original photomicrographic image of a cDNA footprint of a permeabilized tissue sample could be transformed into a spot image (FIG. 31) for further analysis and quantification. FIGS. 30 and 31 are original and spot images, respectively, of a cDNA footprint of a permeabilized mouse lung tissue section. Transformation of the photomicrographic image into a representative spot image can be accomplished using a variety of known techniques.

Figure 32:
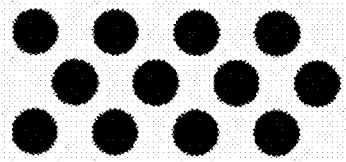
FIG. 32 schematically represents an exemplary array of spots taken from a section of a spot image.
Figure 33:
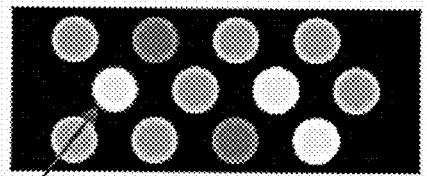
FIG. 33 schematically represents an exemplary first technique for quantifying an array of image spots.

Once the image is transformed, any portion of the spot image can be represented by an array of spots having a size and spacing (pitch), as shown in FIG. 32. In a first embodiment of the spot quantification technique, shown in FIG. 33, the average pixel value (image intensity) of an individual spot, represented by the arrow, can be calculated as the average pixel value of all pixels within each spot. The pixel values of the spaces between the spots are set at zero, and only the average pixel values of the pixels covered by the individual spots are determined. Each spot can thus have an average pixel value that represents the brightness of the portion of the image covered by the spot.

Figure 34:
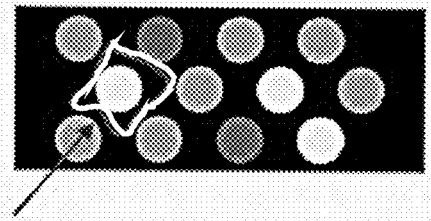
FIG. 34 schematically represents an exemplary second technique for quantifying an array of image spots.

In a second embodiment of the spot quantification technique, shown in FIG. 34, the average pixel value of an individual spot, represented by the arrow, takes into account the average pixel value of both a) the pixels within each spot, and b) the pixels that are outside the spot but within a defined vicinity of the spot (inside the white traced area). Each spot can be assigned an average pixel value that represents the portions of the image covered by the spot and adjacent to the spot.

Figure 35A:
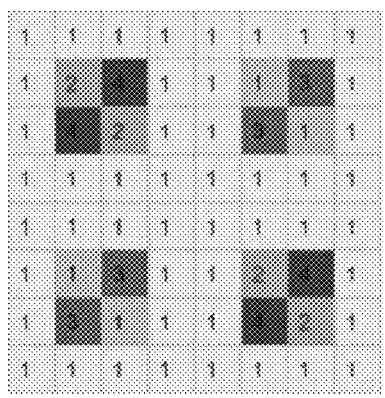
FIGS. 35a and 35b schematically represent another example of the first technique for quantifying an array of image spots, derived from original and spot images of cDNA footprints of permeabilized mouse lung tissue, examples seen in FIG. 30 and FIG. 31.
Figure 35B:
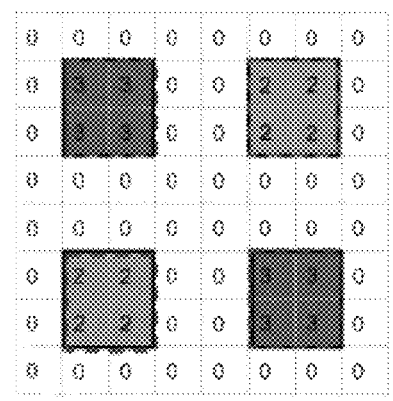

FIGS. 35a and 35b represent one example of pixel averaging according to the first embodiment of the spot quantification technique, based on original and spot images of cDNA footprints of a mouse lung tissue. Referring to FIG. 35a, each spot contained four pixels and had a spot diameter of 50 microns, and the pitch (spacing between spots) averaged 60 microns. Referring to FIG. 35b, only the pixel values within each spot were averaged, while the pixels between the spots were assigned values of zero and not included in the averages. This resulted in an average pixel value of 3 for the upper left spot (the average of 2, 4, 2 and 4), an average pixel value of 3 for the upper right spot (the average of 1, 3, 1, 3), an average pixel value of 2 for the lower left hand spot (the average of 1, 3, 1 and 3), and an average pixel value of 3 for the lower right hand spot (the average of 2, 4, 2 and 4).

Figure 36A:
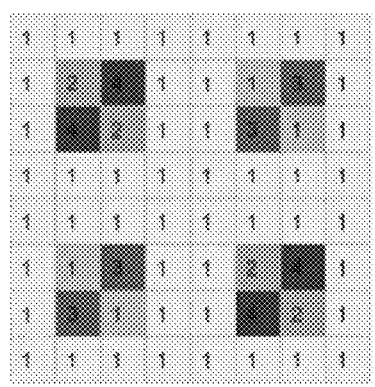
FIGS. 36a and 36b schematically represent another example of the second technique for quantifying an array of image spots, derived from original and spot images of cDNA footprints of permeabilized mouse lung tissue, examples seen in FIG. 30 and FIG. 31.
Figure 36B:
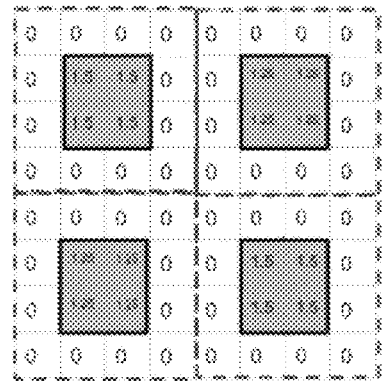

FIGS. 36a and 36b represent one example of pixel averaging according to the second embodiment of the spot quantification technique, based on original and spot images of cDNA footprints of a mouse lung tissue. Referring to FIG. 36a, each spot contained four pixels and had a spot diameter of 50 microns, and the pitch (spacing between spots) averaged 60 microns. Referring to FIG. 36b, the pixels between the spots were again assigned values of zero. However, the average pixel values for each of the spots included not only the pixels within each spot but the original first layer of pixels surrounding each spot, each having values of 1 as shown in FIG. 36a. This resulted in an average pixel value of 1.5 for the upper left spot (the average of 2, 4, 2, 4, 1, 1, 1, 1, 1, 1, 1, 1, 1 and 1), an average pixel value of 1.25 for the upper right spot (the average of 1, 3, 1, 3, 1, 1, 1, 1, 1, 1, 1, 1, 1, 1 and 1), an average pixel value of 1.25 for the lower left hand spot (the average of 1, 3, 1, 3, 1, 1, 1, 1, 1, 1, 1, 1, 1 and 1), and an average pixel value of 1.5 for the lower right hand spot (the average of 2, 4, 2, 4, 1, 1, 1, 1, 1, 1, 1, 1, 1 and 1).

Implementation

As explained above, the method of the invention generates a large amount of data for each image on a single tissue optimization slide. Several tissue optimization slides may need to be analyzed in order to optimize permeabilization based on all the pertinent parameters and image properties, and for each of the various cellular tissues. In order to maintain the data in a useful format for current and future use, the optimum values that are generated for each permeabilization parameter and image property, and for each cellular tissue type, are implemented in a way that enables their storage and avoids unnecessary repetition of the method steps. The optimum values for each parameter and each combination of parameters, generated for each image property and each combination of image properties, and for each cellular tissue, may be implemented by storing them in an instrument such as a computer database or, preferably, a computer that has both a database and the capability of further analysis and optimization of the input information.

Accordingly, the present invention includes an instrument for quantitatively optimizing the permeabilization of cellular tissues used for spatial transcriptomics. The instrument includes an apparatus (such as a computer database) for receiving and storing data for at least one parameter that influences permeabilization in a tissue section. Preferably, the instrument includes apparatus for receiving and storing data for two or more parameters, three or more parameters, four or more parameters, or five or more parameters that influence permeabilization in the cellular tissue. The instrument further includes apparatus (such as a computer program) for correlating variations in the at least one parameter with at least one image property that is determinative of permeabilization in the tissue section. The instrument further includes apparatus for determining an optimum m value for the at least one parameter based on the correlation between variations in the parameter and the image property, and apparatus for storing the optimum value of the at least one parameter. Finally, the instrument includes apparatus for informing a user of the optimum value of the at least one parameter.

The apparatus for receiving and storing data can be configured and/or programmed for receiving and storing data for multiple parameters in sequence or simultaneously. The apparatus for informing the user can be configured and/or programmed to inform the user of the optimum values for each of the multiple parameters. Suitably, consistent with the method described herein, the apparatus for receiving and storing data includes apparatus for receiving and storing FFT image data. The apparatus for correlating variations in the at least one parameter with at least one image property can suitably be configured and/or programmed to correlate variations in the at least one parameter with multiple image properties, either in sequence or simultaneously. The multiple image properties can be selected from image brightness, image sharpness, combinations of image brightness and image sharpness, and additional image properties and combinations thereof.

That apparatus for informing a user of the optimum value of the at least one parameter, and/or the optimum values for multiple parameters, can be a computer screen (such as a desktop or laptop screen), a smartphone screen, an audio device with an artificial voice, a voice-activated device, a hand-held tablet, or any combination thereof. As the database inside the instrument gathers and stores increasing amounts of data for different permeabilization conditions and different types of tissue samples, the instrument becomes more and more reliable as a reference source for optimal permeabilization conditions.

Notwithstanding the foregoing description or the appended claims, the disclosure set forth herein is also defined by the following numbered clauses, which may be beneficial alone or in combination, with one or more other causes or embodiments. Each of these individually numbered clauses may be used or combined with any of the preceding or following clauses. Thus, these clauses are intended to provide support for all such combinations and is not necessarily limited to specific combinations explicitly provided below:

1. A quantitative method of optimizing the permeabilization of tissue samples used for spatial transcriptomics, comprising the steps of:
    a) selecting at least one parameter that affects permeabilization of the tissue sample;
    b) preparing a plurality of sections of the tissue sample for permeabilization;
    c) permeabilizing the sections of the tissue sample, wherein the permeabilization parameter is varied for the different tissue sections during permeabilization;
    d) generating a cDNA footprint of each of the permeabilized tissue sections;
    e) imaging the cDNA footprints;
    f) determining a level of permeabilization for each tissue section by quantifying at least one image property that is determinative of the level of permeabilization; and
    g) correlating the at least one image property with the variations of the permeabilization parameter to determine a value for the parameter that indicates an optimum level of the permeabilization parameter, thereby optimizing the permeabilization conditions for the tissue sample.
2. The method of clause 1, wherein preparing a plurality of tissue sections comprises placing each tissue section on a separate area on a slide, wherein the slide comprises a plurality of array areas for placing tissue sections, and each array area comprising a plurality of capture probes immobilized thereon.
3. The method of clause 2, wherein the plurality of capture probes comprise capture domains and after permeabilization analytes are released from the tissue sections and a plurality of the released analytes hybridize to the capture domains.
4. The method of any one of clauses 1-3, wherein the cDNA footprint is generated by extending the capture domains of the capture probes using the hybridized analytes as a template to create cDNA molecules of the hybridized analytes.
5. The method of clause 4, wherein the capture domain is extended enzymatically in the presence of one or more fluorescently labelled nucleotides, dATP, dCTP, dGTP or dTTP.
6. The method of any one of clauses 1-4, wherein the cDNA footprint is generated by hybridizing a primer that is complementary to the analytes hybridized to the capture domains and extending the primer enzymatically using the analytes as a template to create cDNA molecules of the hybridized analytes.
7. The method of any one of clauses 3-6, wherein the analyte is DNA or RNA.
8. The method of clause 7, wherein RNA is mRNA.
9. The method of any one of clauses 2-8, wherein the capture domains comprise a poly(T) sequence, a poly (T) random sequence, a random nucleic acid sequence, a semi-random nucleic acid sequence or a non-random nucleotide sequence.
10. The method of any one of clauses 1-9, wherein the at least one parameter selected is permeabilization time, permeabilization temperature, type of permeabilization reagent, a fixing agent used to fix the cellular tissue before permeabilization, and a staining agent used to stain the cellular tissue before permeabilization.
11. The method of clause 10, wherein the permeabilization time is varied in selected increments between about 5 minutes and about 60 minutes.
12. The method of clause 10, wherein the permeabilization temperature is varied in selected increments between about 4 degrees and about 50 degrees C.
13. The method of clause 10, wherein the type of permeabilization reagent is varied between one or more of organic solvents, cross-linking agents, detergents, enzymes, lysis reagents, and combinations thereof.

14. The method of clause 13, wherein the organic solvent is varied between two or more of acetone, methanol, ethanol, and combinations thereof.

15. The method of clause 13, wherein the crosslinking agent is varied between paraformaldehyde, glutaraldehyde, and combinations thereof.

16. The method of clause 13, wherein the detergent is varied between two or more of saponin, Triton X-100™ ($C_{14}$—$H_{22}$—O—($C_2$—$H_4$—O)$_n$), Tween-20™ (polyoxyethylene sorbitan monolaurate), sodium dodecyl sulfate, N-lauroylsarcisine, N-lauroylsarcisine sodium salt, and combinations thereof.

17. The method of clause 13, wherein the enzyme is varied between trypsin, proteases, and combinations thereof.

18. The method of clause 13, wherein the lysis reagent is varied between two or more of lysozymes, achromopeptidase, lysostaphin, labiase, kitalase, lyticase, and combinations thereof.

19. The method of any one of clauses 13-18, wherein the permeabilization reagent further comprises varying the concentration of the permeabilization reagent.

20. The method of clause 19, wherein the concentration of permeabilization agent is varied in increments between about 1.0% w/v and about 15% w/v.

21. The method of clause 10, wherein the fixing agent is varied between two or more of an alcohol, ketone, aldehyde, cross-linking agent, disuccinimidyl suberate (DSS), dimethylsuberimidate (DMS), formalin, dimethyladipimidate (DMA), dithio-bis(succinimidyl propionate) (DSP), disuccinimidyl tartrate (DST), ethylene glycol bis (succinimidyl succinate) (EGS), and combinations thereof.

22. The method of clause 10, wherein the staining agent is varied between two or more of acridine orange, Bismarck brown, carmine, Coomassie blue, cresyl violet, 4,6-diamidino-2-phenylindole (DAPI), eosin, hematoxylin, hematoxylin & eosin (H&E), ethidium bromide, acid fuchsine, iodine, methyl green, bisbenzimides, iodine, methyl green, methylene blue, neutral red, Nile blue, Nile red, osmium tetroxide, propidium iodide, rhodamine, safrain, radioisotopes, fluorophores, chemiluminescent compounds, bioluminescent compounds, and combinations thereof.

23. The method of any one of clauses 1-22, wherein the at least one image property comprises image brightness, image sharpness, or both.

24. The method of any one of clauses 1-23, wherein the at least one image property is quantified by obtaining at least one image signal for each permeabilized tissue section representing a variation in the at least one parameter, determining an intensity for each image signal, and preparing a plot of the image signal intensities versus the variations in the parameter.

25. The method of any one of clauses 1-24, wherein the at least one image property is quantified by obtaining a first image of each permeabilized tissue section and the array area on which it is placed, applying a mask to the area surrounding the tissue section on the array area, obtaining a mask image of each tissue section and the surrounding array area, wherein the mask minimizes or eliminates background region signal from the array area surrounding the tissue section, and merging each first image and each corresponding mask image to obtain a tissue image for each of the permeabilized tissue sections.

26. The method of clause 25, further comprising the steps of preparing a first plot of pixel count versus image intensity for each first image, preparing a second plot of pixel count verses image intensity for each mask image, and preparing a third plot of pixel count versus image intensity for each tissue section.

27. The method of any one of clauses 1-26, wherein the at least one image property is quantified using Fast Fourier Transform (FFT).

28. The method of any one of clauses 1-27, further comprising the steps of obtaining an FFT image of each permeabilized tissue section, and processing and comparing the FFT images for each of the permeabilized tissue sections.

29. The method of clause 28, wherein the FFT images are processed by extracting a radial profile of each image, by obtaining a power spectrum of each image, or both.

30. The method any one of clauses 28 or 29, further comprising the step of calculating at least one metric to determine the resolution of each FFT image.

31. The method of clause 30, wherein the at least one metric comprises an average frequency over a selected range of frequencies, an average intensity of a selected range of frequencies, and a ratio of frequencies over a plurality of selected ranges.

32. The method of any one of clauses 1-31, wherein the tissue sample is from a mammal, from one or more of a mammalian brain, olfactory bulb, spleen, lung, esophagus, skin, liver, reproductive organ, heart, abdomen and intestines.

33. A quantitative method of optimizing the permeabilization of tissue samples used for spatial transcriptomics, comprising the steps of:
 a) selecting two or more parameters that influence permeabilization in the tissue sample;
 b) preparing a first plurality of sections of the tissue sample for permeabilization;
 c) permeabilizing the first plurality of sections of the tissue sample, wherein the first of the two or more permeabilization parameters is varied for the different tissue sections;
 d) generating a cDNA footprint of each of the first plurality of permeabilized tissue sections,
 e) imaging the cDNA footprint for each of the tissue sections;
 f) determining a level of permeabilization for each tissue section of the first plurality of tissue sections by quantifying at least one image property that is determinative of permeabilization;
 g) correlating the at least one image property with the variations in the first parameter to determine a first value for the first parameter that yields an optimum level of permeabilization based on the first parameter;
 h) preparing a second plurality of tissue sections of tissue sample for permeabilization;
 i) permeabilizing the second plurality of tissue sections, wherein the second of the two permeabilization parameters is varied for the different tissue sections;
 j) generating a cDNA footprint of each of the second plurality of permeabilized tissue sections;
 k) imaging the cDNA footprint for each of the tissue sections;

l) determining a level of permeabilization for each tissue section of the second plurality of tissue sections by quantifying at least one image property that is determinative of permeabilization; and m) correlating the at least one image property with the variations in the second parameter to determine a second value for the second parameter that yields an optimum level of permeabilization based on the second parameter, and based on the first and second values determine the optimal permeabilization of the tissue sample.

34. The method clause 33, further comprising the steps of:
   a) preparing a third plurality of tissue sections of the tissue sample for permeabilization;
   b) varying a third parameter at different sections of the third plurality during permeabilization;
   c) determining a level of permeabilization for each section of the third plurality of sections of the tissue sample by quantifying at least one image property that is determinative of permeabilization;
   d) correlating the at least one image property with the variations in the third parameter to determine a third value for the third parameter that yields an optimum level of permeabilization based on the third parameter; and
   e) implementing the third value along with the first and second values to determine the optimal permeabilization of the tissue sample.

35. The method of clause 34, further comprising the steps of:
   a) preparing a fourth plurality of sections of the tissue sample for permeabilization;
   b) varying a fourth of the two or more parameters at different sections of the fourth plurality during permeabilization;
   c) determining a level of permeabilization for each section of the fourth plurality of sections of the tissue sample by quantifying at least one image property that is determinative of permeabilization;
   d) correlating the at least one image property with the variations in the fourth parameter to determine a fourth value for the fourth parameter that yields an optimum level of permeabilization based on the fourth parameter; and
   e) implementing the fourth value along with the first, second and third values to determine the optimal permeabilization of the tissue sample.

36. The method of clause 35, comprising varying at least a sixth of the one or more parameters and repeating steps a-e.

37. The method of any of clauses 33-36, wherein the at least one image property comprises image brightness, image sharpness, or both.

38. The method of any one of clauses 33-37, wherein the two or more parameters are selected from permeabilization time, permeabilization temperature, permeabilization reagent, tissue fixing agent, tissue staining agent, and combinations thereof.

39. The method of clause 38, wherein the two or more parameters are varied sequentially or simultaneously.

40. The method clause 33, wherein the at least one image property is quantified by obtaining at least one image signal for each permeabilized tissue section representing a variation in each of the two or more parameters, determining an intensity for each image signal, and preparing plots of the image intensities versus the variations in each parameter.

41. The method of clause 33, wherein the at least one image property is quantified by obtaining a first image of each permeabilized tissue section and the array area on which it is placed, applying a mask to the area surrounding the tissue section on the array area, obtaining a mask image of each tissue section and the surrounding array area, wherein the mask minimizes or eliminates background region signal from the array area surrounding the tissue section, and merging the first image and each corresponding mask image to obtain a tissue image for each of the permeabilized tissue sections.

42. The method of clause 41, further comprising the steps of preparing a first plot of pixel count versus image intensity for each first image, preparing a second plot of pixel count verses image intensity for each mask image, and preparing a third plot of pixel count versus image intensity for each tissue image.

43. The method of any one of clauses 33-42, wherein the at least one image property is quantified using Fast Fourier Transform (FFT), further comprising the steps of obtaining an FFT image of each permeabilized tissue section and processing and comparing the FFT images for each of the tissue sections.

44. The method of clause 43, wherein the FFT images are processed by one or more of extracting a radial profile of each image and obtaining a power spectrum of each image.

45. The method of one of clauses 43 and 44, further comprising the step of calculating at least one metric to determine the resolution of each image, wherein the at least one metric includes an average frequency over a selected range of frequencies, an average intensity of a selected range of frequencies, and a ratio of frequencies over a plurality of selected ranges.

46. An instrument for quantitatively optimizing the permeabilization of tissue samples used for spatial transcriptomics, comprising:
   a) an apparatus for receiving and storing data for at least one parameter that influences permeabilization in the tissue sample;
   b) an apparatus for correlating variations in the at least one parameter with at least one image property that is determinative of permeabilization in the tissue sample;
   c) an apparatus for determining an optimum value for the at least one parameter based on the correlation between the variations in the parameter and the image property;
   d) an apparatus for storing the optimum value of the at least one parameter; and
   e) an apparatus for informing a user of the optimum value of the at least one parameter.

47. The instrument of clause 46, wherein the apparatus for receiving and storing data comprises receiving and storing data for multiple parameters simultaneously, receiving and storying FFT image data, and the apparatus for informing a user comprises informing the user of optimum values for each of the multiple parameters.

48. The instrument of clause 46, wherein the at least one parameter is selected from the group consisting of permeabilization time, permeabilization temperature, permeabilization reagent, tissue fixing agent, tissue staining agent, and combinations thereof.

49. The instrument of clause 46, wherein the apparatus for correlating variations in the at least one parameter with at least one image property comprises apparatus for correlating variations in the at least one parameter with multiple image properties that are determinative of permeabilization, wherein the at least one image property is image brightness, image sharpness, or both.

50. The method of one of clauses 23 and 37, or the instrument of clause 49, wherein the image brightness is quantified by determining a pixel intensity distribution for each variation in the parameter, and wherein the step of correlating the image brightness with the variations in the parameter comprises the step of plotting a graph of pixel intensity distribution versus the variations in the parameter.

51. The method of one of clauses 23 and 37, or the instrument of clause 49, wherein the image brightness is quantified by converting the photomicrographic images into spot images and analyzing pixel intensities of an array of spots within each spot image.

52. The method of clause 51, wherein the step of analyzing pixel intensities comprises determining an average pixel intensity for pixels within each spot in the array and assigning a pixel value of zero to pixels present in spaces between the spots, or determining an average of pixel intensities comprises determining an average pixel intensity for pixels within each spot and pixels within a defined vicinity of each spot.

53. The method of one of clauses 23 and 37, or the instrument of clause 49, wherein the image sharpness is quantified by one or more of
 a) determining the absolute central moment for each variation in the parameter,
 b) determining the Brenner gradient for each variation in the parameter,
 c) determining the image contrast and/or the image contrast A for each variation in the parameter,
 d) determining the image curvature for each variation in the parameter,
 e) determining the DCT energy ratio, DCT reduced energy ratio, DCT energy ratio A and/or DCT reduced energy ratio A for each variation in the parameter,
 f) determining the gaussian derivative for each variation in the parameter,
 g) determining the gray level variance and/or the gray level local variance for each variation in the parameter,
 h) determining the normalized GLV for each variation in the parameter,
 i) determining the energy of gradient for each variation in the parameter,
 j) determining the thresholded gradient for each variation in the parameter,
 k) determining the squared gradient for each variation in the parameter,
 l) determining the Hemli's mean for each variation in the parameter,
 m) determining the histogram entropy and/or the histogram range for each variation in the parameter,
 n) by determining the energy of laplacian and/or the modified lablacian, and/or the variance of laplacian, and/or the diagonal lapalcian for each variation in the parameter,
 o) determining the steerable filters for each variation in the parameter,
 p) determining the spatial frequency for each variation in the parameter,
 q) determining the Tenengrad value and/or Tenengrad variance for each variation in the parameter,
 r) determining the Vollath's correlation for each variation in the parameter,
 s) determining the sum of wavelet coefficients, the sum of wavelet coefficients A, and/or the variance of wavelets for each variation in the parameter, and
 t) determining the multi-level two-dimensional inverse FWT and/or the multi-level two-dimensional FWT A for each variation in the parameter.

54. The method of any one of clauses 1-45, wherein the step of correlating the at least one image property with the variations in the parameter comprises plotting a plurality of image properties versus the variations in the parameter using a heatmap.

55. The method of any one of clauses 23 and 38, or the instrument of clause 49, wherein the image brightness is quantified by determining a pixel intensity distribution for each variation in the parameter.

56. The method of clause 55, wherein the step of correlating the image brightness with the variations in the parameter comprises the step of plotting a graph of pixel intensity distribution versus the variations in the parameter.

57. A quantitative method of optimizing the permeabilization of tissue samples used for spatial transcriptomics, comprising the steps of:
 a) selecting two or more parameters that influence permeabilization in the tissue sample;
 b) preparing a first plurality of sections of the tissue sample for permeabilization;
 c) permeabilizing the first plurality of sections of the tissue sample, wherein the first of the two or more permeabilization parameters is varied for the different tissue sections;
 d) generating a cDNA footprint of each of the first plurality of permeabilized tissue sections,
 e) imaging the cDNA footprint for each of the tissue sections;
 f) determining a level of permeabilization for each tissue section of the first plurality of tissue sections by quantifying at least one image property that is determinative of permeabilization;
 g) correlating the at least one image property with the variations in the first parameter to determine a first value for the first parameter that yields an optimum level of permeabilization based on the first parameter;
 h) performing steps b) through g) with a second plurality of sections of the tissue sample; and
 i) correlating the at least one image property with the variations in the second parameter to determine a second value for the second parameter that yields an optimum level of permeabilization based on the second parameter, and based on the first and second values determine the optimal permeabilization of the tissue sample.

58. The method of clause 57, further comprising the steps of:
 a) preparing a third plurality of tissue sections of the tissue sample for permeabilization;
 b) varying a third parameter at different sections of the third plurality during permeabilization;
 c) determining a level of permeabilization for each section of the third plurality of sections of the tissue sample by quantifying at least one image property that is determinative of permeabilization;
 d) correlating the at least one image property with the variations in the third parameter to determine a third value for the third parameter that yields an optimum level of permeabilization based on the third parameter; and
e) implementing the third value along with the first and second values to determine the optimal permeabilization of the tissue sample.

59. The method of clause 58, further comprising the steps of:
a) preparing a fourth plurality of sections of the tissue sample for permeabilization;
b) varying a fourth of the two or more parameters at different sections of the fourth plurality during permeabilization;
c) determining a level of permeabilization for each section of the fourth plurality of sections of the tissue sample by quantifying at least one image property that is determinative of permeabilization;
d) correlating the at least one image property with the variations in the fourth parameter to determine a fourth value for the fourth parameter that yields an optimum level of permeabilization based on the fourth parameter; and
e) implementing the fourth value along with the first, second and third values to determine the optimal permeabilization of the tissue sample.

60. The method of clause 59, comprising varying at least a sixth of the one or more parameters and repeating steps a-e.

61. The method of clause 57, wherein the at least one image property comprises image brightness, image sharpness, or both.

62. The method of clause 61, wherein the image sharpness is quantified by one or more of
a) determining the absolute central moment for each variation in the parameter,
b) determining the Brenner gradient for each variation in the parameter,
c) determining the image contrast and/or the image contrast A for each variation in the parameter,
d) determining the image curvature for each variation in the parameter,
e) determining the DCT energy ratio, DCT reduced energy ratio, DCT energy ratio A and/or DCT reduced energy ratio A for each variation in the parameter,
f) determining the gaussian derivative for each variation in the parameter,
g) determining the gray level variance and/or the gray level local variance for each variation in the parameter,
h) determining the normalized GLV for each variation in the parameter,
i) determining the energy of gradient for each variation in the parameter,
j) determining the thresholded gradient for each variation in the parameter,
k) determining the squared gradient for each variation in the parameter,
l) determining the Hemli's mean for each variation in the parameter,
m) determining the histogram entropy and/or the histogram range for each variation in the parameter,
n) by determining the energy of laplacian and/or the modified laplacian, and/or the variance of laplacian, and/or the diagonal laplacian for each variation in the parameter,
o) determining the steerable filters for each variation in the parameter,
p) determining the spatial frequency for each variation in the parameter,
q) determining the Tenengrad value and/or Tenengrad variance for each variation in the parameter,
r) determining the Vollath's correlation for each variation in the parameter,
s) determining the sum of wavelet coefficients, the sum of wavelet coefficients A, and/or the variance of wavelets for each variation in the parameter, and
t) determining the multi-level two-dimensional inverse FWT and/or the multi-level two-dimensional FWT A for each variation in the parameter.

63. The method of clause 61, wherein the image brightness is quantified by:
a) determining a pixel intensity distribution for each variation in the parameter, and wherein the step of correlating the image brightness with the variations in the parameter comprises the step of plotting a graph of pixel intensity distribution versus the variations in the parameter; or
b) converting the photomicrographic images into spot images and analyzing pixel intensities of an array of spots within each spot image.

64. The method of clause 63, wherein the step of analyzing pixel intensities comprises determining an average pixel intensity for pixels within each spot in the array and assigning a pixel value of zero to pixels present in spaces between the spots, or determining an average of pixel intensities comprises determining an average pixel intensity for pixels within each spot and pixels within a defined vicinity of each spot.

65. The method of clause 57, wherein the two or more parameters are:
a) selected from permeabilization time, permeabilization temperature, permeabilization reagent, tissue fixing agent, tissue staining agent, and combinations thereof; or
b) varied sequentially or simultaneously.

66. The method of clause 65, wherein the image brightness is quantified by determining a pixel intensity distribution for each variation in the parameter.

67. The method of clause 66, wherein the step of correlating the image brightness with the variations in the parameter comprises the step of plotting a graph of pixel intensity distribution versus the variations in the parameter.

68. The method of clause 57, wherein the step of correlating the at least one image property with the variations in the parameter comprises plotting a plurality of image properties versus the variations in the parameter using a heatmap.

69. The method of clause 57, wherein the at least one image property is:
a) quantified by obtaining at least one image signal for each permeabilized tissue section representing a variation in each of the two or more parameters, determining an intensity for each image signal, and preparing plots of the image intensities versus the variations in each parameter; or
b) quantified by obtaining a first image of each permeabilized tissue section and the array area on which it is placed, applying a mask to the area surrounding the tissue section on the array area, obtaining a mask image of each tissue section and the surrounding array area, wherein the mask minimizes or eliminates background region signal from the array area surrounding the tissue section, and merging the first image and each corresponding mask image to obtain a tissue image for each of the permeabilized tissue sections; or c) quantified using Fast Fourier Transform (FFT), further comprising the steps of obtaining an FFT image of each permeabilized tissue section and processing and comparing the FFT images for each of the tissue sections.

70. The method of clause 69, further comprising the steps of preparing a first plot of pixel count versus image intensity for each first image, preparing a second plot of pixel count verses image intensity for each mask image, and preparing a third plot of pixel count versus image intensity for each tissue image.

71. The method of clause 69, wherein the FFT images are processed by one or more of extracting a radial profile of each image and obtaining a power spectrum of each image.

72. The method of clause 69, further comprising the step of calculating at least one metric to determine the resolution of each image, wherein the at least one metric includes an average frequency over a selected range of frequencies, an average intensity of a selected range of frequencies, and a ratio of frequencies over a plurality of selected ranges.

73. An instrument for quantitatively optimizing the permeabilization of tissue samples used for spatial transcriptomics, comprising:
   a) an apparatus for receiving and storing data for at least one parameter that influences permeabilization in the tissue sample;
   b) an apparatus for correlating variations in the at least one parameter with at least one image property that is determinative of permeabilization in the tissue sample;
   c) an apparatus for determining an optimum value for the at least one parameter based on the correlation between the variations in the parameter and the image property;
   d) an apparatus for storing the optimum value of the at least one parameter; and
   e) an apparatus for informing a user of the optimum value of the at least one parameter.

74. The instrument of clause 73, wherein the apparatus for receiving and storing data comprises receiving and storing data for multiple parameters simultaneously, receiving and storying FFT image data, and the apparatus for informing a user comprises informing the user of optimum values for each of the multiple parameters.

75. The instrument of clause 73, wherein the at least one parameter is selected from the group consisting of permeabilization time, permeabilization temperature, permeabilization reagent, tissue fixing agent, tissue staining agent, and combinations thereof.

76. The instrument of clause 73, wherein the apparatus for correlating variations in the at least one parameter with at least one image property comprises apparatus for correlating variations in the at least one parameter with multiple image properties that are determinative of permeabilization, wherein the at least one image property is image brightness, image sharpness, or both.

The embodiments of the invention described herein are exemplary, and various modifications and improvements can be made without departing from the spirit and scope of the invention. The scope of the invention is defined by the appended claims, and all changes that fall within the meaning and range of equivalents are intended to be embraced therein.

For the descriptions herein and the appended claims, the singular forms "a", and "an" include plural referents unless the context clearly indicates otherwise. Thus, for example, reference to "a protein" includes more than one protein, and reference to "a compound" refers to more than one compound. It is further noted that the claims may be drafted to exclude any optional element. As such, this statement is intended to serve as antecedent basis for use of such exclusive terminology as "solely," "only" and the like in connection with the recitation of claim elements or use of a "negative" limitation. The use of "comprise," "comprises," "comprising" "include," "includes," and "including" are interchangeable and not intended to be limiting. It is to be further understood that where descriptions of various embodiments use the term "comprising," those skilled in the art would understand that in some specific instances, an embodiment can be alternatively described using language "consisting essentially of" or "consisting of."

Where a range of values is provided, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both limits, ranges excluding (i) either or (ii) both of those included limits are also included in the invention. For example, "1 to 50," includes "2 to 25," "5 to 20," "25 to 50," "1 to 10," etc.

All publications, patents, patent applications, and other documents referenced in this disclosure are hereby incorporated by reference in their entireties for all purposes to the same extent as if each individual publication, patent, patent application or other document were individually indicated to be incorporated by reference herein for all purposes.

We claim:

1. A quantitative method of optimizing the permeabilization of tissue samples used for spatial transcriptomics, comprising the steps of:
   a) selecting two or more parameters that influence permeabilization in the tissue sample;
   b) preparing a first plurality of sections of the tissue sample for permeabilization;
   c) permeabilizing the first plurality of sections of the tissue sample, wherein the first of the two or more permeabilization parameters is varied for the different tissue sections;
   d) generating a cDNA footprint of each of the first plurality of permeabilized tissue sections,
   e) imaging the cDNA footprint for each of the tissue sections;
   f) determining a level of permeabilization for each tissue section of the first plurality of tissue sections by quantifying at least one image property that is determinative of permeabilization;
   g) correlating the at least one image property with the variations in the first parameter to determine a first value for the first parameter that yields an optimum level of permeabilization based on the first parameter;

h) performing steps b) through g) with a second plurality of sections of the tissue sample; and i) correlating the at least one image property with the variations in the second parameter to determine a second value for the second parameter that yields an optimum level of permeabilization based on the second parameter, and based on the first and second values determine the optimal permeabilization of the tissue sample.

2. The method of claim 1, further comprising the steps of:

a) preparing a third plurality of tissue sections of the tissue sample for permeabilization;

b) varying a third parameter at different sections of the third plurality during permeabilization;

c) determining a level of permeabilization for each section of the third plurality of sections of the tissue sample by quantifying at least one image property that is determinative of permeabilization;

d) correlating the at least one image property with the variations in the third parameter to determine a third value for the third parameter that yields an optimum level of permeabilization based on the third parameter; and e) implementing the third value along with the first and second values to determine the optimal permeabilization of the tissue sample.

3. The method of claim 2, further comprising the steps of:

a) preparing a fourth plurality of sections of the tissue sample for permeabilization;

b) varying a fourth of the two or more parameters at different sections of the fourth plurality during permeabilization;

c) determining a level of permeabilization for each section of the fourth plurality of sections of the tissue sample by quantifying at least one image property that is determinative of permeabilization;

d) correlating the at least one image property with the variations in the fourth parameter to determine a fourth value for the fourth parameter that yields an optimum level of permeabilization based on the fourth parameter; and e) implementing the fourth value along with the first, second and third values to determine the optimal permeabilization of the tissue sample.

4. The method of claim 3, comprising varying at least a sixth of the one or more parameters and repeating steps a-e.

5. The method of claim 1, wherein the at least one image property comprises image brightness, image sharpness, or both.

6. The method of claim 5, wherein the image sharpness is quantified by one or more of a) determining an absolute central moment for each variation in the parameter, b) determining a Brenner gradient for each variation in the parameter, c) determining an image contrast and/or the image contrast A for each variation in the parameter, d) determining an image curvature for each variation in the parameter, e) determining a DCT energy ratio, DCT reduced energy ratio, DCT energy ratio A and/or DCT reduced energy ratio A for each variation in the parameter, f) determining a gaussian derivative for each variation in the parameter, g) determining a gray level variance and/or the gray level local variance for each variation in the parameter, h) determining a normalized GLV for each variation in the parameter, i) determining an energy of gradient for each variation in the parameter, j) determining a thresholded gradient for each variation in the parameter, k) determining a squared gradient for each variation in the parameter, l) determining a Hemli's mean for each variation in the parameter, m) determining a histogram entropy and/or the histogram range for each variation in the parameter, n) by determining an energy of laplacian and/or a modified laplacian, and/or a variance of laplacian, and/or a diagonal laplacian for each variation in the parameter, o) determining a steerable filters for each variation in the parameter, p) determining a spatial frequency for each variation in the parameter, q) determining a Tenengrad value and/or Tenengrad variance for each variation in the parameter, r) determining a Vollath's correlation for each variation in the parameter, s) determining a sum of wavelet coefficients, a sum of wavelet coefficients A, and/or a variance of wavelets for each variation in the parameter, and t) determining a multi-level two-dimensional inverse FWT and/or a multi-level two-dimensional FWT A for each variation in the parameter.

7. The method of claim 5, wherein the image brightness is quantified by:

a) determining a pixel intensity distribution for each variation in the parameter, and wherein the step of correlating the image brightness with the variations in the parameter comprises the step of plotting a graph of pixel intensity distribution versus the variations in the parameter; or b) converting the photomicrographic images into spot images and analyzing pixel intensities of an array of spots within each spot image.

8. The method of claim 7, wherein the step of analyzing pixel intensities comprises determining an average pixel intensity for pixels within each spot in the array and assigning a pixel value of zero to pixels present in spaces between the spots, or determining an average of pixel intensities comprises determining an average pixel intensity for pixels within each spot and pixels within a defined vicinity of each spot.

9. The method of claim 1, wherein the two or more parameters are:

a) selected from permeabilization time, permeabilization temperature, permeabilization reagent, tissue fixing agent, tissue staining agent, and combinations thereof; or b) varied sequentially or simultaneously.

10. The method of claim 9, wherein the image brightness is quantified by determining a pixel intensity distribution for each variation in the parameter.

11. The method of claim 10, wherein the step of correlating the image brightness with the variations in the parameter comprises the step of plotting a graph of pixel intensity distribution versus the variations in the parameter.

12. The method of claim 1, wherein the step of correlating the at least one image property with the variations in the parameter comprises plotting a plurality of image properties versus the variations in the parameter using a heatmap.

13. The method of claim 1, wherein the at least one image property is:
   a) quantified by obtaining at least one image signal for each permeabilized tissue section representing a variation in each of the two or more parameters, determining an intensity for each image signal, and preparing plots of the image intensities versus the variations in each parameter; or
   b) quantified by obtaining a first image of each permeabilized tissue section and the array area on which it is placed, applying a mask to the area surrounding the tissue section on the array area, obtaining a mask image of each tissue section and the surrounding array area, wherein the mask minimizes or eliminates background region signal from the array area surrounding the tissue section, and merging the first image and each corresponding mask image to obtain a tissue image for each of the permeabilized tissue sections; or
   c) quantified using Fast Fourier Transform (FFT), further comprising the steps of obtaining an FFT image of each permeabilized tissue section and processing and comparing the FFT images for each of the tissue sections.

14. The method of claim 13, further comprising the steps of preparing a first plot of pixel count versus image intensity for each first image, preparing a second plot of pixel count verses image intensity for each mask image, and preparing a third plot of pixel count versus image intensity for each tissue image.

15. The method of claim 13, wherein the FFT images are processed by one or more of extracting a radial profile of each image and obtaining a power spectrum of each image.

16. The method of claim 13, further comprising the step of calculating at least one metric to determine the resolution of each image, wherein the at least one metric includes an average frequency over a selected range of frequencies, an average intensity of a selected range of frequencies, and a ratio of frequencies over a plurality of selected ranges.

17. An instrument for quantitatively optimizing the permeabilization of tissue samples used for spatial transcriptomics, comprising:
   a) an apparatus for receiving and storing data for at least one parameter that influences permeabilization in the tissue sample;
   b) an apparatus for correlating variations in the at least one parameter with at least one image property that is determinative of permeabilization in the tissue sample;
   c) an apparatus for determining an optimum value for the at least one parameter based on the correlation between the variations in the parameter and the image property;
   d) an apparatus for storing the optimum value of the at least one parameter; and
   e) an apparatus for informing a user of the optimum value of the at least one parameter.

18. The instrument of claim 17, wherein the apparatus for receiving and storing data comprises receiving and storing data for multiple parameters simultaneously, receiving and storing FFT image data, and the apparatus for informing the user comprises informing the user of optimum values for each of the multiple parameters.

19. The instrument of claim 17, wherein the at least one parameter is selected from the group consisting of permeabilization time, permeabilization temperature, permeabilization reagent, tissue fixing agent, tissue staining agent, and combinations thereof.

* * * * *